US010722180B2

(12) United States Patent
Zhang et al.

(10) Patent No.: US 10,722,180 B2
(45) Date of Patent: Jul. 28, 2020

(54) DEEP LEARNING-BASED DIAGNOSIS AND REFERRAL OF OPHTHALMIC DISEASES AND DISORDERS

(71) Applicants: AI TECHNOLOGIES INC., Grand Cayman (KY); THE REGENTS OF THE UNIVERSITY OF CALIFORNIA, Oakland, CA (US)

(72) Inventors: Kang Zhang, San Diego, CA (US); Rui Hou, Shenyang (CN); Lianghong Zheng, Shenyang (CN)

( * ) Notice: Subject to any disclaimer, the term of this patent is extended or adjusted under 35 U.S.C. 154(b) by 0 days.

(21) Appl. No.: 16/160,935

(22) Filed: Oct. 15, 2018

(65) Prior Publication Data

US 2019/0110753 A1 Apr. 18, 2019

Related U.S. Application Data

(60) Provisional application No. 62/572,384, filed on Oct. 13, 2017, provisional application No. 62/668,698, (Continued)

(51) Int. Cl.
*A61B 5/00* (2006.01)
*G16H 30/40* (2018.01)
(Continued)

(52) U.S. Cl.
CPC .......... *A61B 5/7267* (2013.01); *A61B 3/0025* (2013.01); *A61B 3/102* (2013.01); *A61B 3/12* (2013.01); *A61B 3/14* (2013.01); *G06N 20/00* (2019.01); *G16H 30/40* (2018.01); *A61B 5/0013* (2013.01); *A61B 5/0022* (2013.01); *A61B 5/021* (2013.01); *A61B 5/024* (2013.01); (Continued)

(58) Field of Classification Search
CPC ..... A61B 5/7267; A61B 5/0013; A61B 5/486; A61B 5/7282; A61B 5/0022; A61B 5/6898; A61B 3/102; A61B 3/12; A61B 3/14; A61B 3/0025; A61B 2576/02; G16H 30/40; G06N 20/00
See application file for complete search history.

(56) References Cited

U.S. PATENT DOCUMENTS 8,322,853 B2    12/2012  Marshall et al.
8,879,813 B1*   11/2014  Solanki ................. G16H 30/20
                                                     382/128
(Continued)

FOREIGN PATENT DOCUMENTS

WO    WO-2016154558 A1    9/2016
WO    WO-2019075410 A1    4/2019

OTHER PUBLICATIONS

Avila et al. Natural history of choroidal neovascularization in degenerative myopia. Ophthalmology 91:1573-1581 (1984).
(Continued)

*Primary Examiner* — Peter Luong
(74) *Attorney, Agent, or Firm* — Procopio, Cory, Hargreaves & Savitch; Jonathan D. Cheng

(57) ABSTRACT

Disclosed herein are systems, methods, devices, and media for carrying out medical diagnosis of ophthalmic diseases and conditions. Deep learning algorithms enable the automated analysis of ophthalmic images to generate predictions of comparable accuracy to clinical experts.

24 Claims, 29 Drawing Sheets
(24 of 29 Drawing Sheet(s) Filed in Color)

Related U.S. Application Data filed on May 8, 2018, provisional application No. 62/694,939, filed on Jul. 6, 2018.

(51) Int. Cl.
| | |
|---|---|
| G06N 20/00 | (2019.01) |
| A61B 3/00 | (2006.01) |
| A61B 3/10 | (2006.01) |
| A61B 3/12 | (2006.01) |
| A61B 3/14 | (2006.01) |
| A61B 5/053 | (2006.01) |
| A61B 5/024 | (2006.01) |
| A61B 5/021 | (2006.01) |

(52) U.S. Cl.
CPC ............. *A61B 5/0531* (2013.01); *A61B 5/486* (2013.01); *A61B 5/4872* (2013.01); *A61B 5/4875* (2013.01); *A61B 5/6898* (2013.01); *A61B 5/7282* (2013.01); *A61B 2576/02* (2013.01)

(56) References Cited

U.S. PATENT DOCUMENTS

| | | |
|---|---|---|
| 2010/0277691 A1 | 11/2010 | Huang et al. |
| 2016/0224892 A1 | 8/2016 | Sawada et al. |
| 2016/0292856 A1 | 10/2016 | Niemeijer et al. |

OTHER PUBLICATIONS

Bootcov et al. MIC-1, a novel macrophage inhibitory cytokine, is a divergent member of the TGF-beta superfamily. PNAS USA 94:11514-11519 (1997).
Bowl et al. Improving detection of mild loss of retinal light increment sensitivity at the posterior pole with the microperimeter MP1. Invest. Ophthalmol. Vis. Sci. 54:4666-4674 (2013).
Bradley. The Use of the Area Under the ROC Curve in the Evaluation of Machine Learning Algorithms. Pattern Recognition 30:1145-1159 (1997).
Cao. Multifarious functions of PDGFs and PDGFRs in tumor growth and metastasis. Trends Mol. Med. 19:460-473 (2013).
Cashman et al. Inhibition of choroidal neovascularization by adenovirus-mediated delivery of short hairpin RNAs targeting VEGF as a potential therapy for AMD. Invest. Ophthalmol. Vis. Sci. 47:3496-3504 (2006).
Chang et al. Myopia-related fundus changes in Singapore adults with high myopia. Am. J. Ophthalmol. 155:991-999.e1 (2013).
Choi et al. Hepatocyte growth factor induces proliferation of lens epithelial cells through activation of ERK1/2 and JNK/SAPK. Invest. Ophthalmol. Vis. Sci. 45, 2696-2704 (2004).
Costagliola et al. Effect of intravitreal ranibizumab injections on aqueous humour concentrations of vascular endothelial growth factor and pigment epithelium-derived factor in patients with myopic choroidal neovascularisation. Br. J. Ophthalmol. 99:1004-1008 (2015).
Cui et al. PDGF receptors are activated in human epiretinal membranes. Exp. Eye Res. 88:438-444 (2009).
Facts About Cataract. Available at: https://nei.nih.gov/health/cataract/cataract_facts. (Last reviewed Sep. 2015).
Funa et al. The roles of PDGF in development and during neurogenesis in the normal and diseased nervous system. J. Neuroimmune Pharmacol. 9:168-181 (2014).
Huang et al. Changes following supplementation with lutein and zeaxanthin in retinal function in eyes with early age-related macular degeneration: a randomised, double-blind, placebo-controlled trial. Br. J. Ophthalmol. 99(3):371-375 (2014).
Kermany et al. Identifying Medical Diagnoses and Treatable Diseases by Image-Based Deep Learning. Cell 172:1122-1131 e9 (2018).
Lambrecht et al. Growth differentiation factor 15, a marker of lung involvement in systemic sclerosis, is involved in fibrosis development but is not indispensable for fibrosis development. Arthritis Rheumatol 66:418-427 (2014).
Liu et al. Prevalence and progression of myopic retinopathy in Chinese adults: the Beijing Eye Study. Ophthalmology 117:1763-1768 (2010).
Molina-Martín et al. Normal values for microperimetry with the MAIA microperimeter: sensitivity and fixation analysis in healthy adults and children. Eur. J. Ophthalmol. 27:607-613 (2017).
Naidoo et al. Global Vision Impairment and Blindness Due to Uncorrected Refractive Error, 1990-2010. Optom. Vis. Sci. 93:227 (2016).
Ohno-Matsui et al. International photographic classification and grading system for myopic maculopathy. Am. J. Ophthalmol. 159:877-83.e7 (2015).
Ohno-Matsui. What Is the Fundamental Nature of Pathologic Myopia? Retina 37:1043-1048 (2017).
Philippe et al. Airway cell involvement in intermittent hypoxia-induced airway inflammation. Sleep Breath. 19:297-306 (2015).
Saw et al. Myopia and associated pathological complications. Ophthalmic Physiol. Opt. 25:381-391 (2005).
Schönbach et al. Macular Sensitivity Measured With Microperimetry in Stargardt Disease in the Progression of Atrophy Secondary to Stargardt Disease (ProgStar) Study: Report No. 7. JAMA Ophthalmol. 135:696-703 (2017).
Shin et al. Aqueous humor concentrations of vascular endothelial growth factor and pigment epithelium-derived factor in high myopic patients. Mol. Vis. 18:2265-2270 (2012).
Stevens et al. Global Prevalence of Vision Impairment and Blindness: Magnitude and Temporal Trends, 1990-2010. Ophthalmology 120:2377-2384 (2013).
Strelau et al. Expression and putative functions of GDF-15, a member of the TGF-beta superfamily, in human glioma and glioblastoma cell lines. Cancer Lett. 270:30-39 (2008).
Tang et al. Prevalence and Causes of Visual Impairment in a Chinese Adult Population: The Taizhou Eye Study. Ophthalmology 122:1480-1488 (2015).
Vongphanit et al. Prevalence and progression of myopic retinopathy in an older population. Ophthalmology 109:704-711 (2002).
Wang et al. Classification of early dry-type myopic maculopathy with macular choroidal thickness. Am. J. Ophthalmol. 153:669-77-677.e1-2 (2012).
Wong et al. Prevalence and causes of vision loss in East Asia: 1990-2010. Br. J. Ophthalmol. 98:599-604 (2014).
Zhang et al. Mechanism of TNF-$\alpha$-induced migration and hepatocyte growth factor production in human mesenchymal stem cells. J. Cell. Biochem. 111:469-475 (2010).
Zhou et al. Growth differentiation factor-15 (GDF-15), novel biomarker for assessing atrial fibrosis in patients with atrial fibrillation and rheumatic heart disease. Int. J. Clin. Exp. Med. 8:21201-21207 (2015).
Zhu et al. Fixation Stability and Refractive Error After Cataract Surgery in Highly Myopic Eyes. Am. J. Ophthalmol. 169:89-94 (2016).
Zhu et al. Molecular Inflammation in the Contralateral Eye After Cataract Surgery in the First Eye. Invest. Ophthalmol. Vis. Sci. 56:5566-5573 (2015).
Zhu et al. Proinflammatory status in the aqueous humor of high myopic cataract eyes. Exp. Eye Res. 142:13-18 (2016).
PCT/US2018/055723 International Search Report and Written Opinion dated Feb. 21, 2019.
Chen et al. Prevalence and Associated Risk Factors of Myopic Maculopathy in Elderly Chinese: The Shihpai Eye Study. Invest Ophthalmol Vis Sci 53(8):4868-4873.

\* cited by examiner

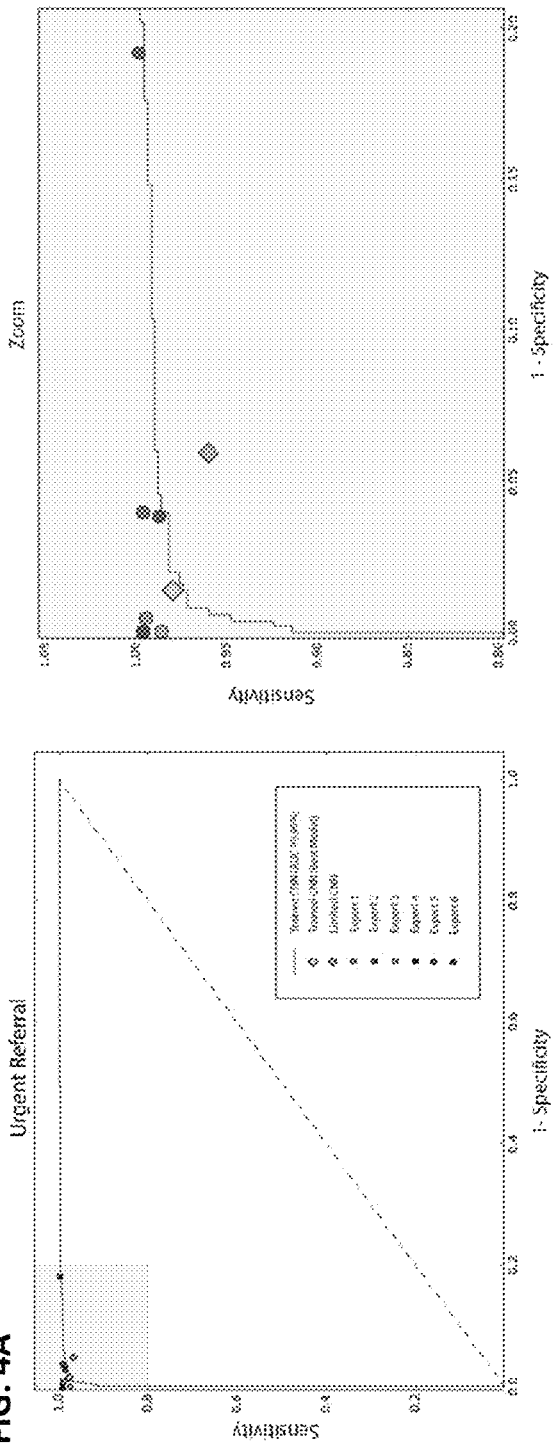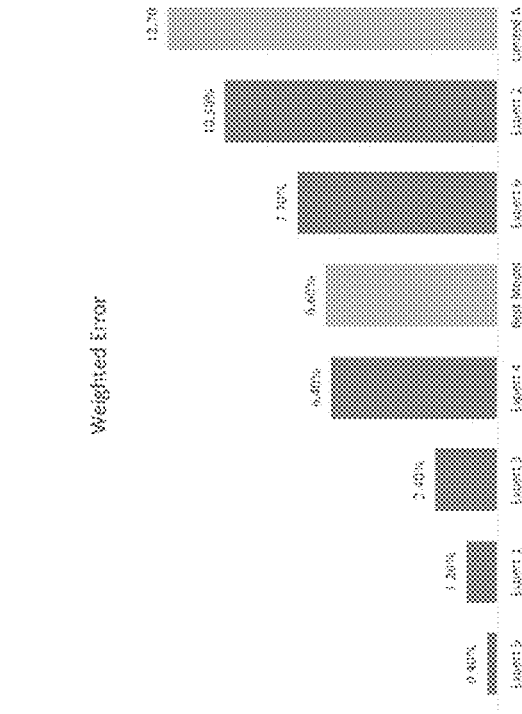
FIG. 4A
FIG. 4B
FIG. 4C

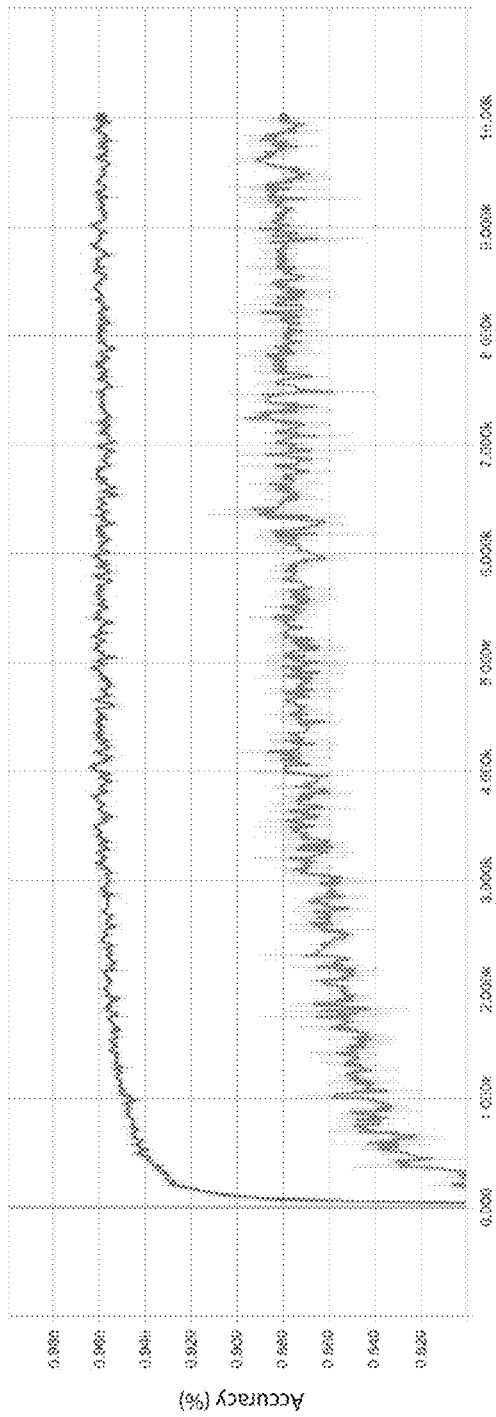
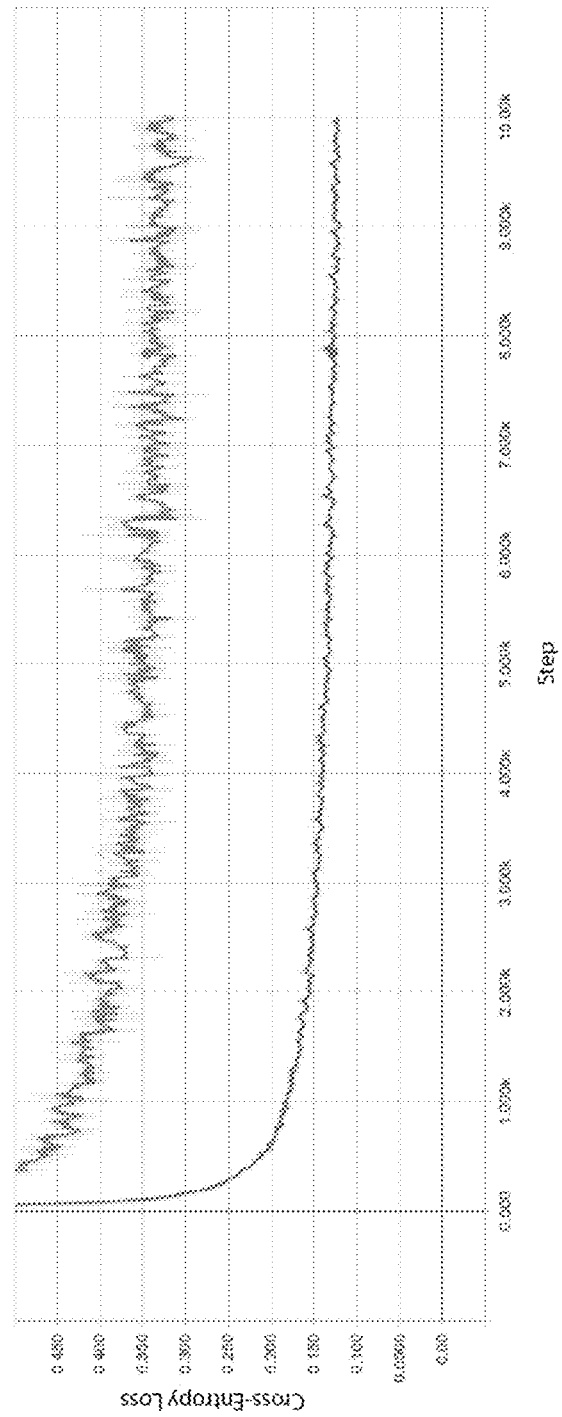
FIG. 5A
FIG. 5B

CNV vs Normal

DME vs Normal

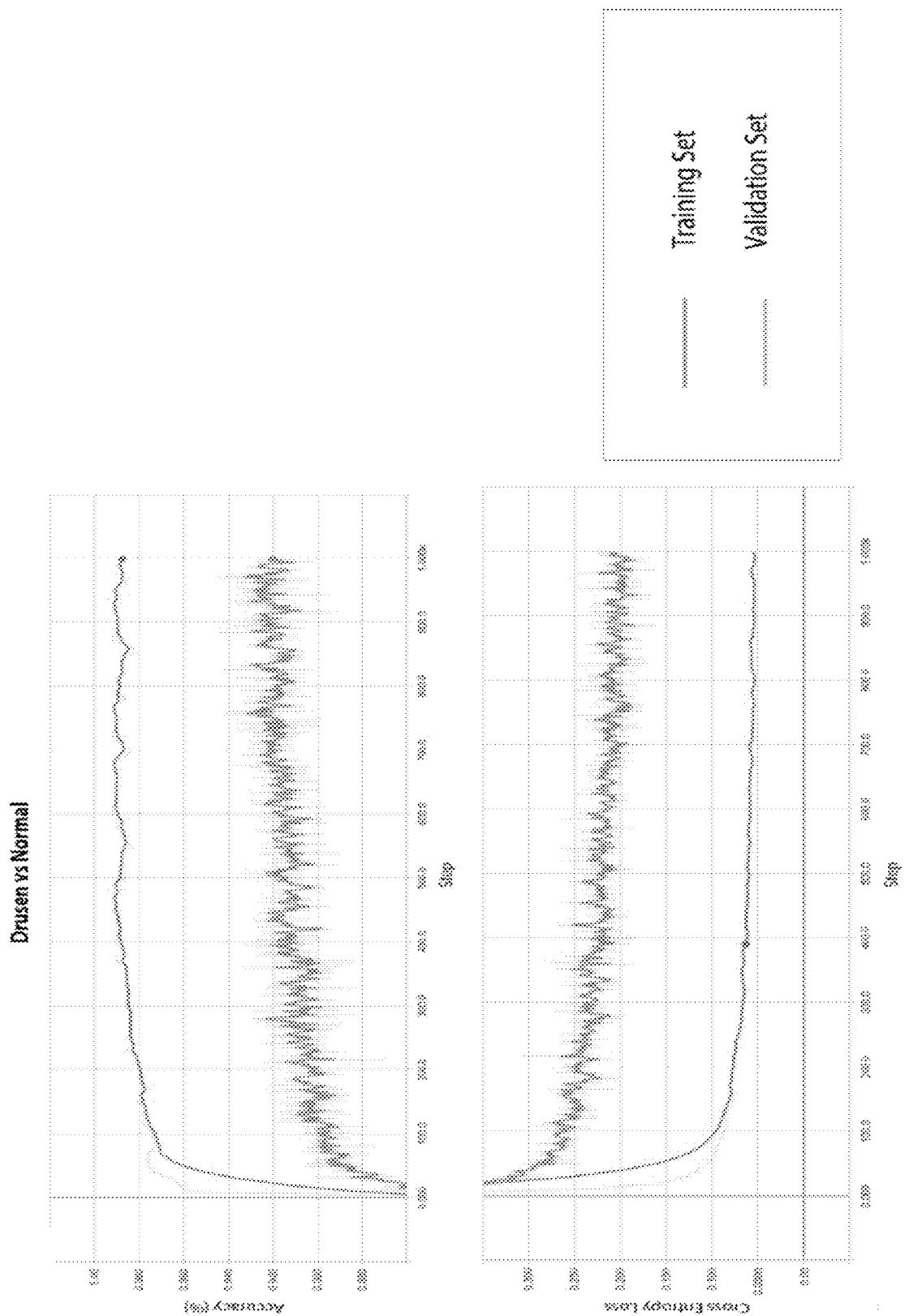

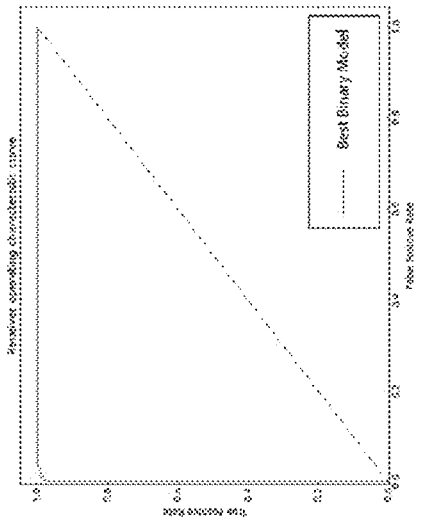
FIG. 8A  CNV v Normal
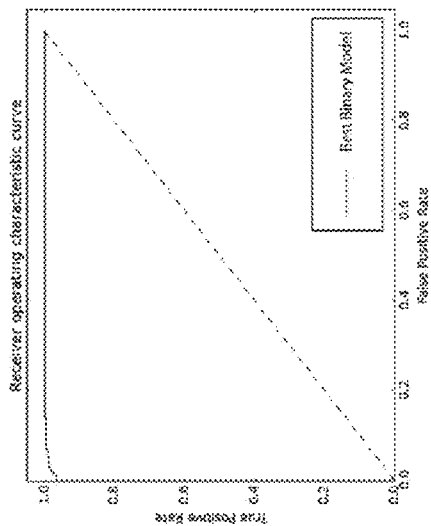
FIG. 8B  DME v Normal
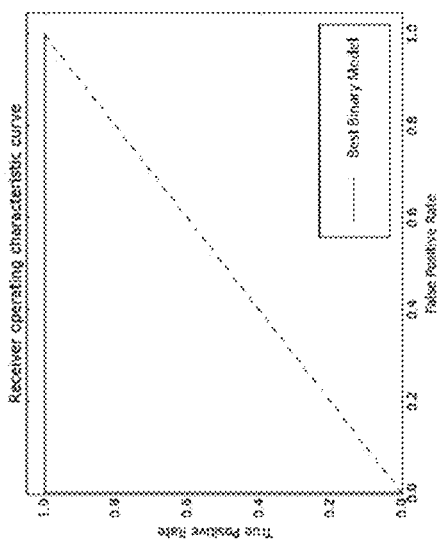
FIG. 8C  Drusen v Normal

FIG. 10A

|  | Predicted Labels |  |  |  |
|---|---|---|---|---|
|  | NORMAL | DRUSEN | CNV | DME |
| NORMAL | 0 | 1 | 1 | 1 |
| DRUSEN | 1 | 0 | 1 | 1 |
| CNV | 4 | 2 | 0 | 1 |
| DME | 4 | 2 | 1 | 0 |

True Labels

FIG. 10B

Expert 1

|  | Predicted Labels |  |  |  |
|---|---|---|---|---|
|  | NORMAL | DRUSEN | CNV | DME |
| NORMAL | 249 | 0 | 0 | 0 |
| DRUSEN | 0 | 245 | 5 | 0 |
| CNV | 0 | 5 | 246 | 0 |
| DME | 0 | 0 | 0 | 250 |

Expert 2

|  | Predicted Labels |  |  |  |
|---|---|---|---|---|
|  | NORMAL | DRUSEN | CNV | DME |
| NORMAL | 239 | 7 | 3 | 1 |
| DRUSEN | 13 | 223 | 8 | 6 |
| CNV | 0 | 6 | 237 | 7 |
| DME | 3 | 0 | 25 | 222 |

Expert 3

|  | Predicted Labels |  |  |  |
|---|---|---|---|---|
|  | NORMAL | DRUSEN | CNV | DME |
| NORMAL | 250 | 0 | 0 | 0 |
| DRUSEN | 3 | 245 | 2 | 0 |
| CNV | 0 | 1 | 246 | 3 |
| DME | 4 | 1 | 8 | 237 |

Expert 4

|  | Predicted Labels |  |  |  |
|---|---|---|---|---|
|  | NORMAL | DRUSEN | CNV | DME |
| NORMAL | 237 | 10 | 0 | 3 |
| DRUSEN | 0 | 233 | 17 | 0 |
| CNV | 0 | 3 | 242 | 5 |
| DME | 0 | 0 | 0 | 250 |

Expert 5

|  | Predicted Labels |  |  |  |
|---|---|---|---|---|
|  | NORMAL | DRUSEN | CNV | DME |
| NORMAL | 249 | 1 | 0 | 0 |
| DRUSEN | 0 | 249 | 1 | 0 |
| CNV | 0 | 1 | 249 | 0 |
| DME | 0 | 0 | 0 | 250 |

Expert 6

|  | Predicted Labels |  |  |  |
|---|---|---|---|---|
|  | NORMAL | DRUSEN | CNV | DME |
| NORMAL | 230 | 0 | 0 | 0 |
| DRUSEN | 0 | 180 | 35 | 0 |
| CNV | 0 | 0 | 250 | 0 |
| DME | 0 | 0 | 7 | 243 |

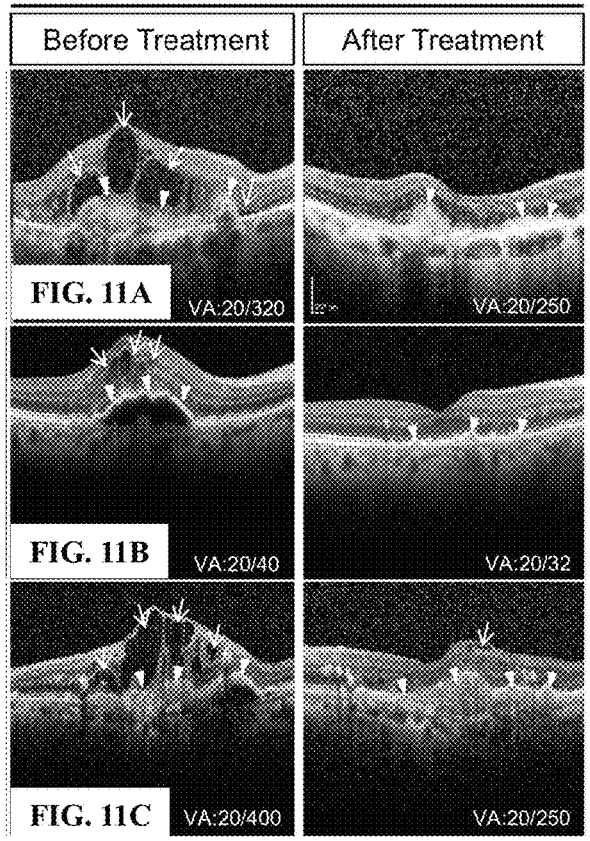
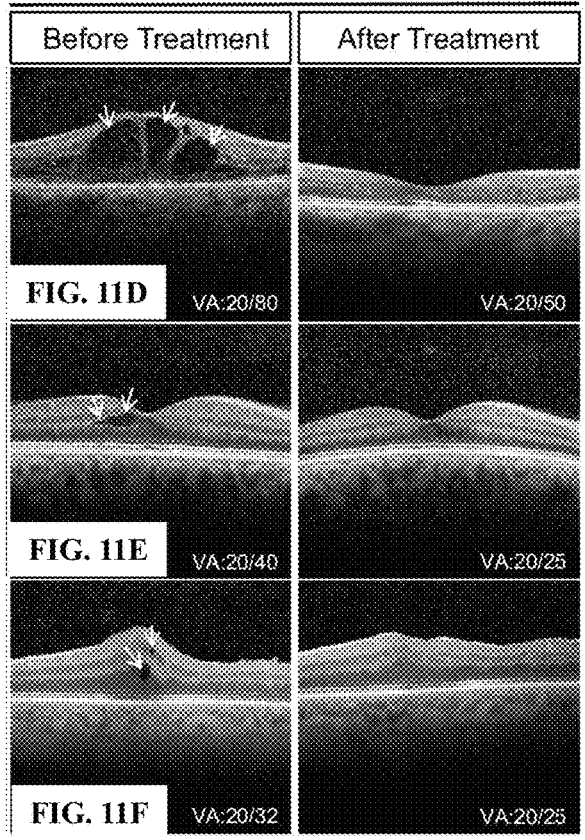
FIG. 11G
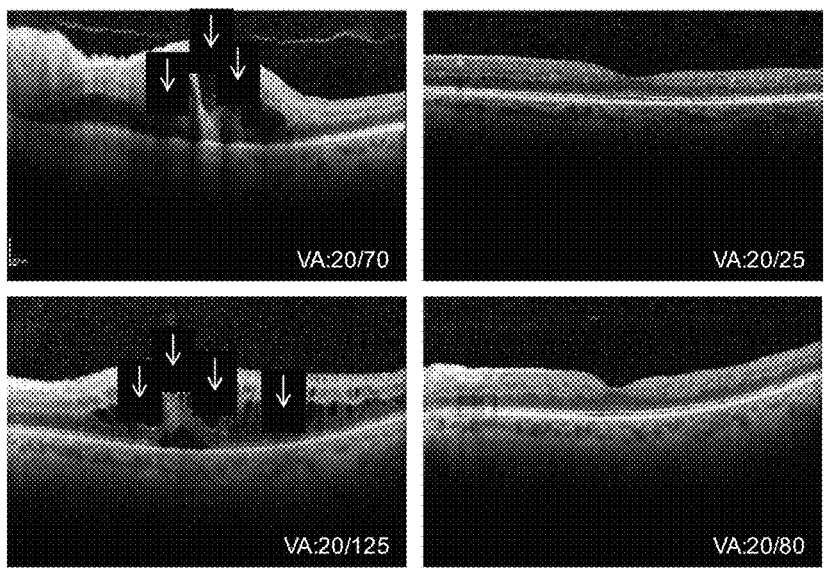

FIG. 15A
FIG. 15B
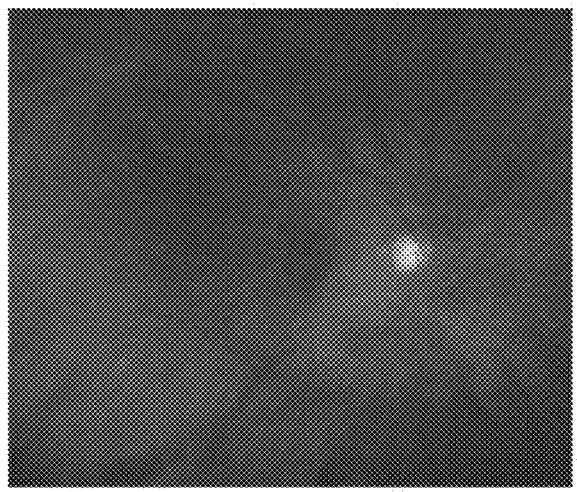
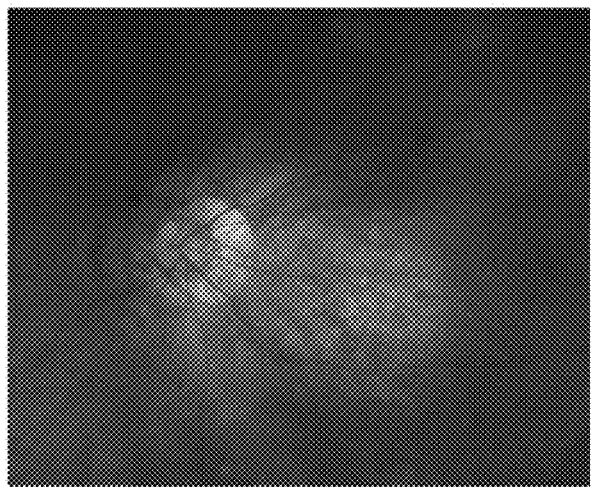
FIG. 15C
FIG. 15D
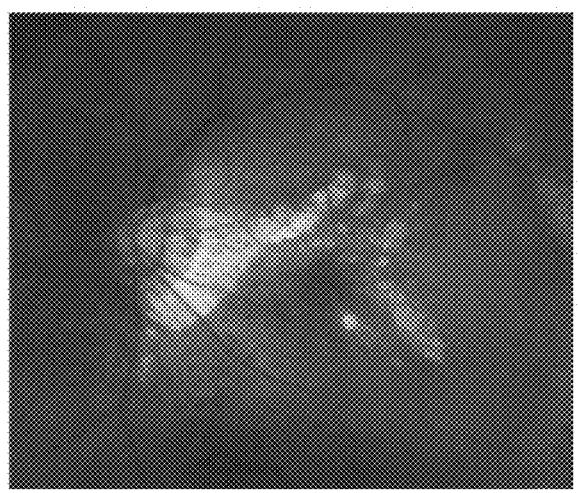
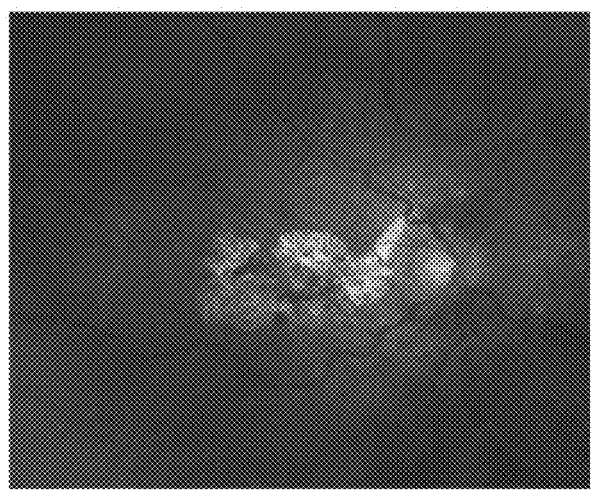

FIG. 16A
FIG. 16B
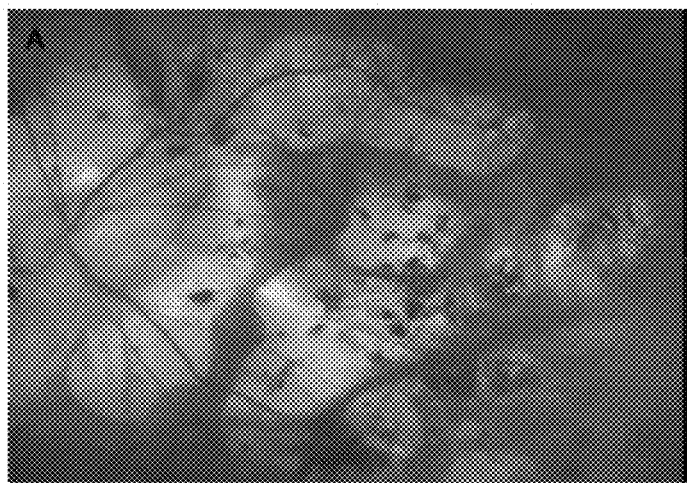
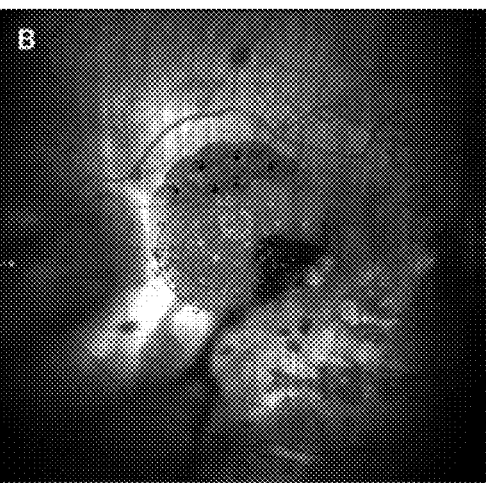
FIG. 16C
FIG. 16D
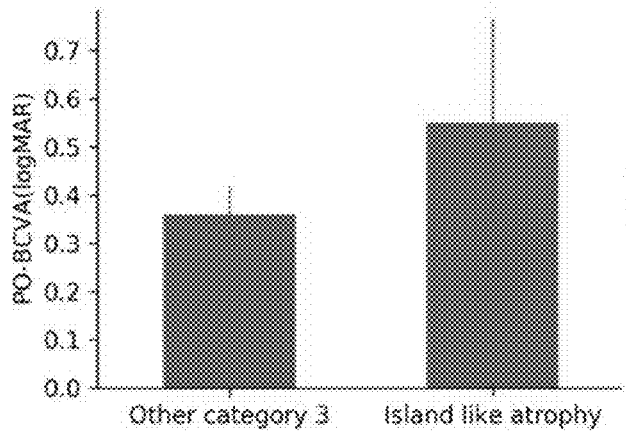
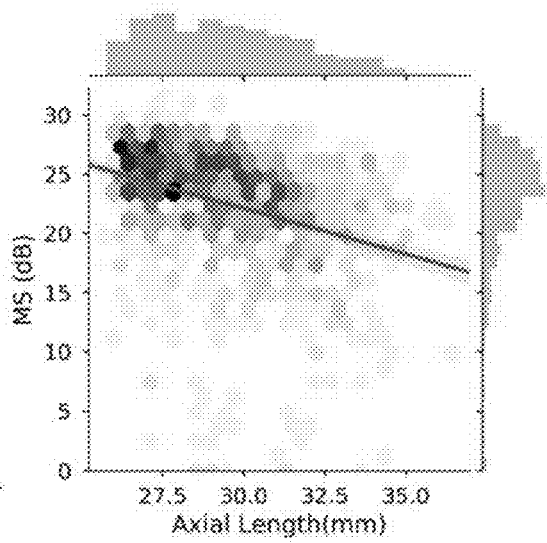

FIG. 18A
FIG. 18B
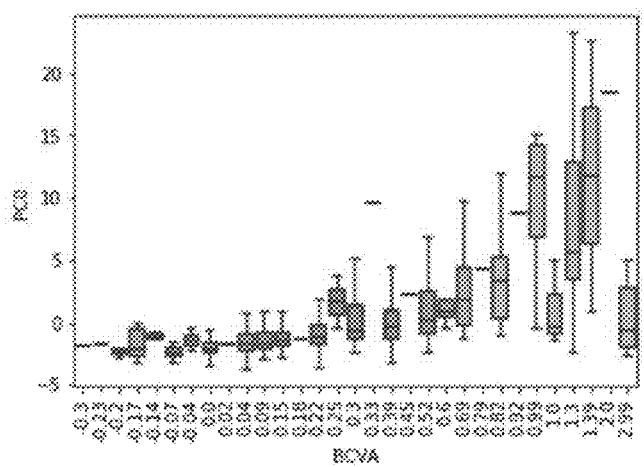
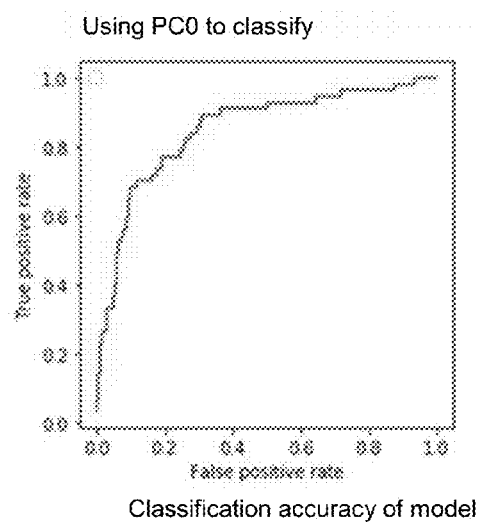
FIG. 18C
FIG. 18D
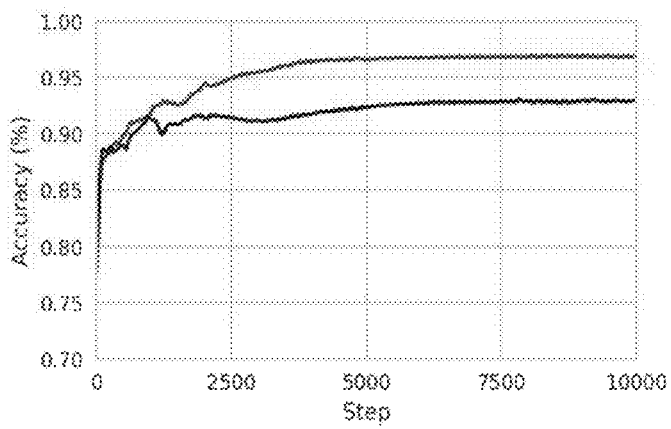
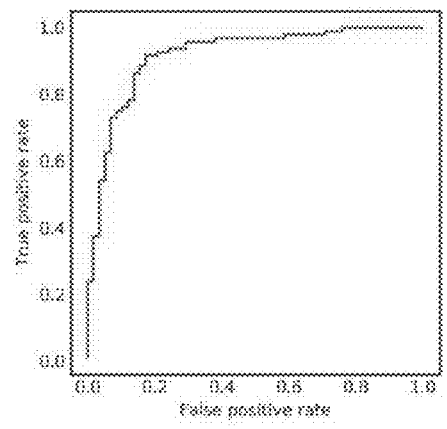

DEEP LEARNING-BASED DIAGNOSIS AND REFERRAL OF OPHTHALMIC DISEASES AND DISORDERS

CROSS-REFERENCE

This application claims the benefit of U.S. Provisional Application No. 62/572,384, filed Oct. 13, 2017, U.S. Provisional Application No. 62/668,698, filed May 8, 2018, and U.S. Provisional Application No. 62/694,939, filed Jul. 6, 2018, which each of the applications is incorporated herein by reference in its entirety.

BACKGROUND OF THE DISCLOSURE

Many ophthalmic diseases and disorders are diagnosed based on medical imaging, such as for example retinal imaging. Medical imaging has traditionally relied upon human experts to analyze images individually. As the number of medical imaging procedures increase, demand for efficient and accurate image analysis is outstripping the supply of experts capable of performing this function.

SUMMARY OF THE DISCLOSURE

Traditional algorithmic approaches to medical image analysis suffer from numerous technical deficiencies related to an inability to adequately perform the analysis without significant human intervention and/or guidance, which belies the supposed promise of artificial intelligence and machine learning to revolutionize disease diagnosis and management. For example, one approach relies upon (1) handcrafted object segmentation, (2) identification of each segmented object using statistical classifiers or shallow neural computational machine-learning classifiers designed specifically for each class of objects, and (3) classification of the image. As a result, the creation and refinement of multiple classifiers required considerable expertise and time, and was computationally expensive. In addition, the training of machine learning classifiers is often deficient due to a lack of sufficient medical images in the training set. This problem is exacerbated in the case of diseases or conditions that are relatively rare or lack adequate access to the medical images. Moreover, because machine learning often behaves like a black box, acceptance of diagnoses generated through such methods can be hindered due to the lack of transparency on how the classifier evaluates a medical image to generate a prediction.

The present disclosure solves these technical problems with existing computer systems carrying out image analysis by providing improved systems and techniques that do not require substantial intervention by an expert to generate the classifiers. These include, for example, convolutional neural network layers that provide multiple processing layers to which image analysis filters or convolutions are applied. The abstracted representation of images within each layer is constructed by systematically convolving multiple filters across the image to produce a feature map used as input for the following layer. This overall architecture enables images to be processed into pixels as input and to generate the desired classification as output. Accordingly, the multiple resource-intensive steps used in traditional image analysis techniques such as handcrafted object segmentation, identification of the segmented objects using a shallow classifier, and classification of the image is no longer required.

In addition, the present disclosure solves the technical problem of insufficient images in the relevant domain (e.g. medical images for a specific ophthalmic disease) for training algorithms to effectively perform image analysis and/or diagnosis. Certain embodiments of the present disclosure include systems and techniques applying a transfer learning algorithm to train an initial machine learning algorithm such as a convolutional neural network on images outside of the specific domain of interest to optimize the weights in the lower layer(s) for recognizing the structures found in the images. The weights for the lower layer(s) are then frozen, while the weights of the upper layer(s) are retrained using images from the relevant domain to identify output according to the desired diagnosis (e.g. identification or prediction of specific ophthalmic diseases or conditions). This approach allows the classifier to recognize distinguishing features of specific categories of images (e.g. images of the eye) far more quickly using significantly fewer training images and while requiring substantially less computational power. The use of non-domain images to partially train or pre-train the classifier allows optimization of the weights of one or more of the neural network layers using a deep reservoir of available images corresponding to thousands of categories. The result is a classifier having a sensitivity, specificity, and accuracy that is unexpected and surprising compared to the traditional approach, especially in view of the improvements in speed, efficiency, and computational power required. Indeed, certain embodiments of the classifier outperform human experts in correctly diagnosing medical images according to sensitivity, specificity, accuracy, or a combination thereof.

The present disclosure also addresses the black box nature of machine learning by allowing identification of the critical areas contributing most to the classifier's predicted diagnosis. Certain embodiments of the present disclosure utilize occlusion testing on test images to identify the regions of interest that contribute the highest importance to the classifier's ability to generate accurate diagnoses. These regions can be verified by experts to validate the system, which creates greater transparent and increases trust in the diagnosis.

The technological solutions to the technological problem of effectively implementing computer-based algorithmic image analysis described herein opens up the previously unrealized potential of machine learning techniques to revolutionize medical image analysis and diagnosis. Furthermore, the present disclosure provides additional technical advantages over existing computer systems and techniques that are described in more detail below.

In certain embodiments, the present disclosure relates to a method for providing an ophthalmic diagnosis, the method comprises: obtaining a medical image; performing a machine learning procedure on the medical image; and determining, by the machine learning procedure, whether or not the medical image is indicative of a disease or disorder, the determination having a sensitivity greater than 90% and a specificity greater than 90%. In some non-limiting embodiments, the machine learning procedure comprises a deep learning procedure. In some non-limiting embodiments, the machine learning procedure comprises a convolutional neural network. In some non-limiting embodiments, the method further comprises subjecting the medical image to an image occlusion procedure. In some non-limiting embodiments, the method further comprises performing a transfer learning procedure. In some non-limiting embodiments, the transfer learning procedure comprises pre-training the machine learning procedure using non-medical images obtained from a large image dataset to obtain a pre-trained machine learning procedure. In some non-limiting embodiments, the transfer learning procedure further comprises training the pre-trained machine learning procedure using a set of medical images that is smaller than the large image dataset. In some non-limiting embodiments, the method further comprises making a medical treatment recommendation based on the determination. In some non-limiting embodiments, the medical image is an ophthalmic image that conveys information about the presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the medical disorder is selected from the group consisting of: age-related macular degeneration (AMD), diabetic macular edema (DME), and choroidal neovascularization (CNV).

In certain embodiments, the present disclosure relates to a non-transitory computer-readable medium comprising machine-executable code that, upon execution by one or more computer processors, implements a method for providing an ophthalmic diagnosis, the method comprises: obtaining a medical image; performing a machine learning procedure on the medical image; and determining, by the machine learning procedure, whether or not the medical image is indicative of a disease or disorder, the determination having a sensitivity greater than 90% and a specificity greater than 90%. In some non-limiting embodiments, the machine learning procedure comprises a deep learning procedure. In some non-limiting embodiments, the machine learning procedure comprises a convolutional neural network. In some non-limiting embodiments, the method further comprises subjecting the medical image to an image occlusion procedure. In some non-limiting embodiments, the method further comprises performing a transfer learning procedure. In some non-limiting embodiments, the transfer learning procedure comprises pre-training the machine learning procedure using non-medical images obtained from a large image dataset to obtain a pre-trained machine learning procedure. In some non-limiting embodiments, the transfer learning procedure further comprises training the pre-trained machine learning procedure using a set of medical images that is smaller than the large image dataset. In some non-limiting embodiments, the method further comprises making a medical treatment recommendation based on the determination. In some non-limiting embodiments, the medical image is an ophthalmic image that conveys information about the presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the medical disorder is selected from the group consisting of: age-related macular degeneration (AMD), diabetic macular edema (DME), and choroidal neovascularization (CNV).

In certain embodiments, the present disclosure relates to a computer-implemented system comprising: a digital processing device comprising: at least one processor, an operating system configured to perform executable instructions, a memory, and a computer program including instructions executable by the digital processing device to create an application for providing, a medical diagnosis, the application comprising: a software module for obtaining a medical image; a software module for performing a machine learning procedure on the medical image; and a software module for determining, by the machine learning procedure, whether or not the medical image is indicative of a medical disease or disorder, the determination having a sensitivity greater than 90% and a specificity greater than 90%. In some non-limiting embodiments, the machine learning procedure comprises a deep learning procedure. In some non-limiting embodiments, the machine learning procedure comprises a convolutional neural network. In some non-limiting embodiments, the application further comprises a software module for subjecting the medical image to an image occlusion procedure. In some non-limiting embodiments, the application further comprises a software module for performing a transfer learning procedure. In some non-limiting embodiments, the transfer learning procedure comprises pre-training the machine learning procedure using non-medical images obtained from a large image dataset to obtain a pre-trained machine learning procedure. In some non-limiting embodiments, the transfer learning procedure further comprises training the pre-trained machine learning procedure using a set of medical images that is smaller than the large image dataset. In some non-limiting embodiments, the application further comprises a software module for making a medical treatment recommendation based on the determination. In some non-limiting embodiments, the medical image is an ophthalmic image that conveys information about the presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the medical disorder is selected from the group consisting of: age-related macular degeneration (AMD), diabetic macular edema (DME), and choroidal neovascularization (CNV).

In certain embodiments, the present disclosure relates to a method for providing a medical diagnosis, comprising: a) obtaining a medical image; b) analyzing the medical image with a machine learning procedure; and c) generating, by the machine learning procedure, a prediction of visual acuity based on the medical image, the prediction having a sensitivity greater than 90% and a specificity greater than 90%. In some non-limiting embodiments, the machine learning procedure comprises a deep learning procedure. In some non-limiting embodiments, the machine learning procedure comprises training a convolutional neural network. In some non-limiting embodiments, the convolutional neural network has no more than 5 neurons per layer. In some non-limiting embodiments, the machine learning procedure utilizes inputs comprising age, axial length, and macular sensitivity. In some non-limiting embodiments, the method further comprises making a medical treatment recommendation based on the determination. In some non-limiting embodiments, the medical image is an ophthalmic image that conveys information about the presence or absence of an ophthalmic disease, disorder, or condition. In some non-limiting embodiments, the ophthalmic image is an optical coherence tomography (OCT) image. In some non-limiting embodiments, the ophthalmic image is a macular sensitivity threshold image. In some non-limiting embodiments, the ophthalmic disease, disorder, or condition is selected from the group consisting of: age-related macular degeneration (AMD), diabetic macular edema (DME), choroidal neovascularization (CNV), chorioretinal atrophy, foveoschisis, intra-operative vitreous loss, postoperative retinal tear or detachment, and posterior staphyloma.

In certain embodiments, the present disclosure relates to a non-transitory computer-readable medium comprising machine-executable code that, upon execution by one or more computer processors, implements a method for providing a medical diagnosis, the method comprising: b)

obtaining a medical image; b) analyzing the medical image with a machine learning procedure; and c) generating, by the machine learning procedure, a prediction of visual acuity based on the medical image, the prediction having a sensitivity greater than 90% and a specificity greater than 90%. In some non-limiting embodiments, the machine learning procedure comprises a deep learning procedure. In some non-limiting embodiments, the machine learning procedure comprises training a convolutional neural network. In some non-limiting embodiments, the convolutional neural network has no more than 5 neurons per layer. In some non-limiting embodiments, the machine learning procedure utilizes inputs comprising age, axial length, and macular sensitivity. In some non-limiting embodiments, the method further comprises making a medical treatment recommendation based on the prediction. In some non-limiting embodiments, the medical image is an ophthalmic image that conveys information about the presence or absence of an ophthalmic disease, disorder, or condition. In some non-limiting embodiments, the ophthalmic image is a retinal image. In some non-limiting embodiments, the ophthalmic image is an optical coherence tomography (OCT) image. In some non-limiting embodiments, the ophthalmic image is a macular sensitivity threshold image. In some non-limiting embodiments, the ophthalmic disease, disorder, or condition is selected from the group consisting of: age-related macular degeneration (AMD), diabetic macular edema (DME), choroidal neovascularization (CNV), chorioretinal atrophy, foveoschisis, intra-operative vitreous loss, postoperative retinal tear or detachment, and posterior staphyloma.

In certain embodiments, the present disclosure relates to a computer-implemented system comprising: a digital processing device comprising: at least one processor, an operating system configured to perform executable instructions, a memory, and a computer program including instructions executable by the digital processing device to create an application for providing a medical diagnosis, the application comprising: a) a software module obtaining a medical image; b) a software module analyzing the medical image with a machine learning procedure; and c) a software module using a machine learning procedure to generate a prediction of visual acuity based on the medical image, the prediction having a sensitivity greater than 90% and a specificity greater than 90%. In some non-limiting embodiments, the machine learning procedure comprises a deep learning procedure. In some non-limiting embodiments, the machine learning procedure comprises training a convolutional neural network. In some non-limiting embodiments, the convolutional neural network has no more than 5 neurons per layer. In some non-limiting embodiments, the machine learning procedure utilizes inputs comprising age, axial length, and macular sensitivity. In some non-limiting embodiments, the application further comprises a software module for making a medical treatment recommendation based on the determination. In some non-limiting embodiments, the medical image is an ophthalmic image that conveys information about the presence or absence of an ophthalmic disease, disorder, or condition. In some non-limiting embodiments, the ophthalmic image is a retinal image. In some non-limiting embodiments, the ophthalmic image is an optical coherence tomography (OCT) image. In some non-limiting embodiments, the ophthalmic disease or disorder is selected from the group consisting of: age-related macular degeneration (AMD), diabetic macular edema (DME), choroidal neovascularization (CNV), chorioretinal atrophy, foveoschisis, intra-operative vitreous loss, postoperative retinal tear or detachment, and posterior staphyloma.

In certain embodiments, the present disclosure relates to a computer-implemented method for providing a medical diagnosis, comprising: a) obtaining medical data for an individual; b) performing a machine learning procedure on the medical data; and c) generating, by the machine learning procedure, a prediction of visual acuity or a visual disorder or condition based on the medical data, the prediction having a sensitivity greater than 90% and a specificity greater than 90%. In some non-limiting embodiments, the medical data comprises inputs associated with myopia that are processed by the machine learning procedure to generate the prediction of visual acuity. In some non-limiting embodiments, the medical data comprises a medical image. In some non-limiting embodiments, the medical image is an image of a fundus overlaid with microperimetry results. In some non-limiting embodiments, the medical data comprises at least one measure of myopia. In some non-limiting embodiments, the medical data comprises age, axial length, macular sensitivity image, or any combination thereof. In some non-limiting embodiments, the prediction comprises a predicted visual acuity for the individual after cataract surgery. In some non-limiting embodiments, the prediction comprises a diagnostic of good or poor visual acuity for the individual following cataract surgery. In some non-limiting embodiments, the machine learning procedure comprises a deep learning procedure. In some non-limiting embodiments, the machine learning procedure comprises training a convolutional neural network. In some non-limiting embodiments, the transfer learning procedure is trained using a dataset comprising medical images classified into categories of myopic maculopathy. In some non-limiting embodiments, the method further comprises making a medical treatment recommendation based on the prediction. In some non-limiting embodiments, the medical image is an ophthalmic image that conveys information about the presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the ophthalmic disease or disorder is selected from the group consisting of: age-related macular degeneration (AMD), diabetic macular edema (DME), and choroidal neovascularization (CNV). In some non-limiting embodiments, the prediction comprises a best corrected visual acuity (BCVA). In some non-limiting embodiments, the machine learning procedure comprises training a machine learning algorithm using outcome classified patient data comprising macular sensitivity, axial length, best corrected visual acuity (BCVA), bivariate contour ellipse area (BCEA), or any combination hereof. In some non-limiting embodiments, the patient data is classified according to at least four categories of myopic maculopathy.

In certain embodiments, the present disclosure relates to a non-transitory computer-readable medium comprising machine-executable code that, upon execution by one or more computer processors, implements a method for providing a medical diagnosis, the method comprising: a) obtaining medical data for an individual; b) performing a machine learning procedure on the medical data; and c) generating, by the machine learning procedure, a prediction of visual acuity or a medical disease or disorder, the prediction having a sensitivity greater than 90% and a specificity greater than 90%. In some non-limiting embodiments, the medical data comprises inputs associated with myopia that are processed by the machine learning procedure to generate the prediction of visual acuity. In some non-limiting embodiments, the medical data comprises a medical image. In some non-limiting embodiments, the medical image is an image of a fundus overlaid with microperimetry results. In some non-limiting embodiments, the medical data comprises at least one measure of myopia. In some non-limiting embodiments, the medical data comprises age, axial length, macular sensitivity image, or any combination thereof. In some non-limiting embodiments, the prediction comprises a predicted visual acuity for the individual after cataract surgery. In some non-limiting embodiments, the prediction comprises a diagnostic of good or poor visual acuity for the individual following cataract surgery. In some non-limiting embodiments, the machine learning procedure comprises a deep learning procedure. In some non-limiting embodiments, the machine learning procedure comprises training a convolutional neural network. In some non-limiting embodiments, the transfer learning procedure is trained using a dataset comprising medical images classified into categories of myopic maculopathy. In some non-limiting embodiments, wherein the method further comprises making a medical treatment recommendation based on the prediction. In some non-limiting embodiments, the medical image is an ophthalmic image that conveys information about the presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the ophthalmic disease or disorder is selected from the group consisting of: age-related macular degeneration (AMD), diabetic macular edema (DME), and choroidal neovascularization (CNV). In some non-limiting embodiments, the prediction comprises a best corrected visual acuity (BCVA). In some non-limiting embodiments, the machine learning procedure comprises training a machine learning algorithm using outcome classified patient data comprising macular sensitivity, axial length, best corrected visual acuity (BCVA), bivariate contour ellipse area (BCEA), or any combination hereof. In some non-limiting embodiments, the patient data is classified according to at least four categories of myopic maculopathy.

In certain embodiments, the present disclosure relates to a computer-implemented system comprising: a digital processing device comprising: at least one processor, an operating system configured to perform executable instructions, a memory, and a computer program including instructions executable by the digital processing device to create an application for providing a medical diagnosis, the application comprising: a) a software module for obtaining medical data for an individual; b) a software module for performing a machine learning procedure on the medical data; and c) a software module for generating, by the machine learning procedure, a prediction of visual acuity or a medical disease or disorder, the prediction having a sensitivity greater than 90% and a specificity greater than 90%. In some non-limiting embodiments, the medical data comprises inputs associated with myopia that are processed by the machine learning procedure to generate the prediction of visual acuity. In some non-limiting embodiments, the medical data comprises a medical image. In some non-limiting embodiments, the medical image is an image of a fundus overlaid with microperimetry results. In some non-limiting embodiments, the medical data comprises at least one measure of myopia. In some non-limiting embodiments, the medical data comprises age, axial length, macular sensitivity image, or any combination thereof. In some non-limiting embodiments, the prediction comprises a predicted visual acuity for the individual after cataract surgery. In some non-limiting embodiments, the prediction comprises a diagnostic of good or poor visual acuity for the individual following cataract surgery. In some non-limiting embodiments, the machine learning procedure comprises a deep learning procedure. In some non-limiting embodiments, the machine learning procedure comprises training a convolutional neural network. In some non-limiting embodiments, the transfer learning procedure is trained using a dataset comprising medical images classified into categories of myopic maculopathy. In some non-limiting embodiments, the method further comprises making a medical treatment recommendation based on the prediction. In some non-limiting embodiments, the medical image is an ophthalmic image that conveys information about the presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the ophthalmic disease or disorder is selected from the group consisting of: age-related macular degeneration (AMD), diabetic macular edema (DME), and choroidal neovascularization (CNV). In some non-limiting embodiments, the prediction comprises a best corrected visual acuity (BCVA). In some non-limiting embodiments, the machine learning procedure comprises training a machine learning algorithm using outcome classified patient data comprising macular sensitivity, axial length, best corrected visual acuity (BCVA), bivariate contour ellipse area (BCEA), or any combination hereof. In some non-limiting embodiments, the patient data is classified according to at least four categories of myopic maculopathy.

In certain embodiments, the present disclosure relates to a computer-implemented system comprising: a) an electronic device comprising: a processor, a memory, a display, a camera, and an operating system configured to perform executable instructions; b) a portable device comprising an imaging component, said portable device configured to receive and position the electronic device to align the camera with the imaging component; and c) a computer program stored in the memory of the electronic device, the computer program including instructions executable by the user electronic device to create an application comprising: i) a software module controlling the camera to capture an ophthalmic image or video of a subject; and ii) a software module determining whether the ophthalmic image or video is indicative of a medical disease or disorder, the determination having a sensitivity greater than 90% and a specificity greater than 90%. In some non-limiting embodiments, determining whether the ophthalmic image or video is indicative of a medical disease or disorder comprises uploading the ophthalmic image or video to a cloud network to be analyzed by a trained classifier generated using a machine learning procedure. In some non-limiting embodiments, determining whether the ophthalmic image or video is indicative of a medical disease or disorder comprises analyzing the ophthalmic image or video with a classifier generated using a machine learning procedure. In some non-limiting embodiments, the machine learning procedure comprises a deep learning procedure. In some non-limiting embodiments, the machine learning procedure comprises training a convolutional neural network. In some non-limiting embodiments, the application further comprises a software module displaying the determination. In some non-limiting embodiments, the application further comprises a software module subjecting the ophthalmic image or video to an image occlusion procedure. In some non-limiting embodiments, the software module displaying the determination further displays areas of the ophthalmic image or video identified as significant to the determination by the image occlusion procedure. In some non-limiting embodiments, the machine learning procedure further comprises a transfer learning procedure. In some non-limiting embodiments, the transfer learning procedure comprises pre-training an untrained classifier using non-medical images obtained from a large image dataset to obtain a pre-trained classifier. In some non-limiting embodiments, the transfer learning procedure further comprises training the pre-trained classifier using a set of medical images that is smaller than the large image dataset to obtain the trained classifier. In some non-limiting embodiments, the application further comprises a software module making a medical treatment recommendation based on the determination. In some non-limiting embodiments, the ophthalmic image or video conveys information about a presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the ophthalmic disease or disorder is selected from the group consisting of: age-related macular degeneration (AMD), diabetic macular edema (DME), and choroidal neovascularization (CNV). In some non-limiting embodiments, the imaging component is an ophthalmoscope enabling the camera to capture the ophthalmic image or video from an eye of a subject. In some non-limiting embodiments, the portable device comprises an adaptor configured to receive and position the electronic device. In some non-limiting embodiments, the system further comprises a network server receiving the ophthalmic image or video uploaded by the electronic device, analyzing the ophthalmic image or video with a trained classifier to obtain the determination, and providing the determination to the electronic device. In some non-limiting embodiments, the application further comprises a software module stitching together screenshots of the ophthalmic video to generate a composite ophthalmic image.

In certain embodiments, the present disclosure relates to a computer-implemented system comprising: a) a medical imaging device configured to capture an ophthalmic image of a subject; b) an electronic device operatively coupled to the medical imaging device, comprising: a processor, a memory, a display, and an operating system configured to perform executable instructions; c) a computer program stored in the memory of the electronic device, the computer program including instructions executable by the user electronic device to create an application comprising: i) a software module controlling the medical imaging device to capture the ophthalmic image of the subject; and ii) a software module determining whether the ophthalmic image is indicative of a medical disease or disorder, the determination having a sensitivity greater than 90% and a specificity greater than 90%. In some non-limiting embodiments, determining whether the ophthalmic image is indicative of a medical disease or disorder comprises uploading the ophthalmic image to a cloud network to be analyzed by a trained classifier generated using a machine learning procedure. In some non-limiting embodiments, determining whether the ophthalmic image is indicative of a medical disease or disorder comprises analyzing the ophthalmic image with a classifier generated using a machine learning procedure. In some non-limiting embodiments, the machine learning procedure comprises a deep learning procedure. In some non-limiting embodiments, the machine learning procedure comprises training a convolutional neural network. In some non-limiting embodiments, the application further comprises a software module displaying the determination. In some non-limiting embodiments, the application further comprises a software module subjecting the ophthalmic image or video to an image occlusion procedure. In some non-limiting embodiments, the software module displaying the determination further displays areas of the ophthalmic image identified as significant to the determination by the image occlusion procedure. In some non-limiting embodiments, the machine learning procedure further comprises a transfer learning procedure. In some non-limiting embodiments, the transfer learning procedure comprises pre-training an untrained classifier using non-medical images obtained from a large image dataset to obtain a pre-trained classifier. In some non-limiting embodiments, the transfer learning procedure further comprises training the pre-trained classifier using a set of medical images that is smaller than the large image dataset to obtain the trained classifier. In some non-limiting embodiments, the application further comprises a software module making a medical treatment recommendation based on the determination. In some non-limiting embodiments, the ophthalmic image conveys information about a presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the ophthalmic disease or disorder is selected from the group consisting of: age-related macular degeneration (AMD), diabetic macular edema (DME), and choroidal neovascularization (CNV). In some non-limiting embodiments, the medical imaging device is an optical coherence tomography (OCT) device. In some non-limiting embodiments, wherein the system further comprises a network server receiving the ophthalmic image uploaded by the electronic device, analyzing the ophthalmic image or video with a trained classifier to obtain the determination, and providing the determination to the electronic device. In some non-limiting embodiments, the system is configured as a self-service kiosk. In some non-limiting embodiments, the kiosk comprises a positioning component for positioning a head of a subject in front of the medical imaging device to capture the ophthalmic image. In some non-limiting embodiments, the positioning component is configured to reduce or minimize head tilt by the subject. In some non-limiting embodiments, the kiosk further comprises a microphone and a speaker, and is configured to provide teleconferencing with a remote healthcare provider to discuss the determination and optionally a treatment recommendation. In some non-limiting embodiments, the kiosk comprises an interface for receiving payment information. In some non-limiting embodiments, the interface comprises a card reader, a scanner, an RFID system, a cash acceptor, a touchscreen for entering payment information, or a combination thereof.

In certain embodiments, the present disclosure relates to a computing system comprising at least one processor, a memory, and non-transitory computer readable storage media encoded with a program including instructions executable by the at least one processor to create a web application comprising: a) a software module receiving a medical image uploaded by an electronic device over a network; b) a software module analyzing the ophthalmic image with a trained classifier to determine whether the ophthalmic image is indicative of a medical disease or disorder, the determination having a sensitivity greater than 90% and a specificity greater than 90%; and c) a software module sending the determination to the electronic device.

In some non-limiting embodiments, the trained classifier is generated through a machine learning procedure. In some non-limiting embodiments, the machine learning procedure comprises a deep learning procedure. In some non-limiting embodiments, the machine learning procedure comprises training a convolutional neural network. In some non-limiting embodiments, the application further comprises a software module subjecting the ophthalmic image to an image occlusion procedure. In some non-limiting embodiments, the application further comprises a software module sending the ophthalmic image to the electronic device, wherein the areas of the ophthalmic image identified as significant to the determination by the image occlusion procedure are visually accentuated. In some non-limiting embodiments, the machine learning procedure further comprises a transfer learning procedure. In some non-limiting embodiments, the transfer learning procedure comprises pre-training an untrained classifier using non-medical images obtained from a large image dataset to obtain a pre-trained classifier. In some non-limiting embodiments, the transfer learning procedure further comprises training the pre-trained classifier using a set of medical images that is smaller than the large image dataset to obtain the trained classifier. In some non-limiting embodiments, the application further comprises a software module making a medical treatment recommendation based on the determination. In some non-limiting embodiments, the ophthalmic image conveys information about a presence or absence of an ophthalmic disease or disorder. In some non-limiting embodiments, the ophthalmic image is a retinal image. In some non-limiting embodiments, the ophthalmic image is an optical coherence tomography (OCT) image. In some non-limiting embodiments, the ophthalmic disease or disorder is selected from the group consisting of: age-related macular degeneration (AMD), diabetic macular edema (DME), and choroidal neovascularization (CNV). In some non-limiting embodiments, the system is a server integrated into a cloud network.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or applications file contains at least one drawing executed in color. Copies of this patent or patent application publication with color drawing(s) will be provided by the office upon request and payment of the necessary fee.

A better understanding of the features and advantages of the present invention will be obtained by reference to the following detailed description that sets forth illustrative embodiments, in which the principles of the invention are utilized, and the accompanying drawings of which:

FIG. 4A-C shows multi-class comparison between CNV, DME, drusen, and normal.

FIG. 4A shows receiver operating characteristic curve for "urgent referrals" (Choroidal Neovascularization (CNV) and Diabetic Macular Edema (DME) detection) with human expert performance for comparison. FIG. 4B shows a confusion table of best model's classification of the validation image set. FIG. 4C shows weighted error results based on penalties shown in FIG. 10A depicting neural networks in gold and human experts in blue.

FIG. 5A shows the plot, created using TensorBoard, represents the training (orange) and validation (blue) accuracies during training of the multi-class classifier over the course of 10,000 steps.

FIG. 5B shows the plot representing cross entropy loss during the training. The plot was normalized with a smoothing factor of 0.6 in order to clearly visualize trends.

FIG. 7A-C shows the binary performance in the training and validation datasets using TensorBoard. Comparisons were made for choroidal neovascularization (CNV) versus normal (FIG. 7A), diabetic macular edema (DME) versus normal (FIG. 7B), and drusen versus normal (FIG. 7C).

FIG. 8A-C shows the receiver operating characteristic curves for binary classifiers for choroidal neovascularization (CNV) versus normal (FIG. 8A), diabetic macular edema (DME) versus normal (FIG. 8B), and drusen versus normal (FIG. 8C).

FIG. 10A shows the proposed penalties for incorrect labeling during weighted error calculations and confusion matrix of experts grading OCT images.

FIG. 10B shows the results comparing the true labels and predicted labels for individual human experts.

FIG. 11A-F shows horizontal cross-section OCT images through the fovea of patients with wet AMD (A-C) or diabetic retinopathy (D-F) with macular edema: before (left) and after (right) three monthly intravitreal injections of bevacizumab. The visual acuity (VA) of all patients was assessed: (FIG. 11A) 20/320 to 20/250, 5 months. (FIG. 11B) 20/40 to 20/32, 9 months, (FIG. 11C) 20/400 to 20/250, 3 months, (FIG. 11D) 20/80 to 20/50, 7 months, (FIG. 11E) 20/40 to 20/25, 7 months, and (FIG. 11F) 20/32 to 20/25, 7 months. (FIG. 11G) Pre-treatment horizontal cross-section OCT images (up, left) of DME patient's left eye showed macular edema (arrows) through macular center and the intra-retinal fluid disappeared after three consecutive anti-VEGF treatment (up, right).

FIG. 14A shows postoperative visual outcomes in all adult cataract cases comparing high myopic cataract and age related cataract patients. FIG. 14B shows postoperative visual outcomes comparing axial length.

FIG. 15A-D shows examples of fundus images grading. Fundus images of patients showing myopic maculopathy of different disease categories compared with the existing International Photographic Classification and Grading System for myopic maculopathy: category 1, tessellated fundus (FIG. 15A); category 2, diffuse chorioretinal atrophy (FIG. 15B); category 3, patchy chorioretinal atrophy (FIG. 15C); category 4, macular atrophy (FIG. 15D).

FIG. 16A-F evaluates patients with the island-like macular atrophy pattern and their post-operative visual outcome (FIG. 16A-C) and correlations of macular sensitivity, axial length and BCEA among all patients (FIG. 16D-F). FIG. 16A shows an ultra-widefield retinal image showing island-like macular atrophy. FIG. 16B shows a microperimeter image including the fixation BCEA and mean macular sensitivity. FIG. 16C shows postoperative visual outcomes among all the patients in category 3. FIG. 16D shows correlations between MS and axial length.

FIG. 16E shows correlations between MS and BCEA. FIG. 16F shows correlations between BCEA and axial length.

FIG. 18A-C shows plots showing performance of a deep learning model. FIG. 18A shows first principal component (PC0) of macular sensitivity images. FIG. 18B shows PC0 of threshold image to classify patients' post-op BCVA(log MAR). FIG. 18C shows tracking accuracy (y-axis) changes of neural net in both training and testing cohort with respect to number of training steps (x-axis). FIG. 18D shows classification accuracy of model in validation cohort using the trained hierarchical neural network.

FIG. 19A shows the growth differentiation factor-15 (GDF-15) level in aqueous humor was positively correlated with axial length. FIG. 19B shows the hepatocyte growth factor (HGF) level in aqueous humor was positively correlated with axial length. FIG. 19C shows the platelet derived growth factor (PDGF-AA) level in aqueous humor was positively correlated with axial length. FIG. 19D shows the vascular endothelial growth factor (VEGF) level in aqueous humor was negatively correlated with axial length.

FIG. 20A shows the standard curve for GDF-15. FIG. 20B shows the standard curve for HGF. FIG. 20C shows the standard curve for PDGF-AA.

DETAILED DESCRIPTION OF THE DISCLOSURE

Figure 1:
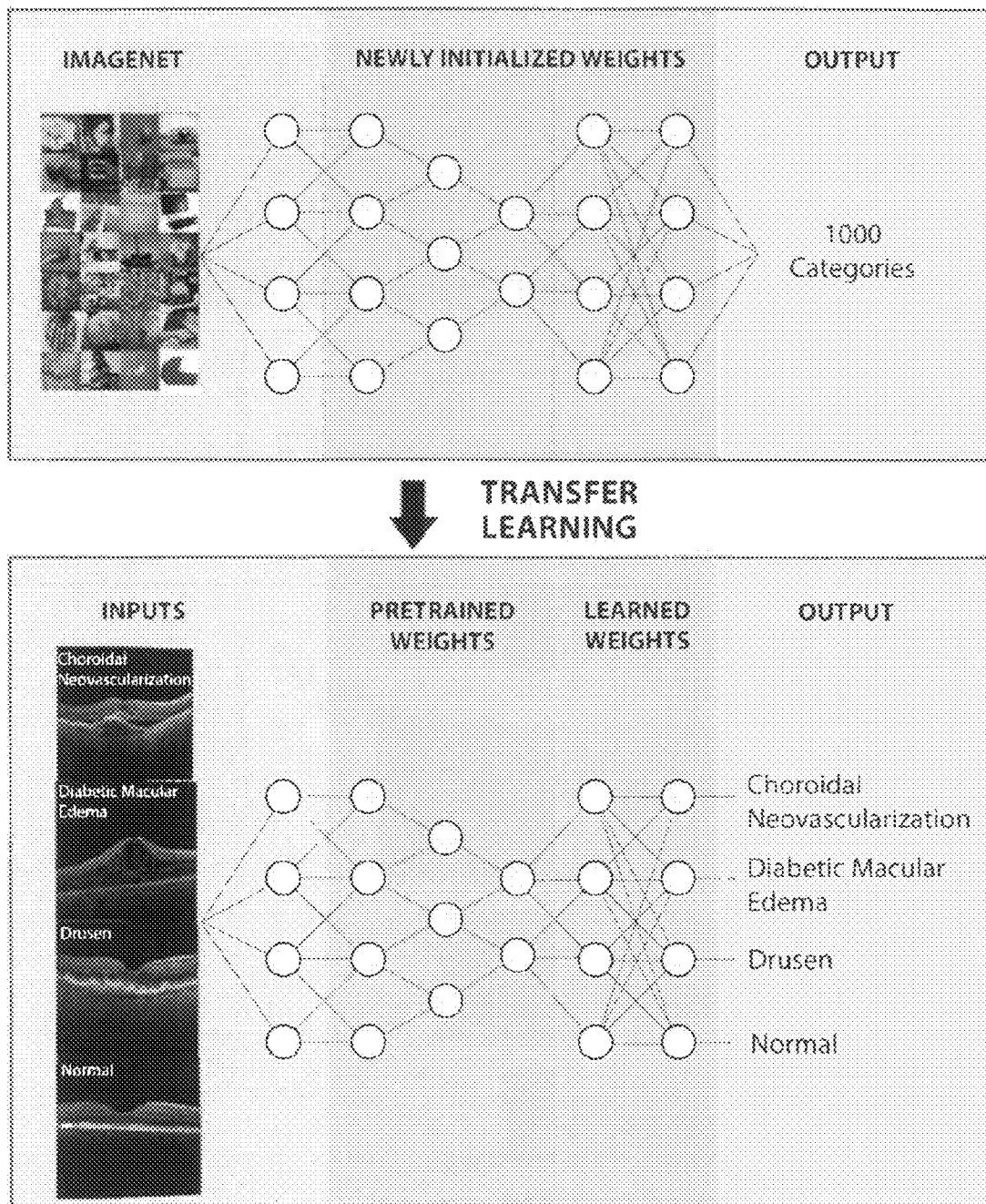
FIG. 1 shows a schematic of a convolutional neural network and how it can be trained on a dataset of 1,000 categories to increase the accuracy and shorten the training duration of a network trained on a novel dataset of OCT images.

It is recognized that implementation of clinical decision support algorithms for medical imaging with improved reliability and clinical interpretability can be achieved through one or combinations of technical features of the present disclosure. According to some aspects, disclosed herein is a diagnostic tool to correctly identify eye-related issues by presenting a machine learning framework developed for ophthalmic diseases or conditions such as common and treatable blinding retinal diseases. In some embodiments, the machine learning framework utilizes deep learning models such as artificial neural networks. Certain embodiments of the disclosed framework implement a transfer learning algorithm, which allows for the training of a highly accurate neural network with a fraction of the data required in more conventional approaches. In some embodiments, the model disclosed herein generalizes and performs well on many medical classification tasks. This framework can be applied towards medical data such as medical images of the eye to identify or diagnose ophthalmic diseases or conditions. In some instances, multiple imaging modalities are utilized in order to reliably and accurately diagnose various retinal pathologies. Certain embodiments of this approach yield superior performance across many imaging techniques. In some embodiments, the algorithm(s) disclosed herein are implemented on various computing devices. The computing devices include portable communication devices such as smart phones optionally coupled to specialized portable imaging devices, digital processing devices operably coupled to imaging devices, specialized diagnostic devices such as kiosks, and other implementations.

In certain embodiments, this machine learning approach is applied to a large and clinically heterogeneous dataset of OCT (optical coherence tomography) images and is capable of achieving diagnostic performance that is comparable to or superior to that of human experts in classifying ophthalmic diseases or conditions such as age-related macular degeneration (AMD) and diabetic macular edema (DME). In some embodiments, the algorithms disclosed herein provide a more transparent and interpretable diagnosis, compared to traditional deep learning algorithms, by using image occlusion to highlight clinically significant regions within images as understood by the neural network. Furthermore, certain embodiments of the transfer learning approach scales with additional training images and development of clinical imaging datasets as well as with continuing advancements in the field of convolutional neural networks (CNN) and image processing. In some embodiments, provided herein is a platform that interfaces with web and/or mobile applications that upload OCT images for remote diagnosis with high accuracy. The algorithm not only demonstrates strong performance for retinal disease, but also holds broad clinical utility for image-based diagnosis of other diseases.

It is recognized in the present disclosure that Artificial intelligence (AI) has the potential to revolutionize disease diagnosis and healthcare management by performing classification currently difficult for human experts and by rapidly reviewing immense amounts of imaging data. Despite its potential, clinical interpretability and feasible preparation of the AI remain challenging.

Traditional image analysis often relied on handcrafted object segmentation followed by identification of each object with shallow machine learning classifiers designed specifically for each class of objects. Creating and refining multiple classifiers required many skilled people and much time. The multiple steps required of a mature analyzing system to classify an image were computationally expensive. Deep learning networks (DNNs) provide a revolutionary step forward in machine learning technique because DNN classifiers subsume the complex steps that previously needed to be handcrafted to generate a diagnosis from an image. As a result, in various embodiments, a trained DNN classifies a medical image in significantly less time than a human.

In some embodiments, automated recognition systems are developed using a limited amount of image data. With the advent of smartphones and digital cameras, the growth in image data has been exponential. This explosion of data and its widespread availability on the web have led to a need for effective methods for analyzing the huge amount of data efficiently without time-consuming and complex steps. As disclosed herein, DNNs make it possible to analyze the large amount of data currently being generated, and likewise, the large amount of data make it possible for DNNs to be well trained.

As disclosed herein, in certain embodiments, convolutional neural network (CNN) layers allow for significant gains in the ability to classify images and detect objects in a picture. In various embodiments, CNNs are composed of multiple processing layers to which image analysis filters, or convolutions, are applied. In some embodiments, the abstracted representation of images within each layer is constructed by systematically convolving multiple filters across the image, producing a feature map which is used as input to the following layer. CNNs learn representations of images with multiple levels of increasing understanding of the image contents, which is what makes the networks deep. This deep learning method is capable of discovering intricate structures in large data sets by using the backpropagation learning algorithm to change its internal parameters to minimize errors in making the desired classification. Each layer is increasingly sophisticated in its representation of the organization of the data compared to the previous layer. The first few layers of the neural network can extract simple structures, such as lines and edges, while the layers up the chain begin to determine more complex structures. This architecture makes it possible to process images in the form of pixels as input and to give the desired classification as output. Accordingly, in certain embodiments, the image-to-classification approach in one classifier replaces the multiple steps of previous image analysis methods. As a result, the CNNs disclosed herein dramatically improve the state-of-the-art in visual object recognition.

Within ophthalmology, deep learning can be applied at a limited capacity to automated detection of diabetic retinopathy from fundus photos, glaucoma from visual field perimetry, grading of nuclear cataracts, and segmentation of foveal microvasculature, each with promising initial findings. However, the relatively small amount of image data is problematic, as it may be insufficient to train the tens of millions of parameters in a modern DNN.

Figure 2A:
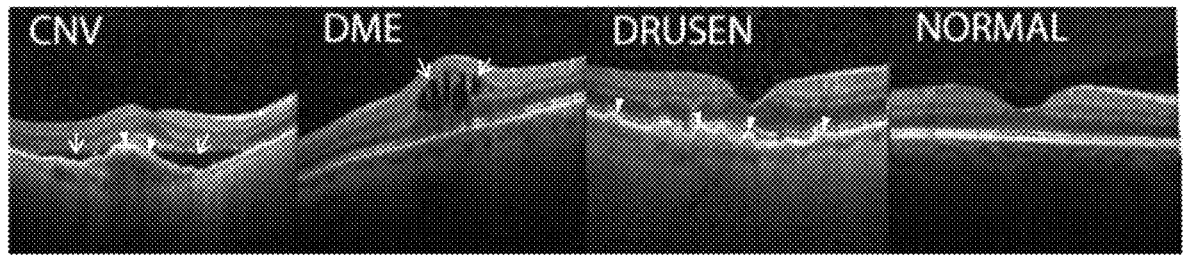
FIG. 2A shows representative optical coherence tomography (OCT) images.
Figure 2B:
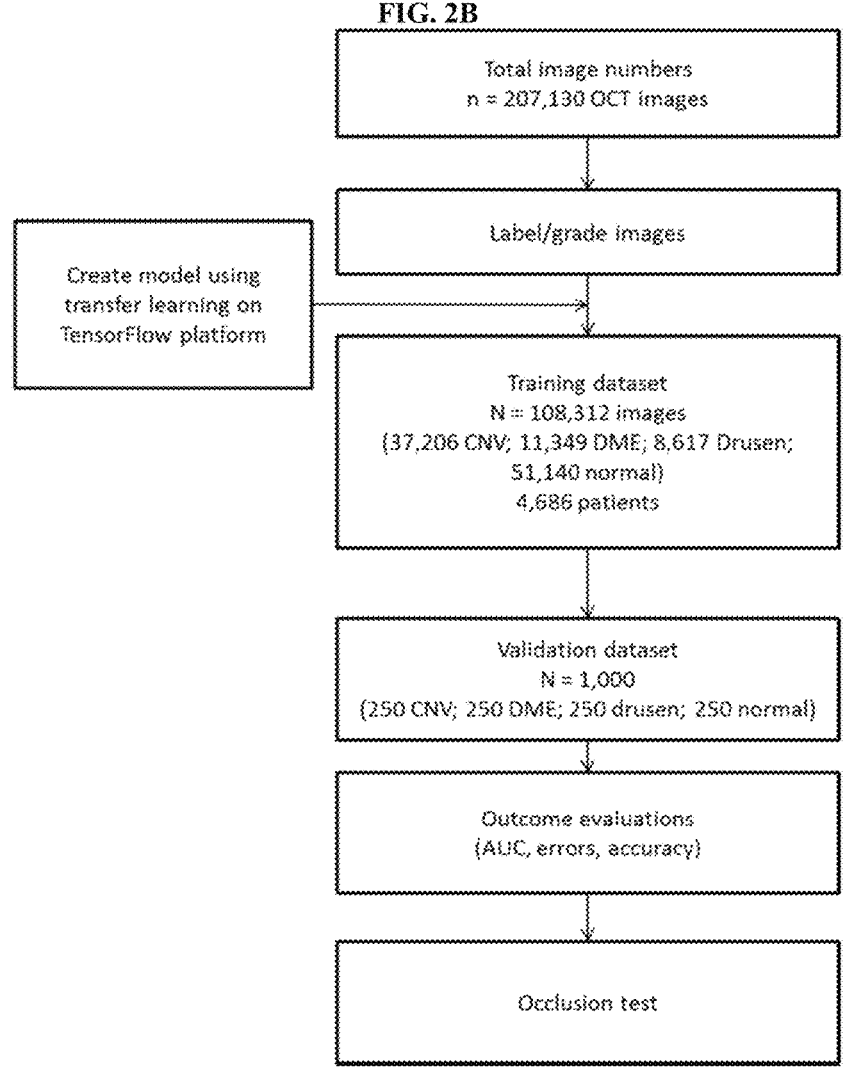
FIG. 2B shows a diagram showing an experimental design describing the flow of optical coherence tomography (OCT) images through the labeling and grading process followed by creation of the transfer learning model, which then underwent training and subsequent testing.

Disclosed herein, in certain aspects, are methods of addressing a lack of data in a given domain by leveraging data from a similar domain. For example, a large database of labeled images has been collected and made available as ImageNet with 1000 object categories. In certain embodiments, a CNN is first trained on this dataset to develop features at its lower layers that are important for discriminating objects. In further embodiments, a second network is created that copies the parameters and structure of the first network, but with the final layer(s) optionally re-structured as needed for a new task (FIG. 1). In certain embodiments, these final layer(s) are configured to perform the classification of retinal images (FIG. 2). Thus, in some embodiments, the second network uses the first network to seed its structure. This allows training to continue on the new, but related task. In some embodiments, the first network is trained using labeled images comprising non-domain images (e.g. images not labeled with the classification), and the second network is trained using labeled images comprising domain images (e.g. classified images) to complete the training allowing for high accuracy diagnosis of ophthalmic disorders and/or conditions. The method of transferring general classification knowledge from one domain to another is called transfer learning. As disclosed herein, the application of transfer learning within the field of machine learning-based diagnosis of ophthalmic diseases and conditions has proven to be a highly effective technique, particularly when faced with domains with limited data. By retraining a model with weights already optimized to recognize the features of standard objects rather than training a completely blank network, the model or classifier can recognize the distinguishing features of images much faster and with significantly fewer training examples.

In some embodiments, a machine learning approach is applied to medical data for predicting patient visual acuity. In some embodiments, this machine learning framework comprises a comprehensive functional evaluation system of myopic maculopathy based on maculopathy grade, axial length, and fixation stability for highly myopic eyes. This system can accurately predict visual prognosis after cataract surgery, which would lead to improved ability to counsel patients and set expectations prior to surgery, leading to more informed clinical decision-making and potentially higher patient satisfaction. In some the machine learning approach utilizes medical data such as post-surgery macular sensitivity threshold images. In some embodiments, the machine learning approach utilizes a two-layer hierarchical neural network. In some embodiments, principal component analysis (PCA), an unsupervised approach, is first applied to identify lower dimensional features in macular sensitivity images that correlate with visual acuity. In some embodiments, a hierarchical neural network, e.g. deep learning, was applied on the macular sensitivity images, along with age and axial length, which also have information towards predicting post-operative BCVA. In some embodiments, the neural network model predicts visual acuity in patients using macular sensitivity test results with high accuracy.

Medical Imaging

In certain aspects, the machine learning framework disclosed herein is used for analyzing medical imaging data. In some embodiments, the medical imaging data comprises ophthalmic images, which can include images of the internal structure of the eye such as the retina and/or retinal vasculature, macula, and optic nerve. The framework described herein is applicable to various types of medical imaging including ophthalmic imaging. Ophthalmic imaging is a type of medical imaging that scans or captures one or more structures of the eye. In some embodiments, the machine learning framework is used to analyze ophthalmic images generated using at least one ophthalmic medical imaging technique selected from optical coherence tomography (OCT), color fundus photography of the retina (CFP), corneal topography, slit-lamp photography, fluorescein angiography, indocyanine green angiography, fundus auto-fluorescence, optic nerve head analysis, endothelial cell-layer imaging, and external imaging. In some embodiments, ophthalmic images are generated using specialized imaging equipment. In some embodiments, a digital retinal camera is used for color fundus photography and fluorescein angiography. In some embodiments, an optical coherence tomography enables cross-sectional imaging of the retina such as for macular and optic nerve head imaging. In some embodiments, a scanning laser ophthalmoscope is used for fundus autofluorescence, fluorescein angiography and indocyanine green angiography. In some embodiments, photo slit-lamp micrography is used to photograph anterior eye structures (e.g. cornea, iris, conjunctiva, and lens). In some embodiments, corneal topography is used to measure the thickness, refractive power, and shape of the cornea. In some embodiments, an optic nerve head analyzer is used for optic nerve head imaging. In some embodiments, external photography is used to image the exterior of the eye, eyelid, or other structures in proximity to the eye. In some embodiments, a Rostock corneal module (RCM) is used to generate high-magnification images of the corneal layers, which allows counting of endothelial cells.

A lack of sufficient suitable medical images or medical imaging data can lead to inaccurate or poorly trained classifiers. However, embodiments of the systems, methods, and devices disclosed herein implement transfer learning to improve the training of models using images or imaging data that is not suitable for directly training the classifier. In some embodiments, a model is trained during a first step using non-medical images. In some embodiments, transfer learning is implemented to further train a model on suitable medical images (e.g., OCT images with associated diagnostic outcomes). By leveraging non-medical or non-domain medical images for part of the training, a trained model or classifier can be generated that provides improved predictive accuracy compared to a model trained using only the available medical images.

In some embodiments, the algorithms disclosed herein such as machine learning algorithms use transfer learning. In some embodiments, the algorithms disclosed herein use non-medical images (or non-domain medical images) to pre-train a model or classifier. In some embodiments, the algorithms disclosed herein that utilize a transfer learning procedure using a combination of non-medical and medical images achieve at least one performance metric (an accuracy, sensitivity, specificity, AUC, positive predictive value, negative predictive value, or any combination thereof) for an independent data set (e.g., test dataset not used in training) that is at least 80%, 85%, 90%, 95%, 96%, 97%, 98%, or at least 99% similar to an algorithm that is trained using the medical images alone. In some embodiments, the similar performance metric is obtained when the transfer learning procedure and the non-transfer learning procedure utilize the same set of medical images for training.

In some embodiments, a machine learning algorithm or model is pre-trained using non-medical images numbering about 1,000 to about 300,000. In some embodiments, a machine learning algorithm or model is pre-trained using non-medical images numbering at least about 1,000. In some embodiments, a machine learning algorithm or model is pre-trained using non-medical images numbering at most about 300,000. In some embodiments, a machine learning algorithm or model is pre-trained using non-medical images numbering about 1,000 to about 2,000, about 1,000 to about 5,000, about 1,000 to about 10,000, about 1,000 to about 15,000, about 1,000 to about 20,000, about 1,000 to about 30,000, about 1,000 to about 40,000, about 1,000 to about 50,000, about 1,000 to about 100,000, about 1,000 to about 200,000, about 1,000 to about 300,000, about 2,000 to about 5,000, about 2,000 to about 10,000, about 2,000 to about 15,000, about 2,000 to about 20,000, about 2,000 to about 30,000, about 2,000 to about 40,000, about 2,000 to about 50,000, about 2,000 to about 100,000, about 2,000 to about 200,000, about 2,000 to about 300,000, about 5,000 to about 10,000, about 5,000 to about 15,000, about 5,000 to about 20,000, about 5,000 to about 30,000, about 5,000 to about 40,000, about 5,000 to about 50,000, about 5,000 to about 100,000, about 5,000 to about 200,000, about 5,000 to about 300,000, about 10,000 to about 15,000, about 10,000 to about 20,000, about 10,000 to about 30,000, about 10,000 to about 40,000, about 10,000 to about 50,000, about 10,000 to about 100,000, about 10,000 to about 200,000, about 10,000 to about 300,000, about 15,000 to about 20,000, about 15,000 to about 30,000, about 15,000 to about 40,000, about 15,000 to about 50,000, about 15,000 to about 100,000, about 15,000 to about 200,000, about 15,000 to about 300,000, about 20,000 to about 30,000, about 20,000 to about 40,000, about 20,000 to about 50,000, about 20,000 to about 100,000, about 20,000 to about 200,000, about 20,000 to about 300,000, about 30,000 to about 40,000, about 30,000 to about 50,000, about 30,000 to about 100,000, about 30,000 to about 200,000, about 30,000 to about 300,000, about 40,000 to about 50,000, about 40,000 to about 100,000, about 40,000 to about 200,000, about 40,000 to about 300,000, about 50,000 to about 100,000, about 50,000 to about 200,000, about 50,000 to about 300,000, about 100,000 to about 200,000, about 100,000 to about 300,000, or about 200,000 to about 300,000. In some embodiments, a machine learning algorithm or model is pre-trained using non-medical images numbering about 1,000, about 2,000, about 5,000, about 10,000, about 15,000, about 20,000, about 30,000, about 40,000, about 50,000, about 100,000, about 200,000, or about 300,000.

In some embodiments, a machine learning algorithm or model is trained using medical images numbering about 50 to about 50,000. In some embodiments, a machine learning algorithm or model is trained using medical images numbering at least about 50. In some embodiments, a machine learning algorithm or model is trained using medical images numbering at most about 50,000. In some embodiments, a machine learning algorithm or model is trained using medical images numbering about 50 to about 100, about 50 to about 200, about 50 to about 300, about 50 to about 400, about 50 to about 500, about 50 to about 1,000, about 50 to about 5,000, about 50 to about 10,000, about 50 to about 20,000, about 50 to about 30,000, about 50 to about 50,000, about 100 to about 200, about 100 to about 300, about 100 to about 400, about 100 to about 500, about 100 to about 1,000, about 100 to about 5,000, about 100 to about 10,000, about 100 to about 20,000, about 100 to about 30,000, about 100 to about 50,000, about 200 to about 300, about 200 to about 400, about 200 to about 500, about 200 to about 1,000, about 200 to about 5,000, about 200 to about 10,000, about 200 to about 20,000, about 200 to about 30,000, about 200 to about 50,000, about 300 to about 400, about 300 to about 500, about 300 to about 1,000, about 300 to about 5,000, about 300 to about 10,000, about 300 to about 20,000, about 300 to about 30,000, about 300 to about 50,000, about 400 to about 500, about 400 to about 1,000, about 400 to about 5,000, about 400 to about 10,000, about 400 to about 20,000, about 400 to about 30,000, about 400 to about 50,000, about 500 to about 1,000, about 500 to about 5,000, about 500 to about 10,000, about 500 to about 20,000, about 500 to about 30,000, about 500 to about 50,000, about 1,000 to about 5,000, about 1,000 to about 10,000, about 1,000 to about 20,000, about 1,000 to about 30,000, about 1,000 to about 50,000, about 5,000 to about 10,000, about 5,000 to about 20,000, about 5,000 to about 30,000, about 5,000 to about 50,000, about 10,000 to about 20,000, about 10,000 to about 30,000, about 10,000 to about 50,000, about 20,000 to about 30,000, about 20,000 to about 50,000, or about 30,000 to about 50,000. In some embodiments, a machine learning algorithm or model is trained using medical images numbering about 50, about 100, about 200, about 300, about 400, about 500, about 1,000, about 5,000, about 10,000, about 20,000, about 30,000, or about 50,000.

Machine Learning

Disclosed herein, in various embodiments, are machine learning methods for analyzing medical data including, for example, ophthalmic images and eye-related data (e.g. maculopathy grade, axial length, and fixation stability). In an exemplary embodiment, the machine learning framework disclosed herein is used for analyzing optical coherence tomography (OCT) images for the diagnosis of ophthalmic diseases or conditions such as common causes of blinding retinal diseases. Examples of ophthalmic diseases, disorders, or conditions include diabetic retinopathy, age-related macular degeneration, diabetic macular edema, and choroidal neovascularization. Other examples include retinal tears, retinal detachment, epiretinal membrane, macular hole, macular edema, macular pucker, retinitis pigmentosa, glaucoma, central serous retinopathy, and vitreous traction. In some embodiments, the predictions or diagnoses generated according to the systems, methods, and devices described herein include detection or diagnosis of an ophthalmic disease, disorder, or condition. In some embodiments, the predictions or diagnoses include evaluation of risk or likelihood of an ophthalmic disease, disorder, or condition. In some embodiments, the predictions or diagnosis comprise a category or classification of an ophthalmic disease, disorder, or condition. For example, a prediction or diagnosis can include a diagnosis of highly myopic maculopathy and/or a category of the highly myopic maculopathy (e.g., category 1-4).

In various embodiments, medical imaging is used for carrying out predictions or diagnoses described herein. For example, optical coherence tomography (OCT) is a three-dimensional medical imaging technique that uses light to capture high resolution three-dimensional cross-sectional images of living retinal tissue. It has become one of the most commonly performed medical imaging procedures, with over 5 million OCT scans performed in the U.S. Medicare population in 2014 alone (Centers for Medicare and Medicaid Services). OCT imaging is now the standard of care for guiding the diagnosis and treatment of the leading causes of blindness in the developed world: age-related macular degeneration (AMD) and diabetic macular edema (DME). Approximately 8 million individuals in the United States suffer from early or intermediate AMD, and almost 1 million will develop late AMD within the next 5 years (Stevens et al. 2013). Each year in the United States, more than 250,000 people developed choroidal neovascularization, a severe blinding form of AMD (Stevens et al, 2013). In addition, nearly 750,000 individuals aged 40 or older suffer from DME. The prevalence of these diseases will likely increase even further over time due to the aging population and the global diabetes epidemic. However, the advent and widespread utilization of anti-vascular endothelial growth factor (anti-VEGF) medications has revolutionized the treatment of retinal diseases. Anti-VEGF treatment for fluid or blood in the retina, whether it is due to DME or to choroidal neovascularization (CNV), which is a late-stage blinding complication of AMD, has been shown to decrease the likelihood of advancing to end-stage complications and irreversible vision loss. Treatment decisions regarding when to administer anti-VEGF medications now are often dictated by findings in the OCT images of the central retina (FIG. 2A). As OCT is increasingly used in community settings, rapid and accurate diagnostic screening for these blinding eye diseases becomes even more crucial. This is particularly relevant in areas without easy access to specialized physicians, such as rural areas or developing/low-income settings. Delays in diagnosis and/or treatment could result in severe loss of visual function. It is recognized in the present disclosure that one solution is to implement computational decision support algorithms for interpretation of medical imaging such as OCT images.

In certain embodiments, OCT imaging is used to detect or diagnose AMD and DME. In some embodiments, other types of medical images are used to reliably diagnose various other retinal pathologies. As an example, fundus imaging is essential in identifying key signs of diabetic retinopathy, a common and preventable cause of blindness in the U.S. In some embodiments, disclosed herein are techniques that reliably diagnose (e.g. equal to or better than the average clinician or expert trained to perform the diagnosis) retinal pathologies when exposed to different modalities such as differing image types.

Disclosed herein, in various aspects, are methods incorporating machine learning techniques (e.g. deep learning utilizing convolutional neural networks) that demonstrate great diagnostic power using retinal imagery that leverages databases of retinal images including public databases. Conventional approaches in computer vision using deep learning in other medical fields have encountered significant challenges due to the unavailability of large datasets of labeled medical imagery. Disclosed herein are methods that solve these challenges using innovative methods such as the application of transfer learning.

Accordingly, in some embodiments, provided herein is an AI transfer learning framework for the diagnosis of common sight-threatening retinal diseases with a dataset of OCT images that is capable of achieving highly accurate diagnosis comparable to human expert performance. In some embodiments, this AI framework categorizes images with CNV or DME as "urgent referrals" and images with drusen as "routine referrals." In some embodiments, normal images are labeled for "observation." Thus, certain embodiments of the present disclosure utilize the AI framework as a triage system to generate a referral, mimicking real-world applications in community settings, primary care, and urgent care clinics. These embodiments may ultimately confer broad public health impact by promoting earlier diagnosis and detection of disease progression, thereby facilitating treatment that can improve visual outcomes and quality of life.

According to one aspect of the present disclosure, disclosed herein is an AI or machine learning platform for diagnosis and referral of one or more causes of severe vision loss. Examples of common causes of severe vision loss include diabetic macular edema (DME) and choroidal neovascularization (CNV), which may be seen in neovascular age-related macular degeneration. By employing a transfer learning algorithm, a model generated according to the methods (e.g. classifiers or trained ML algorithms) disclosed herein demonstrated competitive performance of OCT image analysis without the need for a highly specialized deep learning machine and without a database of millions of example images. Moreover, the model's performance in diagnosing retinal OCT images was comparable to that of human experts with significant clinical experience with retinal diseases. When the model was trained with a much smaller number of images (about 1000 from each class), its accuracy, sensitivity, specificity, and area under the ROC curve were all slightly decreased compared with the model trained on over 150,000 total images, but it was still overall a very high-performing system, thereby illustrating the power of the transfer learning system to make highly effective classifications even with a very limited training dataset.

In certain aspects, disclosed herein are machine learning frameworks for generating models or classifiers that diagnose one or more ophthalmic disorders or conditions. These models or classifiers can be implemented in any of the systems or devices disclosed herein such as diagnostic kiosks or portable devices such as smartphones with attachable imaging devices (e.g., ophthalmoscopes). As used herein, diagnosing or a diagnosis of an ophthalmic disorder or condition can include a prediction or diagnosis of a visual outcome following a medical procedure. In some embodiments, the machine learning frameworks generate models or classifiers that generate predictions such as, for example, post-operative visual outcomes (e.g. cataract surgery). In some embodiments, the prediction comprises an indication of an ophthalmic disease or condition such as, for example, diabetic retinopathy or a symptom/condition thereof. In some embodiments, the prediction comprises an indication of one or more of a plurality of ophthalmic diseases or conditions (optionally including post-operative visual outcomes) such as drusen, DME, and CNV. In some embodiments, disclosed herein is a classifier diagnosing one or more ophthalmic disorders or conditions based on one or more medical images. In some embodiments, the one or more ophthalmic disorders or conditions are selected from diabetic macular edema, choroidal neovascularization, and drusen. In some embodiments, an ophthalmic disease or disorder includes age-related macular degeneration.

In some embodiments, the classifier exhibits performance metrics such as accuracy, sensitivity, specificity, positive predictive value, negative predictive value, and/or AUC for an independent sample set. In some embodiments, the classifier exhibits performance metrics such as higher accuracy, sensitivity, specificity, positive predictive value, negative predictive value, and/or AUC for an independent sample set compared to an average human clinician (e.g. an average ophthalmologist). In some embodiments, the classifier provides an accuracy of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1000 independent samples (e.g. images). In some embodiments, the classifier provides a sensitivity (true positive rate) of at least 70%, at least 75%, at least 80%, at least 85%, at least 90%, at least 91%, at least 92%, at least 93%, at least 94%, at least 95%, at least 96%, at least 97%, at least 98%, at least 99%, and/or a specificity (true negative rate) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1000 independent samples (e.g. images). In some embodiments, the classifier provides a positive predictive value (PPV) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1000 independent samples (e.g. images). In some embodiments, the classifier provides a negative predictive value (NPV) of at least 70%, at least 75%, at least 80%, at least 85%, at least 90%, at least 91%, at least 92%, at least 93%, at least 94%, at least 95%, at least 96%, at least 97%, at least 98%, or at least 99% when tested against at least 100, 200, 300, 400, 500, 600, 700, 800, 900, or 1000 independent samples (e.g. images). In some embodiments, the classifier has an AUC of at least 0.7, 0.75, 0.8, 0.85, 0.9, 0.91, 0.92, 0.93, 0.94, 0.95, 0.96, 0.97, 0.98 or 0.99 when tested against at least 100, 200, 300, 400, 500, 600, 700, 800, 900, or 1000 independent samples (e.g. OCT images). In some embodiments, the classifier has a weighted error compared to one or more independent experts of no more than 20%, no more than 15%, no more than 12%, no more than 10%, no more than 9%, no more than 8%, no more than 7%, no more than 6%, no more than 5%, no more than 4%, no more than 3%, no more than 2%, or no more than 1% when tested against at least 100, 200, 300, 400, 500, 600, 700, 800, 900, or 1000 independent samples (e.g. OCT images).

Embodiments of the framework disclosed herein demonstrate competitive performance on both OCT and fundus modalities without the need for a highly specialized deep learning machine and without a database of millions of example images. Since the distinguishing features of disease are generally more straightforward in OCT images, the model performs as well as human experts in diagnosis of OCT images. Moreover, although the more subtle indicators of pathology and greater variability between images belonging to the same class in fundus images can negatively impact model accuracy, models generated according to the present framework perform competitively and would still scale in performance with added input images.

According to one aspect of the present disclosure, an occlusion test to identify the areas of greatest importance used by the model in assigning diagnosis is performed. The greatest benefit of an occlusion test is that it reveals insights into the decisions of neural networks, which are sometimes referred to as "black boxes" with no transparency. Since this test is performed after training is completed, it demystifies the algorithm without affecting its results. The occlusion test also confirms that the network makes its decisions using accurate distinguishing features. In some embodiments, various platforms, systems, media, and methods recited herein comprise providing one or more of the areas of greatest importance identified by the occlusion test to a user or subject. In some embodiments, the one or more areas are provided in the form of a report (analog or electronic/digital). In some embodiments, the report is provided to a clinician, the subject of the report, a third party, or a combination thereof. In some embodiments, the report is annotated with medical insight such as descriptions or explanations of how the one or more areas are relevant to the diagnosis. This has the benefit of instilling greater trust and confidence in the methodology. In some embodiments, the medical insight is simplified into layman's terms for a non-clinician or medical practitioner such as the subject or a third party (e.g., parent of the subject). In some embodiments, the report comprises an occlusion image (e.g., image showing areas of greatest importance) used in the diagnosis or prediction. In some embodiments, the machine learning algorithm comprises a neural network. In some embodiments, the neural network comprises at least 1, at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, at least 100, at least 150, at least 200, at least 250, at least 300, at least 350, at least 400, at least 450, at least 500, at least 600, at least 700, at least 800, at least 900, at least 1000, at least 5000, or at least 10000 or more neurons or nodes and/or no more than 2, no more than 3, no more than 4, no more than 5, no more than 6, no more than 7, no more than 8, no more than 9, no more than 10, no more than 15, no more than 20, no more than 25, no more than 30, no more than 40, no more than 50, no more than 60, no more than 70, no more than 80, no more than 90, no more than 100, no more than 150, no more than 200, no more than 250, no more than 300, no more than 350, no more than 400, no more than 450, no more than 500, no more than 600, no more than 700, no more than 800, no more than 900, no more than 1000, no more than 5000, or no more than 10000 neurons or nodes. In some embodiments, the number of neurons is limited to below a threshold number in order to prevent overfitting. In some embodiments, the number of neurons is no more than 5, 6, 7, 8, 9, or 10 neurons.

Although transfer learning allows the training of a highly accurate model with a relatively small training dataset, its performance would be inferior to that of a model trained from a random initialization on an extremely large dataset of OCT images, since even the internal weights can be directly optimized for OCT feature detection. However, transfer learning using a pre-trained model trained on millions of various medical images can generate a more accurate model when retraining layers for other medical classifications.

The performance of a model can depend highly on the weights of the pre-trained model. Therefore, in some embodiments, the performance of this model is enhanced when tested on a larger ImageNet dataset with more advanced deep learning techniques and architecture described herein. Further, in certain embodiments, the performance of this approach is improved by incorporating ongoing developments in the field of convolutional neural networks applied outside of medical imaging.

In some embodiments, OCT imaging is used as a demonstration of a generalized approach in medical image interpretation and subsequent decision making. The disclosed framework identified potential pathology on a tissue map to make a referral decision with performance comparable to human experts, enabling timely diagnose of the two most common causes of irreversible severe vision loss. OCT is particularly useful in the management of retinal diseases because it has become critical to guiding anti-VEGF treatment for the intraretinal and/or subretinal fluid seen in many retinal conditions. This fluid often cannot be clearly visualized by the examiner's eyes via traditional biomicroscopy. In addition, the OCT appearance often correlates well with visual acuity. The presence of fluid is typically associated with worse visual acuity, which improves once the fluid is resolved with anti-VEGF treatment. As a testament to the value of this imaging modality, treatment decisions are now more frequently guided by OCT rather than by clinical examination or fundus photography. Based on the crucial role OCT imaging has in guiding treatment, the subject matter disclosed herein extends the application of artificial intelligence beyond diagnosis or classification of images and into the realm of making treatment recommendations. In some embodiments, the systems, methods, and devices disclosed herein provide one or more treatment recommendations in addition to a diagnosis or detection of an ophthalmic disease or condition. In some embodiments, a treatment recommendation is anti-VEGF treatment. In some embodiments, the anti-VEGF treatment recommendation is made based on detection or diagnosis of DME or CNV. In some embodiments, anti-VEGF treatment comprises administering or providing anti-VEGF medication to the subject for treating an ophthalmic disease such as diabetic retinopathy or symptoms or conditions thereof. In some embodiments, the treatment recommendation comprises one or more of blood pressure medication, anti-VEGF medication, laser surgery, vitrectomy, or any combination thereof. For example, blood pressure and anti-VEGF medication can lower blood pressure to reduce swelling of the macula. Laser surgery can help seal off leaking blood vessels to reduce retinal swelling. In severe cases of ophthalmic disorders or conditions (e.g., advanced diabetic retinopathy), a vitrectomy may be recommended or performed to remove vitreous gel and blood from leaking vessels (and optional removal of scar tissue) to restore or improve visual acuity. In some embodiments, the treatment recommendation comprises lifestyle advice such as methods for managing blood sugar through diet, exercise, medicine, and other factors. In some embodiments, the treatment recommendation further comprises one or more healthcare providers suitable for providing the recommended treatment. In some embodiments, the one or more healthcare providers are selected based on location proximity to the location of the user and/or the system or device providing the recommendation. In some embodiments, the healthcare providers are selected based on available resources for providing the recommended treatment. In some embodiments, additional information for the healthcare providers is provided, which can include estimated time to arrival (for traveling to the provider location), estimated wait time, estimated cost, and/or other information associated with the healthcare providers. In some embodiments, the patient is administered a treatment based on a diagnosed or detected ophthalmic disease or condition. In some embodiments, the patient is administered a recommended treatment based on a diagnosed or detected ophthalmic disease or condition. In some embodiments, the systems, methods, and devices disclosed herein provide a recommendation for further testing.

Various algorithms can be used to generate models that generate a prediction based on the image analysis. In some instances, machine learning methods are applied to the generation of such models (e.g. trained classifier). In some embodiments, the model is generated by providing a machine learning algorithm with training data in which the expected output is known in advance.

In some embodiments, the systems, devices, and methods described herein generate one or more recommendations such as treatment and/or healthcare options for a subject. In some embodiments, the systems, devices, and methods herein comprise a software module providing one or more recommendations to a user. In some embodiments, the treatment and/or healthcare option are specific to the diagnosed disease or condition. For example, a recommendation can suggest a nearby hospital, doctor, or clinic with the requisite facilities or resources for treating the disease or disorder In some embodiments, a classifier or trained machine learning algorithm of the present disclosure comprises a feature space. In some cases, the classifier comprises two or more feature spaces. The two or more feature spaces may be distinct from one another. In some embodiments, a feature space comprises information such as pixel data from an image. When training the machine learning algorithm, training data such as image data is input into the algorithm which processes the input features to generate a model. In some embodiments, the machine learning algorithm is provided with training data that includes the classification (e.g. diagnostic or test result), thus enabling the algorithm to train by comparing its output with the actual output to modify and improve the model. This is often referred to as supervised learning. Alternatively, in some embodiments, the machine learning algorithm can be provided with unlabeled or unclassified data, which leaves the algorithm to identify hidden structure amongst the cases (referred to as unsupervised learning). Sometimes, unsupervised learning is useful for identifying the features that are most useful for classifying raw data into separate cohorts.

In some embodiments, one or more sets of training data are used to train a machine learning algorithm. Although exemplar embodiments of the present disclosure include machine learning algorithms that use convolutional neural networks, various types of algorithms are contemplated. In some embodiments, the algorithm utilizes a predictive model such as a neural network, a decision tree, a support vector machine, or other applicable model. In some embodiments, the machine learning algorithm is selected from the group consisting of a supervised, semi-supervised and unsupervised learning, such as, for example, a support vector machine (SVM), a Naïve Bayes classification, a random forest, an artificial neural network, a decision tree, a K-means, learning vector quantization (LVQ), self-organizing map (SOM), graphical model, regression algorithm (e.g. linear, logistic, multivariate, association rule learning, deep learning, dimensionality reduction and ensemble selection algorithms. In some embodiments, the machine learning algorithm is selected from the group consisting of: a support vector machine (SVM), a Naïve Bayes classification, a random forest, and an artificial neural network. Machine learning techniques include bagging procedures, boosting procedures, random forest algorithms, and combinations thereof. Illustrative algorithms for analyzing the data include but are not limited to methods that handle large numbers of variables directly such as statistical methods and methods based on machine learning techniques. Statistical methods include penalized logistic regression, prediction analysis of microarrays (PAM), methods based on shrunken centroids, support vector machine analysis, and regularized linear discriminant analysis.

Diagnostic Platforms, Systems, Devices, and Media

Provided herein, in certain aspects, are platforms, systems, devices, and media for analyzing medical data according to any of the methods of the present disclosure. In some embodiments, the systems and electronic devices are integrated with a program including instructions executable by a processor to carry out analysis of medical data. In some embodiments, the analysis comprises processing at least one medical image with a classifier such as a neural network, optionally trained on non-domain medical images using transfer learning. In some embodiments, the analysis is performed locally on the device utilizing local software integrated into the device. In some embodiments, the analysis is performed remotely on a remote system or server. In some embodiments, the analysis is performed remotely on the cloud after the image is uploaded by the system or device over a network. In some embodiments, the system or device is an existing system or device adapted to interface with a web application operating on the network or cloud for uploading and analyzing image data such as ophthalmic images. In some embodiments, the system or device provides for portable image storage such as on a USB drive or other portable hard drive. Portable storage enables the images to be transferred to a device capable of performing analysis on the images and/or which has network connectivity for uploading the images for remote analysis on the cloud.

Cloud-Based Diagnosis

Figure 12:
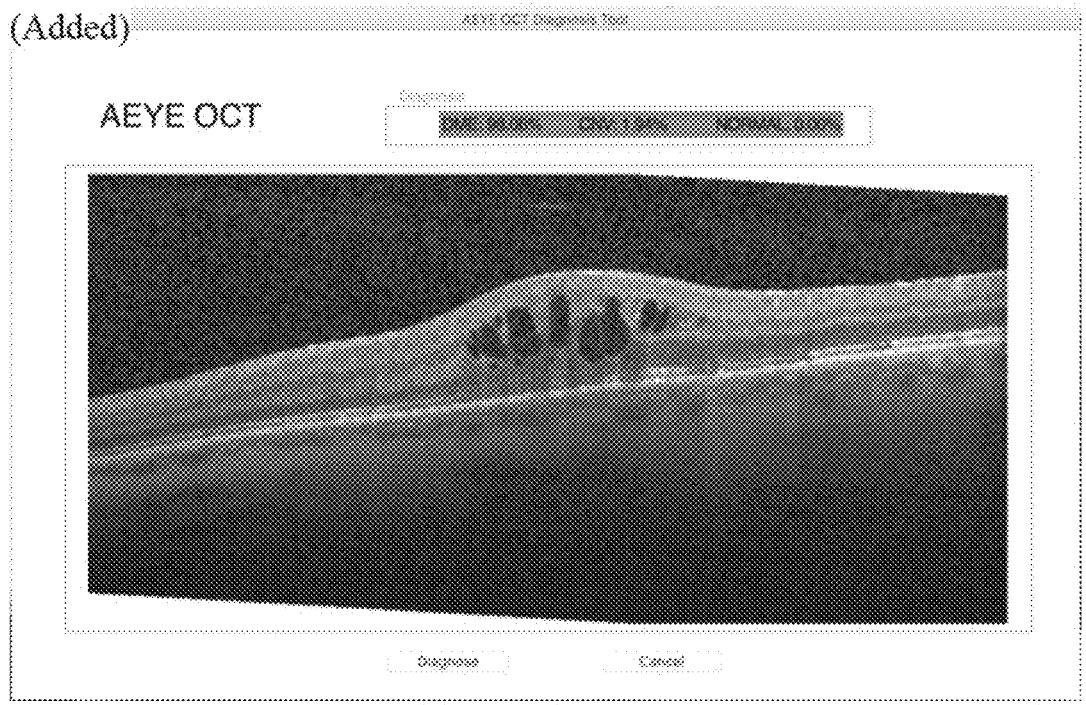
FIG. 12 shows the diagnosis gateway cloud that can upload and make a diagnosis.

Provided herein, in certain embodiments, are systems, devices, and methods for providing a web application or portal for remote data analysis or diagnosis (e.g., "cloud" diagnosis). In order to tackle the reproducibility and transparency issues brought on by training and testing on a protected or proprietary dataset, such as medical OCT imagery, provided herein is an easy-to-use application (e.g. web tool) that allows testing of a model on any provided OCT image (FIG. 12). In some embodiments, the application allows a user to load a trained model and predicts the diagnosis of any user-provided image. In some embodiments, the application provides a breakdown of the diagnosis such as generated using softmax probabilities. In some embodiments, the application allows a user to test the algorithm and even upload smartphone captures of OCT images and yields comparable accuracy. In some embodiments, the application is in communication with a diagnostic or imaging device as described herein. For example, a diagnostic or imaging device used at the point of care such as at a hospital or outside of the clinic setting (e.g. using a portable diagnostic or imaging device at home) can be used to obtain an image of a subject that is then uploaded over a network such as the Internet for remote diagnosis using the application. The diagnosis can then be provided to the user who uploaded the image and/or the subject from whom the image was obtained. In some embodiments, the diagnosis and/or any additional information (e.g. statistical breakdown, instructions, treatment recommendations, etc) is provided to the user and/or subject using e-mail, text messaging, a web portal, regular mail, or other available communication method. In some embodiments, the diagnosis and/or additional information is provided through a secure HIPAA-compliant application or portal (e.g. requiring secured and encrypted login). In some embodiments, the user and/or subject is sent a non-identifying message containing a link and/or information allowing the user or subject to retrieve the diagnosis and/or additional information from a secure storage location such as through a HIPAA-compliant portal.

Furthermore, the disclosed network represents a generalized platform which can potentially apply to a very wide range of medical imaging techniques (e.g. MRI, CT, etc.) to make a clinical diagnostic decision. This could facilitate screening programs and create more efficient referral systems, particularly in remote or low-resource areas, leading to a broad clinical and public health impact.

In some aspects, disclosed herein is a computer-implemented system configured to carry out cloud-based analysis of medical data such as ophthalmic images. In some embodiments, the system comprises one or more servers operatively coupled to a network. In some embodiments, the system is configured to provide a web portal, including a browser-based web portal, web-based application, or web-based application programming interface (API) accessible by end users on the network. In some embodiments, the web portal comprises an interface for receiving user instructions and/or medical data uploads. In some embodiments, the system receives at least one ophthalmic image from an end user or electronic device of an end user. In some embodiments, the ophthalmic image is captured by the electronic device of the end user at the point of care and uploaded to the system on the cloud for analysis. In some embodiments, the web portal is secured by encrypted pass-word protected login. In some embodiments, the system receives uploaded instructions and/or medical data and performs analysis of the medical data using any of the diagnostic methods described herein. In some embodiments, the system generates output from the analysis of the medical data. In some embodiments, the system provides the output of the analysis to the end user on the network. In some embodiments, the system sends the output to an electronic device of the end user such as a computer, smartphone, tablet or other digital processing device configured for network communications.

Hardware/Software Integration

Disclosed herein, in some aspects, are electronic devices comprising software configured for performing the machine learning algorithms described herein. In some embodiments, the electronic device comprises an imaging component for capturing an image of a subject, a user interface for communicating with and/or receiving instructions from a user or subject, a memory, at least one processor, and non-transitory computer readable media providing instructions executable by the at least one processor for performing analysis of the captured image. In some embodiments, the electronic device comprises a network component for communicating with a network or cloud. The network component is configured to communicate over a network using wired or wireless technology. In some embodiments, the network component communicates over a network using Wi-Fi, Bluetooth, 2G, 3G, 4G, 4G LTE, 5G, WiMAX, WiMAN, or other radiofrequency communication standards and protocols.

In some embodiments, the system or electronic device captures a plurality of images for analysis. In some embodiments, the plurality of images are merged and/or analyzed collectively. In some embodiments, the electronic device is not configured to carry out analysis of the captured image locally, instead uploading the captured image to a network for cloud-based or remote analysis. In some embodiments, the electronic device comprises a web portal application that interfaces with the network or cloud for remote analysis and does not carry out any analysis locally. An advantage of this configuration is that image data is not stored locally and thus less vulnerable to being hacked or lost. Alternatively or in combination, the electronic device is configured to carry out analysis of the captured image locally. An advantage of this configuration is the ability to perform analysis in locations lacking network access or coverage (e.g. in certain remote locations lacking internet coverage). In some embodiments, the electronic device is configured to carry out analysis of the captured image locally when network access is not available as a backup function such as in case of an internet outage or temporary network failure. In some embodiments, the image data is uploaded for storage on the cloud regardless of where the analysis is carried out. For example, in certain instances, the image data is temporarily stored on the electronic device for analysis, and subsequently uploaded on the cloud and/or deleted from the electronic device's local memory.

In some embodiments, the system comprises the electronic device and cloud-based server(s) carrying out the analysis and/or storing the image data. In some embodiments, the system comprises the electronic device and an imaging component physically separate from the electronic device. As an example, the system comprises an electronic device that is a desktop computer coupled to or otherwise in communication with an imaging component (e.g. a retinal camera). In some embodiments, the system allows for an image to be captured using the imaging component, and the analysis to be performed by the electronic device, or alternatively, by the cloud following upload of the image. In some embodiments, the system comprises the electronic device for analyzing and/or uploading an image, an imaging component for capturing an image and configured to send the image or image data to the electronic device, and a cloud-based server for receiving an uploaded image and storing and/or analyzing the image, and generating a result to be provided to a user via the electronic device or other methods such as by messaging, email, or a phone call. In some embodiments, the system or device comprises a plurality of imaging components. In some embodiments, the plurality of imaging components is configured to capture multiple types of images. In some embodiments, analysis of the multiple types of images is carried out by different classifiers trained on the different image types to provide more than one diagnosis or result. Alternatively, in some embodiments, the more than one diagnosis or result is consolidated or combined into a single result metric (e.g. an average of the predictions for a particular disorder such as CNV, DME, or AMD).

In some embodiments, the electronic device comprises a display for providing the results of the analysis such as a diagnosis or prediction (of the presence and/or progression of a disease or disorder), a treatment recommendation, treatment options, healthcare provider information (e.g. nearby providers that can provide the recommended treatment and/or confirm the diagnosis), or a combination thereof. In some embodiments, the diagnosis or prediction is generated from analysis of the captured image in comparison to previously captured image(s) for the same user to determine the progression of a disease or disorder. In some embodiments, captured images are time-stamped. In some embodiments, captured images are stored as data, which optionally includes meta-data such as a timestamp, location, user info, or other information associated with the images). In some embodiments, the image data is screened for quality. In some embodiments, the image is screened for suitability for analysis. In some embodiments, an image failing the screen is discarded or otherwise rejected from further analysis. In some embodiments, the electronic device prompts a user to take one or more additional images.

In some embodiments, the electronic device comprises a portal providing one or more tools for a user to input information such as name, address, email, phone number, and/or other identifying information. In some embodiments, the portal comprises an interface for obtaining or entering medical data. In some embodiments, the portal is configured to receive medical data for use in the prediction or diagnosis from device through a network (e.g. receives medical data provided by a user smartphone through the internet via a mobile app or web portal). In some embodiments, the medical data comprises at least one of maculopathy grade, axial length, and fixation stability.

In some embodiments, the portal is configured to provide a health assessment through the electronic device. In some embodiments, the health assessment comprises a diagnosis of an ophthalmic disease or condition. In some embodiments, the ophthalmic disease or condition is a predicted visual outcome following a medical procedure. In some embodiments, the predicted visual outcome is myopic maculopathy following a medical procedure that is cataract surgery.

In some embodiments, the portal provides the user with the option to receive the results of the analysis by email, messaging (e.g. SMS, text message), physical printout (e.g. a printed report), social media, by phone (e.g. an automated phone message or a consultation by a healthcare provider or adviser), or a combination thereof. In some embodiments, the captured image(s) is provided to the user. For example, an image can be shown with graphical emphasis (e.g. highlighting, boundaries drawn around the areas, zoomed in view, etc) on the areas that are most important to the diagnosis as identified by the occlusion test, which can help promote understanding and trust in the diagnostic method. In some embodiments, the portal is displayed on a digital screen of the electronic device. In some embodiments, the electronic device comprises an analog interface. In some embodiments, the electronic device comprises a digital interface such as a touchscreen. In various embodiments, existing systems and devices are capable of being adapted to carry out the methods disclosed herein or are capable of interfacing with web applications for performing remote analysis of ophthalmic images. Examples of such systems and electronic include non-mydriatic retinal cameras such as the TRC-NW400 retinal camera, CR-2 retinal camera, S40ptik Cobra fundus camera, and Volk Pictor Plus Portable Retinal Camera.

In some embodiments, the electronic device has a hardware configuration adapted for capturing images of a subject for analysis according to the methods described herein. In some embodiments, the electronic device comprises a specialized imaging component such as a camera operatively coupled to an ophthalmoscope. In some embodiments, the camera and ophthalmoscope are configured as a single integrated unit. In some embodiments, the camera, ophthalmoscope, and electronic device are configured as a single integrated unit such as a portable diagnostic device. In some embodiments, the imaging component is a digital ophthalmoscope. In some embodiments, the imaging component is configured to capture images and/or video (including stills from the video). In some embodiments, the captured images are high definition photos. As used herein, high definition can refer to photos having 1920×1080 or more pixels. In some embodiments, the captured images are fundus photographs or other images as described throughout the present disclosure.

Kiosk

In some embodiments, the system or electronic device is a kiosk or a component of a kiosk. In some embodiments, the kiosk comprises an enclosure storing internal components such as the imaging component, processor, memory, storage, network component, and other hardware. In some embodiments, the kiosk comprises a seat for seating a user in front of the imaging component. In some embodiments, the kiosk comprises a positioning component for positioning the head of the user in front of the imaging component to capture an image. In some embodiments, the positioning component is configured to reduce head tilt. Because the eye is a 3-dimensional structure, the direction of the visual axis and ocular cyclotorsion can distort images that are taken of the eye and its internal structures. Thus, head tilt can result in ocular cyclotorsion and potentially negatively impact the quality and consistency of captured ophthalmic images. Accordingly, in some embodiments, the systems and devices disclosed herein such as a kiosk comprise a head positioner that reduces and/or manages head tilt to reduce the impact of ocular cyclotorsion on image quality or analysis. In some embodiments, the head positioner comprises a chin rest and a forehead rest configured to position the head of the user at a neutral or close to neutral position that minimizes forward or backward head tilt. In some embodiments, the head positioner comprises lateral rests or supports for minimizing or reducing lateral head tilt. In some embodiments, the head positioner is user adjustable. In some embodiments, the systems and devices disclosed herein are configured to capture and display a video feed or camera image of the user's head to aid in positioning the head to minimize head tilt.

In some embodiments, the kiosk comprises an interface for obtaining or entering medical data. In some embodiments, the kiosk is configured to receive medical data for use in the prediction or diagnosis from another device such as through a network (e.g. receives medical data provided by a user smartphone through the internet via a mobile app or web portal). In some embodiments, the medical data comprises at least one of maculopathy grade, axial length, and fixation stability.

In some embodiments, the kiosk is configured to provide more than one health assessment. In some embodiments, the health assessment comprises a diagnosis of an ophthalmic disease or condition. In some embodiments, the ophthalmic disease or condition is a predicted visual outcome following a medical procedure. In some embodiments, the predicted visual outcome is myopic maculopathy following a medical procedure that is cataract surgery. In some embodiments, the kiosk comprises one or more tools for measuring a user's weight, pulse, blood pressure (systolic and diastolic), body mass index (BMI), hydration, body fat content, or a combination thereof. In some embodiments, the kiosk comprises a seat that is configured to act as a scale for measuring the weight of a seated user. In some embodiments, the seat and a floor of the kiosk operate together as a scale. In some embodiments, the kiosk comprises a floor that acts as a scale for measuring the user's weight. In some embodiments, the kiosk comprises a footrest such that the seat and the footrest act as a scale for measuring the user's bodyweight. In some embodiments, the kiosk comprises a blood pressure cuff configured to measure blood pressure and pulse. In some embodiments, the kiosk comprises a body fat analyzer. In some embodiments, the body fat analyzer is an impedance meter configured to measure a body's electrical impedance. In some embodiments, the body fat analyzer is configured to measure body composition, which can include the estimated amounts of fat, bone, water, muscle, or a combination thereof. In some embodiments, the kiosk is configured to capture an ophthalmic image from a user. Alternatively or in combination, the kiosk is configured to measure the user's weight, pulse, blood pressure, hydration, body fat content, or a combination thereof.

Portable Diagnostic Device

Figure 22:
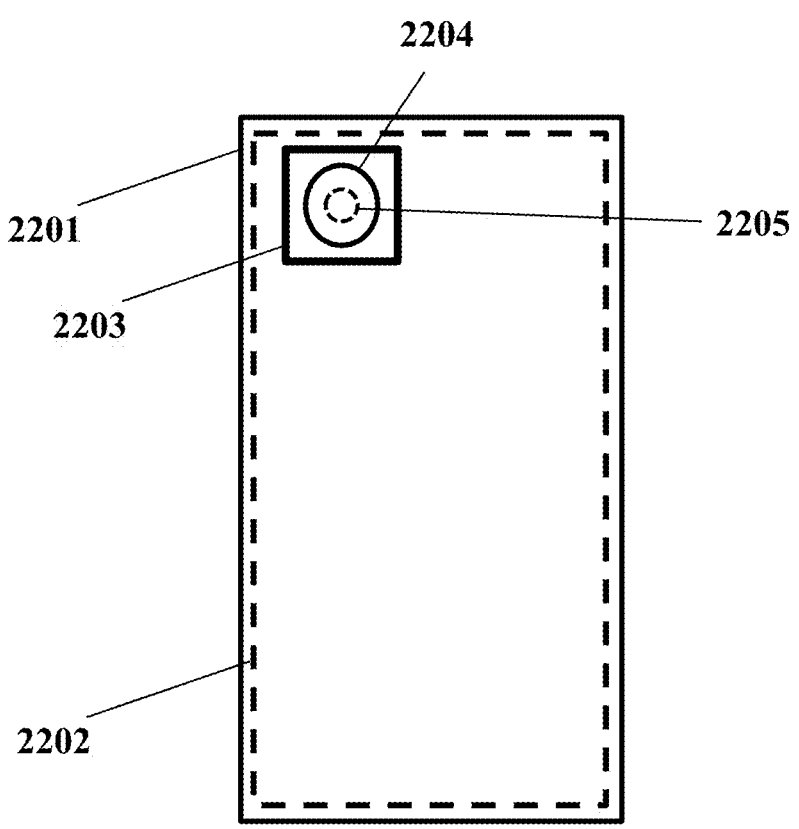
FIG. 22 shows a diagram of one embodiment of an electronic device (cell phone) coupled to a portable device having an imaging component.

In some embodiments, the electronic device is a portable device configured to be handheld or otherwise capable of being transported by an individual. In some embodiments, the portable device comprises an interface for obtaining or entering medical data. In some embodiments, the portable device is configured to receive medical data for use in the prediction or diagnosis from another device such as through a network (e.g. receives medical data provided by a user smartphone through the internet via a mobile app or web portal). In some embodiments, the medical data comprises at least one of maculopathy grade, axial length, and fixation stability. In some embodiments, the portable device comprises a camera for capturing medical images. In some embodiments, the portable device comprises a specialized camera for capturing ophthalmic images. In some embodiments, the specialized camera is a retinal scanner. In some embodiments, the retinal scanner is an OCT imaging device (time-domain or spectral-domain). In some embodiments, the retinal scanner is a non-mydriatic fundus camera. In some embodiments, the retinal scanner performs digital retinal imaging. In some embodiments, the retinal scanner is any one of the imaging devices described throughout the present disclosure. In some embodiments, the portable device comprises a digital processing device for processing the captured image and/or generating a diagnosis or diagnostic prediction. In some embodiments, the portable device is configured to upload one or more captured images onto a network for remote prediction. In some embodiments, the portable device comprises a digital processing device configured to analyze the captured image to generate a prediction. In some embodiments, the portable device is configured to receive updates to the software of the digital processing device (e.g. updating the CNN). In some embodiments, the portable device is configured to analyze the captured image locally when remote prediction is unavailable (e.g. due to lack of network access) or upload the captured image when remote prediction is available. An example of an electronic device with a camera operatively coupled to a portable device comprising an imaging component is shown in FIG. 22.

In some embodiments, the portable device is configured to capture an ophthalmic image in conjunction with a user electronic device such as a smartphone, tablet, laptop, or computer. In some embodiments, the portable device is configured to communicate with the user electronic device through wired and/or wireless technologies. For example, the portable device can be physically connected to the user electronic device through a cable such as a USB, microUSB, or Lightning cable. In some embodiments, wired connections allow the portable device to receive power and/or charge from the user electronic device. As an example, a specialized miniature camera for imaging a user's retina and an optional flash can be powered by a user's smartphone through a USB connection. In some embodiments, the portable device communicates wirelessly with the user electronic device. In some embodiments, the portable device is configured to send a captured image to the user electronic device via a cable and/or wirelessly. In some embodiments, the user electronic device comprises a program such as a mobile application that interfaces with a web application and uploads the captured image to the web application for analysis remotely on the network or cloud.

In some embodiments, the portable device comprises an ophthalmoscope and is configured to align the ophthalmoscope with a camera on a user electronic device to allow a fundus image of a subject's eye to be captured by the camera with the aid of the ophthalmoscope. As a non-limiting example, the portable device is configured to align the ophthalmoscope with a smartphone camera (e.g. an Android phone or iPhone). In some embodiments, the portable device is configured to align the ophthalmoscope with a front-facing camera (e.g. facing the user and/or on the same side as a touchscreen), a rear-facing camera (e.g. facing away from the user), or both. In some embodiments, the portable device is configured to allow user adjustment of the alignment between the ophthalmoscope and the camera of the user electronic device. In some embodiments, the portable device comprises an adaptor shaped to attach to or clip onto a user electronic device. In some embodiments, the adaptor is configured to snugly fit around the outside contour of the user electronic device. In some embodiments, the adaptor comprises a smartphone case. In some embodiments, the smartphone case adaptor is shaped for a specific phone model so as to position the ophthalmoscope in alignment with the phone's camera (front and/or rear). In some embodiments, the adaptor comprises an adjustable strap that can wrap around the user electronic device (e.g. a Velcro strap that can be tightened around the phone). In some embodiments, the ophthalmoscope is coupled to the adaptor. In some embodiments, the ophthalmoscope is detachably coupled to the adaptor. In some embodiments, the ophthalmoscope is movable relative to the adaptor to enable user adjustment of the positioning of the ophthalmoscope to the camera of the user electronic device after the adaptor has been properly mounted to the electronic device. For example, the ophthalmoscope can be coupled to the adaptor via a flexible attachment that can be adjusted to move the ophthalmoscope relative to the adaptor, and thus to the camera of the electronic device.

In some embodiments, the user electronic device is configured to capture an ophthalmic image using its camera in combination with the ophthalmoscope. In some embodiments, the user electronic device is configured to capture a plurality of ophthalmic images. In some embodiments, the plurality of ophthalmic images is screened in which analysis is carried on out one or more images passing the quality screening. In some embodiments, the user electronic device is configured to capture video. In some embodiments, the captured video is screened to identify one or more screenshots of the video, and those screenshot(s) passing the quality control screen are subsequently analyzed to provide a result such as a diagnosis and/or treatment recommendation. In some embodiments, the ophthalmoscope interfaces with both the camera and a flash of the user electronic device such that the flash passes through a filter of the ophthalmoscope for modulating the intensity of the flash. In some embodiments, the ophthalmoscope comprises a semi-transparent area covering the flash to reduce the intensity of the light flash. In some embodiments, the semi-transparent area is adjustable (e.g. the semi-transparent area is a filter that can be removed and replaced with another filter from a set of filters of varying opacity).

In some embodiments, the user electronic device is configured to provide instructions or warnings to a user while capturing the ophthalmic image or video. An advantage of using video is this approach allows the ophthalmoscope to be repositioned with respect to the eye or pupil to capture different areas of the retina and/or fundus over time. For example, some forms of traditional imaging require pupil dilation since undilated pupils will obstruct a complete view of the ocular structures. However, in the case of a patient or non-healthcare provider attempting to capture the ophthalmic image outside of the clinic environment, access to dilating eye drops may not be available. Accordingly, in some embodiments, ophthalmic data is obtained through a video feed, wherein screenshots from the video feed are stitched together to generate a composite image of the areas of the eye that are important for accurate analysis according to the various methods described herein. As an example, the user electronic device is a smartphone comprising a mobile application that visualizes the ophthalmoscope-enhanced camera feed of a subject's eye on its display screen. In some embodiments, the mobile application actively monitors the camera feed and provides instructions for properly capturing an ophthalmic image or video. In some cases, the instructions include steps for carrying out the image capture protocol. In some instances, a warning is provided indicating the camera is not properly aligned with the ophthalmoscope or the pupil, the feed is blurry, the camera/user device is shaking, the feed is being obstructed, or other complications interfering with image capture. In some embodiments, the instructions and/or warnings are provided visually on the screen of the user electronic device. In some embodiments, the instructions and/or warnings are provided by audio (e.g. the instructions/warnings are vocalized through an audio speaker of the user electronic device).

In some embodiments, the portable device is configured to be used by a user to capture an ophthalmic image of an eye of a subject who is not the user. In some embodiments, the portable device is configured to be used by a user to capture an ophthalmic image of the user's own eye. As an example, a smartphone configured to position an ophthalmoscope over a front-facing camera can provide instructions and/or warnings on its display screen enabling a user to self-position the ophthalmoscope to align with his eye (e.g. aligning the ophthalmoscope with his pupil). Alternatively, a smartphone configured to position an ophthalmoscope over a rear-facing camera can provide audio instructions and/or warnings. Non-limiting examples of instructions in no particular order include: 1) explaining the procedure to the user (e.g. the duration of the procedure, whether the user will be exposed to a bright light); 2) instructions to apply one or more mydriatic eye drops to dilate the pupils; 3) instructions on where to look (e.g. a distant object with the non-imaged eye); 4) how to align the ophthalmoscope with the user electronic device; 5) how to align the ophthalmoscope with the eye or pupil; 6) distance to hold the ophthalmoscope from the eye; and 7) instructions to hold still when the alignment is correct.

In some embodiments, the medical data comprises medical images such as ophthalmic images. In some embodiments, the ophthalmic images comprise retinal images. In some embodiments, the system or device comprises an imaging component for capturing an image of a subject. In some embodiments, the image is a retinal image. In some embodiments, the imaging component is configured for optical coherence tomography (OCT), color fundus photography of the retina (CFP), corneal topography, slit-lamp photography, fluorescein angiography, indocyanine green angiography, fundus auto-fluorescence, optic nerve head analysis, endothelial cell-layer imaging, or external imaging such as standard photography. In some embodiments, ophthalmic images are generated using specialized imaging equipment. In some embodiments, a digital retinal camera is used for color fundus photography and fluorescein angiography. In some embodiments, the imaging component is an optical coherence tomography, a scanning laser ophthalmoscope, photo slit-lamp micrography, corneal topography, an optic nerve head analyzer, a photographic camera, or a Rostock corneal module (RCM). In some embodiments, the imaging component is an automated camera for capturing a retinal image (e.g. an automated fundus camera).

Digital Processing Device

In some embodiments, the systems, devices, platforms, media, methods and applications described herein include a digital processing device, a processor, or use of the same. For example, in some embodiments, the digital processing device is part of a point-of-care device such as a medical diagnostic device integrating the diagnostic software described herein. In some embodiments, the medical diagnostic device is a consumer-facing portable medical diagnostic device configured for use outside of the clinical setting (e.g. consumer use at home). In some embodiments, the medical diagnostic device comprises diagnostic equipment such as imaging hardware (e.g. a camera) for capturing medical data (e.g. medical images). In some embodiments, the medical diagnostic device comprises a digital processing device configured to perform the diagnostic methods described herein such as disease detection or classification based on medical images. In further embodiments, the digital processing device includes one or more processors or hardware central processing units (CPU) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device. In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In some embodiments, the non-volatile memory comprises magnetoresistive random-access memory (MRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a subject. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In some embodiments, the display is E-paper or E ink. In other embodiments, the display is a video projector. In still further embodiments, the display is a combination of devices such as those disclosed herein.

In some embodiments, the digital processing device includes an input device to receive information from a subject. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Non-Transitory Computer Readable Storage Medium

In some embodiments, the platforms, media, methods and applications described herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, media, methods and applications described herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft Silverlight®, Java™, and Unity®.

Mobile Application

In some embodiments, a computer program includes a mobile application provided to a mobile digital processing device such as a smartphone. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g. not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable compiled applications.

Software Modules

In some embodiments, the platforms, media, methods and applications described herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of barcode, route, parcel, subject, or network information. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

DETAILED FIGURE DESCRIPTIONS

FIG. 1. Schematic of a Convolutional Neural Network. Schematic depicting how a convolutional neural network trained on an ImageNet dataset of 1,000 categories can be adapted to significantly increase the accuracy and shorten the training duration of a network trained on a novel dataset of OCT images. The locally connected (convolutional) layers are frozen and transferred into a new network, while the final, fully connected layers are recreated and retrained from random initialization on top of the transferred layers.

FIG. 2. (A) Representative optical coherence tomography (OCT) images. Far left panel: choroidal neovascularization (CNV) with associated subretinal fluid (arrow). Middle left panel: diabetic macular edema (DME) with associated intraretinal fluid (arrow). Middle right panel: multiple drusen (arrowheads) present in early AMD. Far right panel: normal retina with preserved foveal contour and absence of any retinal fluid. (B) Workflow diagram showing overall experimental design describing the flow of optical coherence tomography (OCT) images through the labeling and grading process followed by creation of the transfer learning model, which then underwent training and subsequent testing. The training dataset only included images that passed sufficient quality and diagnostic standards from the initial collected dataset.

Figure 3A:
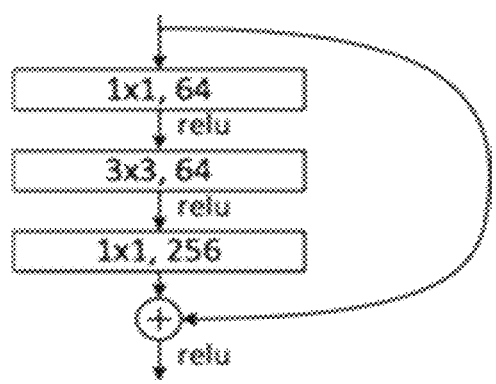
FIG. 3A shows "Bottleneck" building blocks of ResNet architecture consisting of 3 convolutional layers separated by ReLU nonlinearities with an identity addition function.
Figure 3B:
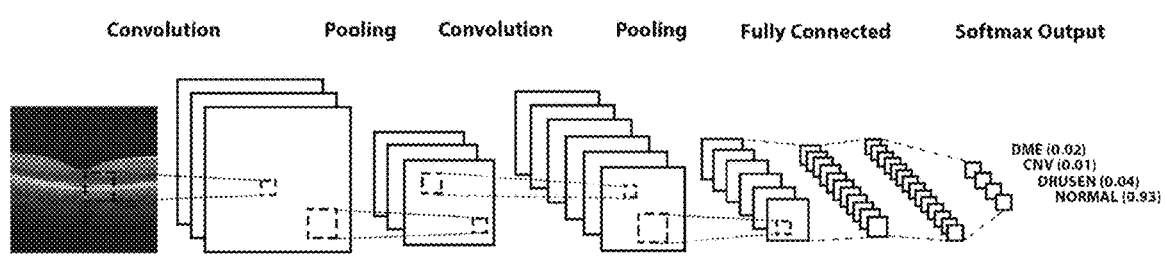
FIG. 3B shows a schematic of a convolutional neural network using the LeNet architecture in order to demonstrate how filters convolve through layers.

FIG. 3A-B. (A) "Bottleneck" building blocks of ResNet architecture consisting of 3 convolutional layers separated by ReLU nonlinearities with an identity addition function. (B) Schematic of a convolutional neural network using the LeNet architecture in order to demonstrate how filters convolve through layers.

FIG. 4A-C. Multi-class comparison between CNV, DME, drusen, and normal (A) Receiver operating characteristic curve for "urgent referrals" (Choroidal Neovascularization (CNV) and Diabetic Macular Edema (DME) detection) with human expert performance for comparison. (B) Confusion table of best model's classification of the validation image set. (C) Weighted error results based on penalties shown in FIG. 10A depicting neural networks in gold and human experts in blue. The weighted errors shown in FIG. 4C are: 0.40% (Expert 5), 1.20% (Expert 1), 2.40% (Expert 3), 6.40% (Expert 4), 6.60% (Best Model), 7.70% (Expert 6), 10.50% (Expert 2), 12.70% (Limited Model).

FIG. 5A-B. The plot, created using TensorBoard, represents the training (orange) and validation (blue) accuracies in (A) and cross entropy loss (B) during training of the multi-class classifier over the course of 10,000 steps. The plot was normalized with a smoothing factor of 0.6 in order to clearly visualize trends.

Figure 6:
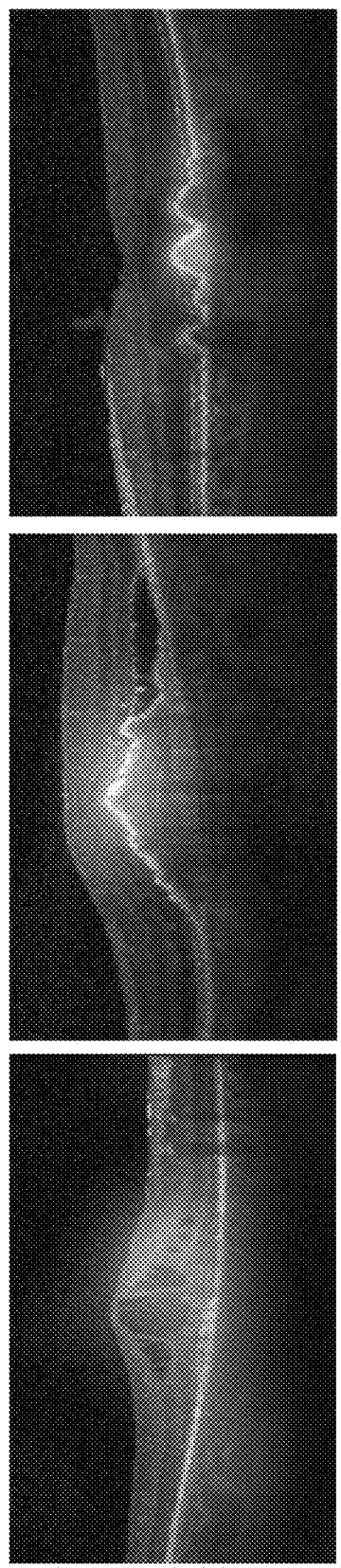
FIG. 6 shows occlusion maps highlighting areas of pathology in diabetic macular edema (left), choroidal neovascularization (middle), and drusen (right).

FIG. 6. occlusion maps highlighting, areas of pathology in diabetic macular edema (left), choroidal neovascularization (middle), and drusen (right). An occlusion map was generated by convolving an occluding kernel across the input image. The occlusion map is created after prediction by assigning the softmax probability of the correct label to each occluded area. The occlusion map can then be superimposed on the input image to highlight the areas the model considered important in making its diagnosis.

FIG. 7. Plots show binary performance in the training and validation datasets using TensorBoard, related to FIG. 5. Comparisons were made for choroidal neovascularization (CNV) versus normal (A), diabetic macular edema (DME) versus normal (B), and drusen versus normal (C). Plots were normalized with a smoothing factor of 0.6 in order to clearly visualize trends. The validation accuracy and loss shows better performance since images with more noise and lower quality were also included in the training set to reduce overfitting and help generalization of the classifier. Training dataset: orange. Validation dataset: blue.

FIG. 8. Receiver operating characteristic curves for binary classifiers, related to FIG. 4. The corresponding area under the ROC (AUROC) for the graphs are 100% for choroidal neovascularization (CNV) versus normal (A), 99.87% for diabetic macular edema (DME) versus normal (B), and 99.96% for drusen versus normal (C). The straight vertical and horizontal lines in (A) and the nearly straight lines in (B) and (C) demonstrate that the binary convolutional neural network models have a near perfect classification performance.

Figure 9A:
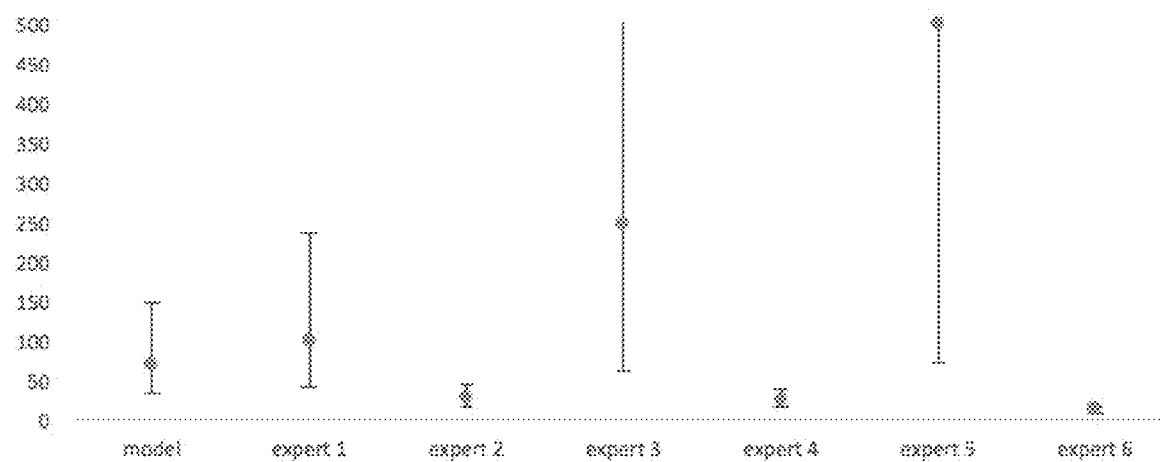
FIG. 9A and FIG. 9B show plots depicting the positive and negative likelihood ratios, respectively, with their corresponding 95% confidence intervals marked.
Figure 9B:
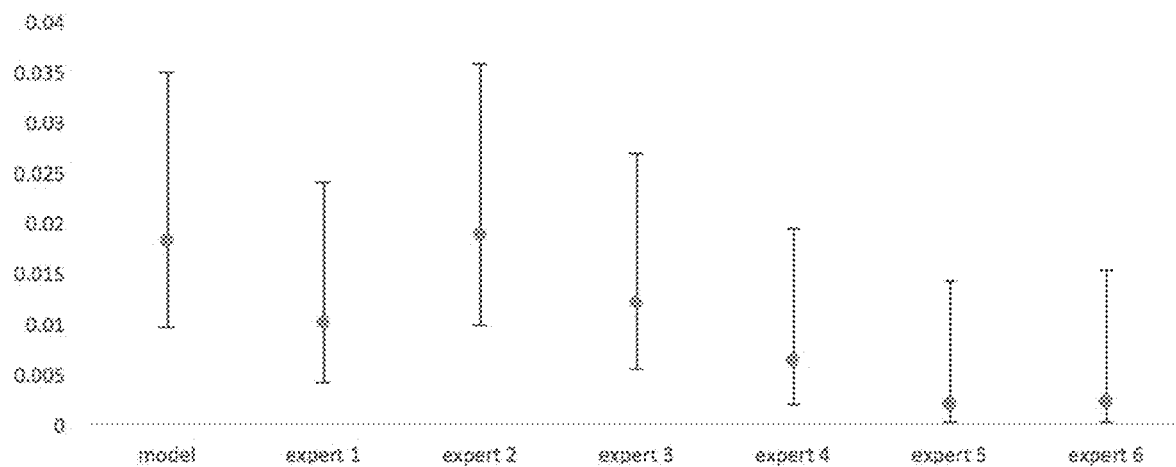

FIG. 9. Plots depicting the positive and negative likelihood ratios with their corresponding 95% confidence intervals marked, related to FIG. 4. (A) The positive likelihood ratio is defined as the true positive rate over the false positive rate, so that an increasing likelihood ratio greater than 1 indicates increasing probability that the predicted result is associated with the disease. (B) The negative likelihood ratio is defined as the false negative rate over the true negative rate, so that a decreasing ratio less than 1 indicates increasing probability that the predicted result is associated with the absence of the disease.

FIG. 10. Proposed Penalties for incorrect Labeling during Weighted Error Calculations and Confusion Matrix of Experts Grading OCT Images, related to FIG. 4. (A) The penalties include an error score of 4 for "urgent referrals" scored as normal and an error score of 2 for "urgent referrals" scored as drusen. Ali other incorrect answers carry an error score of 1. (B) The results for each of the human experts are depicted here, comparing the true labels and the predicted labels for each individual grader.

FIG. 11A-G. (A-F) Horizontal cross-section OCT images through the fovea of patients with wet AMD (A-C) or diabetic retinopathy (D-F) with macular edema: before (left) and after (right) three monthly intravitreal injections of bevacizumab. Intra-retinal or sub-retinal fluid (arrows) lessened after treatment. The visual acuity (VA) of all patients were improved: (A) 20/320 to 20/250, 5 months. (B) 20/40 to 20/32, 9 months, (C) 20/400 to 20/250, 3 months, (D) 20/80 to 20/50, 7 months, (E) 20/40 to 20/25, 7 months, and (F) 20/32 to 20/25, 7 months. (G) Pre-treatment horizontal cross-section OCT images (up, left) of DME patient's left eye showed macular edema (arrows) through macular center and the intra-retinal fluid disappeared after three consecutive anti-VEGF treatment (up, right). VA was improved after 6 months: from 20/70 to 20/25. But a recurrence of macular edema was spotted on OCT after 5 months (down, left, arrows) from the last visit. VA dropped to 20/125. The patient was given three consecutive monthly injections of bevacizumab and the symptom was relieved again (down, right) after 1 month with VA improved to 20/80.

FIG. 12. The diagnosis gateway cloud that can upload and make a diagnosis. It allows uploading of any JPEG OCT image for prompt automatic diagnosis along with the probabilities for each diagnosis.

Figure 13:
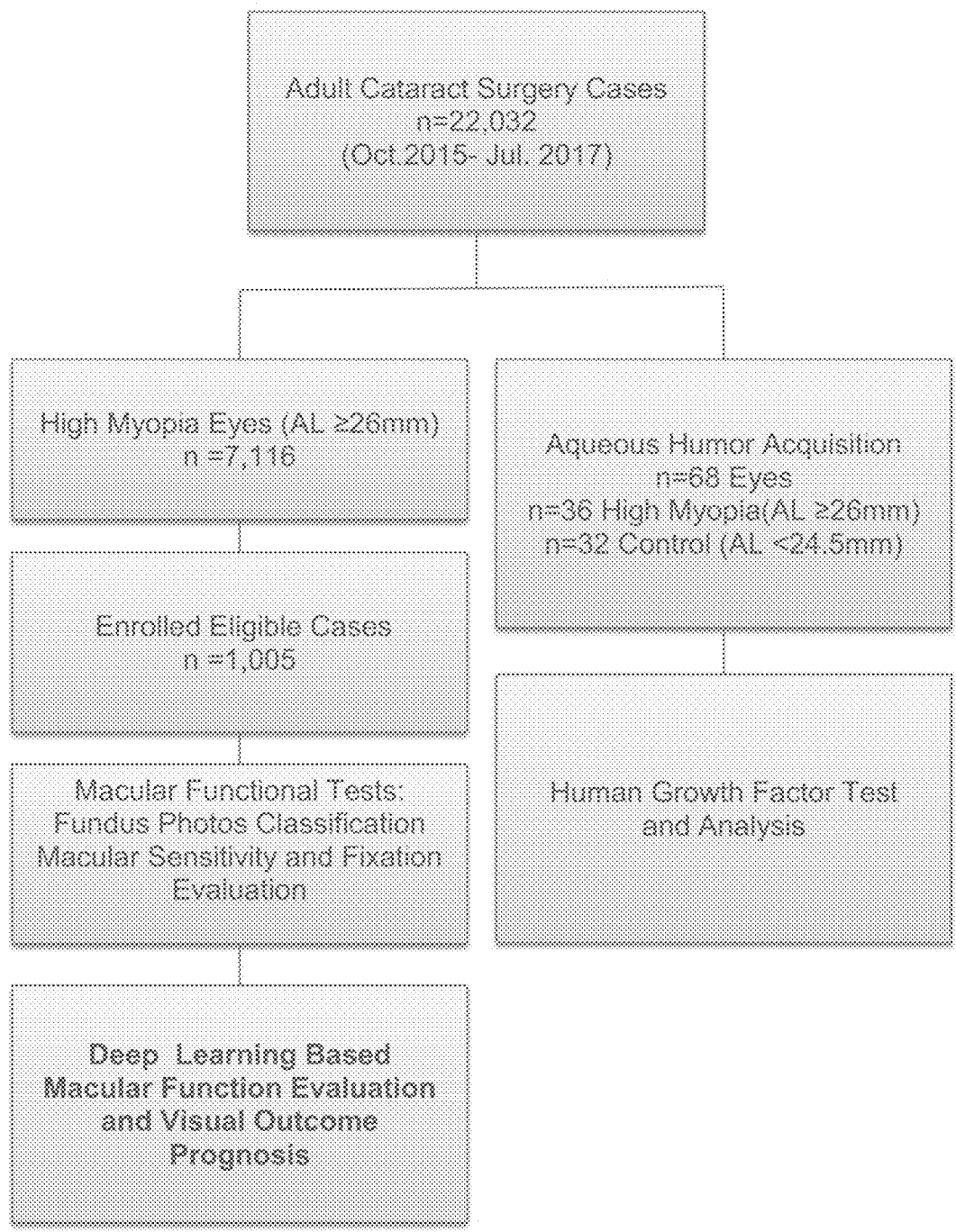
FIG. 13 shows the workflow diagram of an overall experimental design describing the flow of patient enrollment followed by fundus classification and macular functional test, which then underwent machine training and subsequent testing. It was found that long axial length (≥26 mm) may be a risk factor for poor visual prognosis after cataract surgery.

FIG. 13. Workflow diagram showing overall experimental design describing the flow of patient enrollment followed by fundus classification and macular functional test, which then underwent machine training and subsequent testing. It was found that long axial length ($\geq 26$ mm) may be a risk factor for poor visual prognosis after cataract surgery.

Figure 14A:
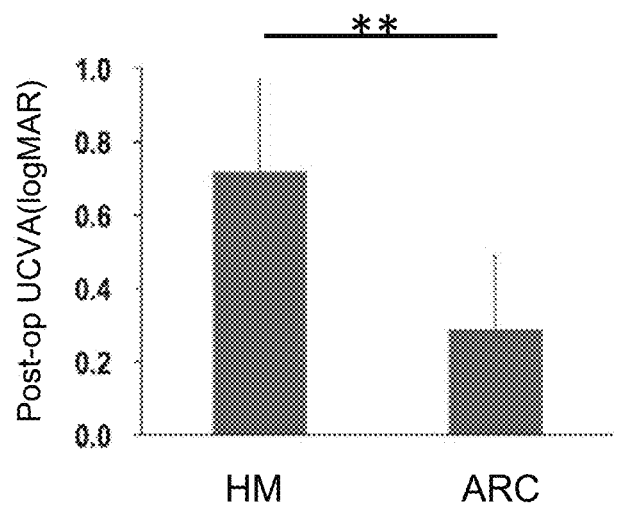
FIG. 14A-B shows postoperative visual outcomes were noted to be significantly poorer in eyes with longer axial lengths.
Figure 14B:
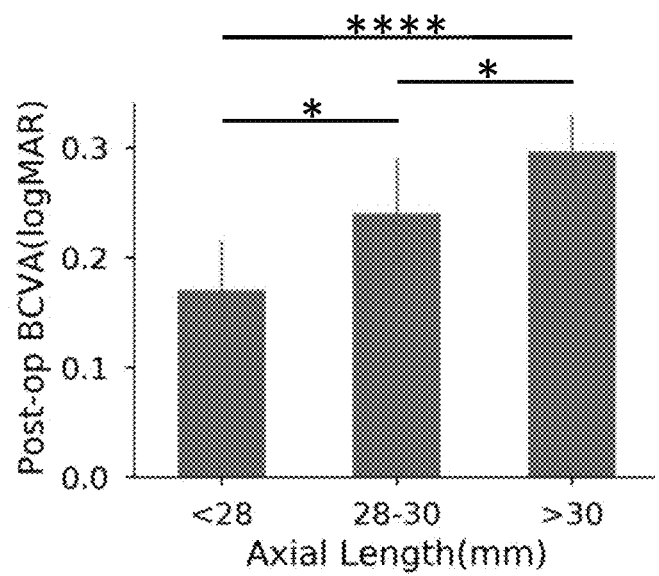
Figure 15E:
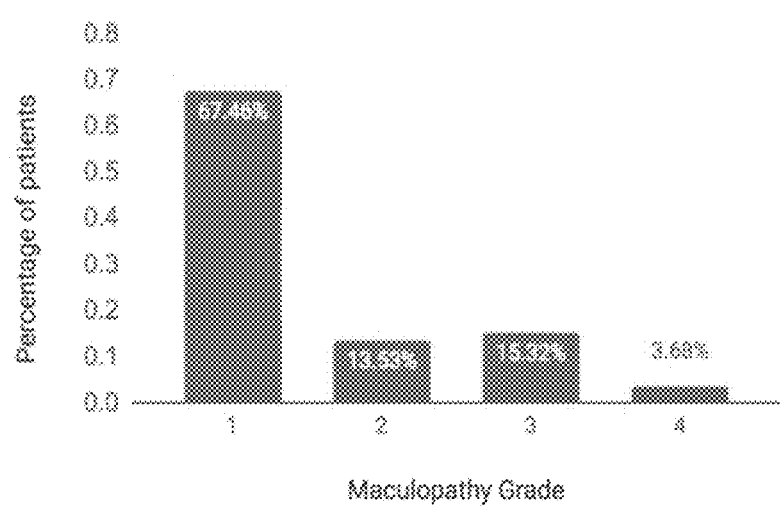
FIG. 15E shows the percentage of patients within the highly myopic maculopathy categories 1-4, respectively.

FIG. 14A-B. Postoperative visual outcomes were noted to be significantly poorer in eyes with longer axial lengths. (A) Within all the adult cataract cases, postoperative visual outcomes were poorer in eyes with longer axial lengths ($\geq 26$ mm) than in eyes with axial lengths<24.5 mm. The average post-operative UCVA(log MAR) visual acuity of 0.71 vs. 0.29 after surgery, *-$p<0.001$; UCVA=uncorrected visual acuity; HMC=high myopic cataract; ARC=age related cataract;). (B) Among the 1,005 enrolled patients, postoperative visual outcomes were noted to be significantly poorer in eyes with longer axial lengths (>30 mm) than in eyes with axial lengths<30 mm. (Average post-operative BCVA(log MAR) visual acuity: AL<28 mm=$0.17\pm0.38$ (325); 28 mm$\leq$AL$\leq$30 mm=$0.24\pm0.41$(292); AL>30 mm=$0.30\pm0.31$ (388); ANOVA followed by Tukey test: $p<0.0001$; AL<28 mm vs AL>30 mm, $p<0.0001$; AL<28 mm vs 28 mm$\leq$AL$\leq$30 mm, $p=0.03$; 28 mm$\leq$AL$\leq$30 mm vs AL>30 mm, $p=0.04$; **-$p<0.0001$; *-$p<0.05$; BCVA=best corrected visual acuity)

FIG. 15A-E. Samples of fundus images grading. (A-D) Fundus images of the patients showing myopic maculopathy of different disease categories compared with the existing International Photographic Classification and Grading System for myopic maculopathy: category 1, tessellated fundus (A); category 2, diffuse chorioretinal atrophy (B); category 3, patchy chorioretinal atrophy (C); category 4, macular atrophy (D). (E) Percentage of patients within the highly myopic maculopathy categories 1-4, respectively. Category 1: 67.46% (678/1,005); category 2: 13.53% (136/1,005); category 3: 15.32% (154/1,005); category 4: 3.68% (37/1,005).

FIG. 16A-F. Patient with the island-like macular atrophy pattern and their post-operative visual outcome (A-C) and correlations of macular sensitivity, axial length and BCEA among all patients (D-F). (A) Ultra-widefield retinal image showing island-like macular atrophy. (B) Microperimeter image including the fixation BCEA and mean macular sensitivity. The dark area in the macular grid indicates the dysfunctional area of atrophy, and the fixation ellipse is located on a very small area of remaining macular tissue. BCEA=bivariate contour ellipse area. (C) Among all the patients in category 3, postoperative visual outcomes were poorer in eyes with island-like macular atrophy pattern (14 out of 154) than the eyes within the category. The average post-operative BCVA(log MAR) visual acuity of 0.54 vs. 0.36 after surgery, *-$p<0.05$, t-test; BCVA=best corrected visual acuity). (D) Correlations between MS and axial length (Pearson's correlation: r=−0.34, P<0.001, f-test). (E) Correlations between MS and BCEA. (r=−0.32, P<0.001, f-test). (F) Correlations between BCEA and axial length. (r=0.13, P<0.001, f-test) MS=mean sensitivity; BCEA=bivariate contour ellipse area.

Figure 17:
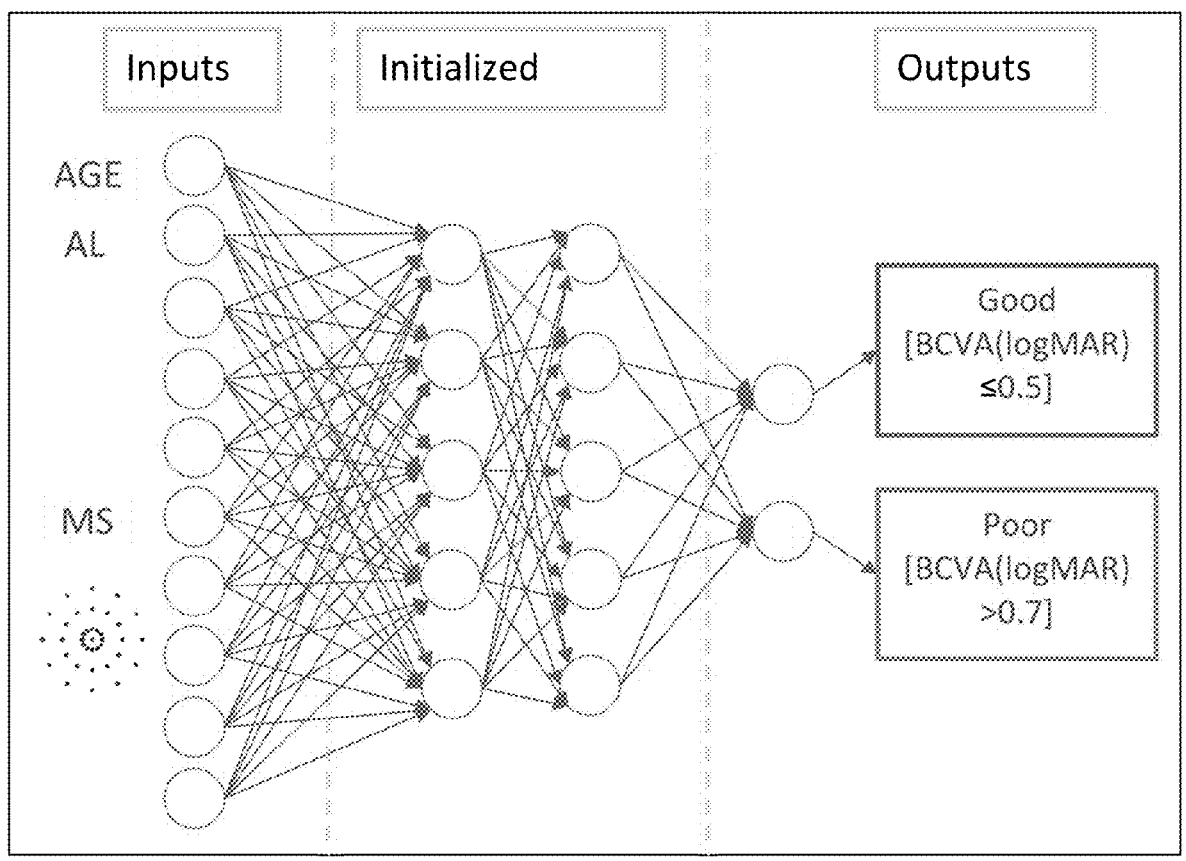
FIG. 17 shows a schematic of a deep neural network.
Figure 19A:
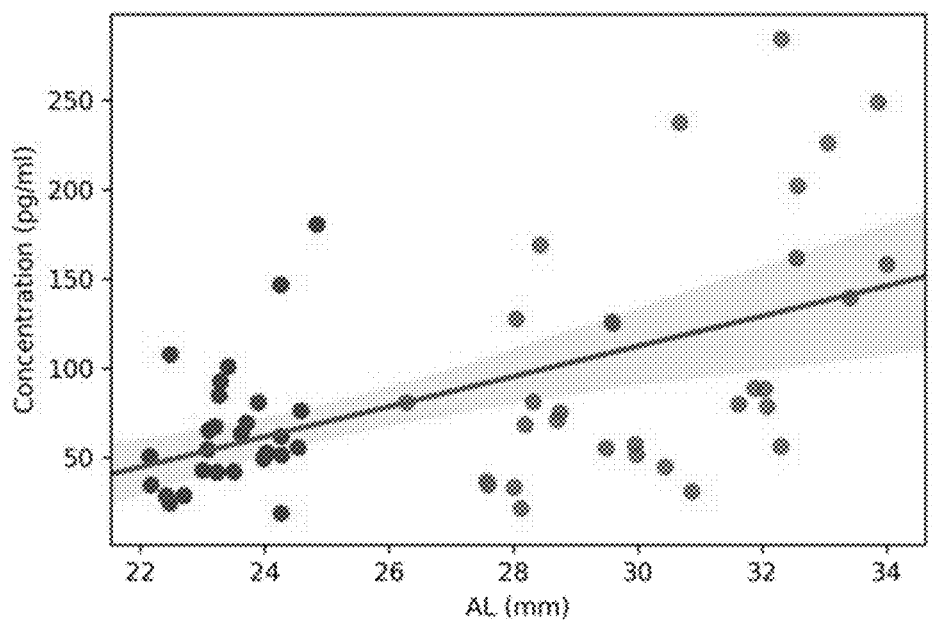
FIG. 19A-D shows scatterplots showing correlations between growth factor level in aqueous humor and axial length.
Figure 19B:
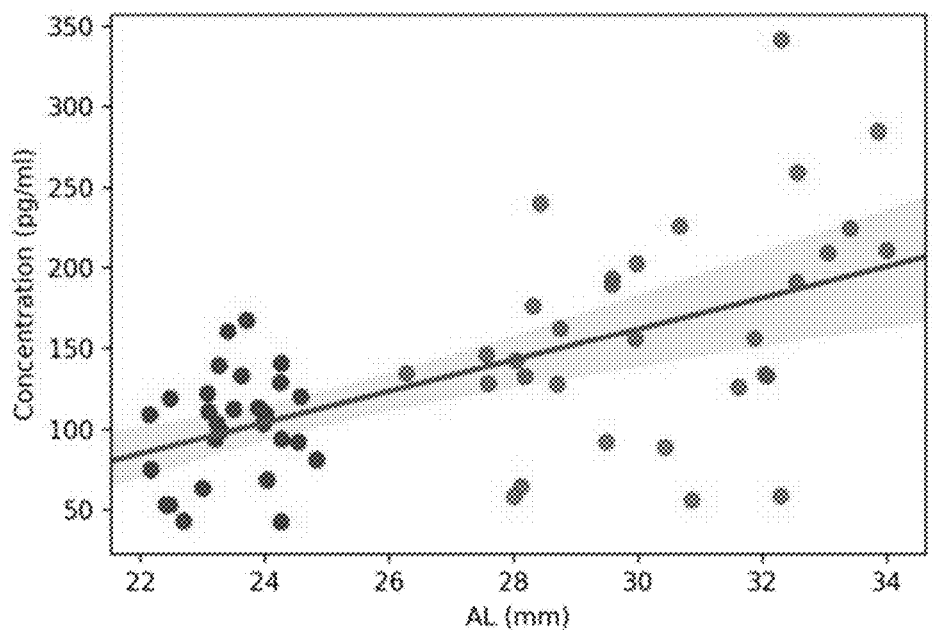
Figure 19C:
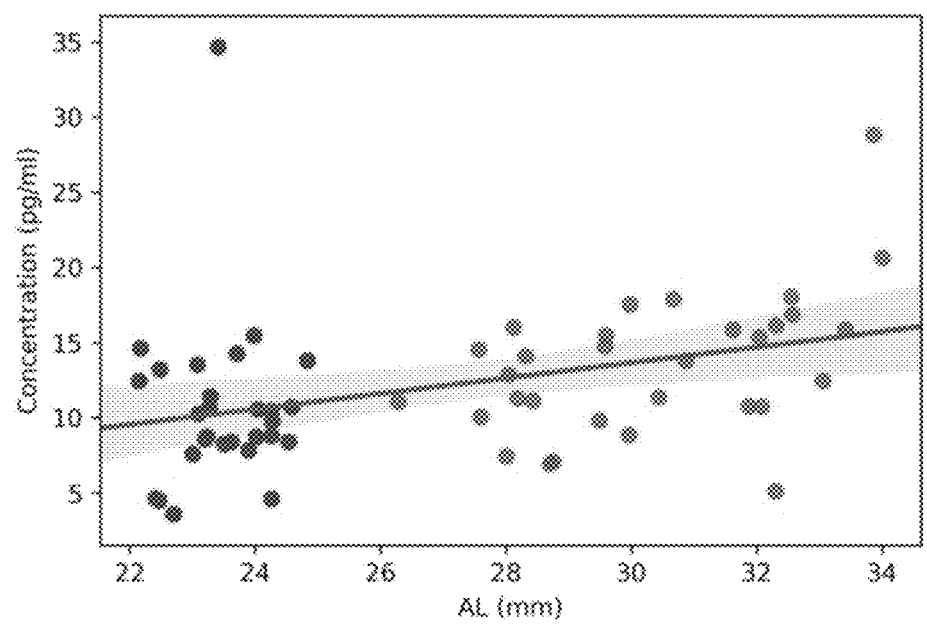
Figure 19D:
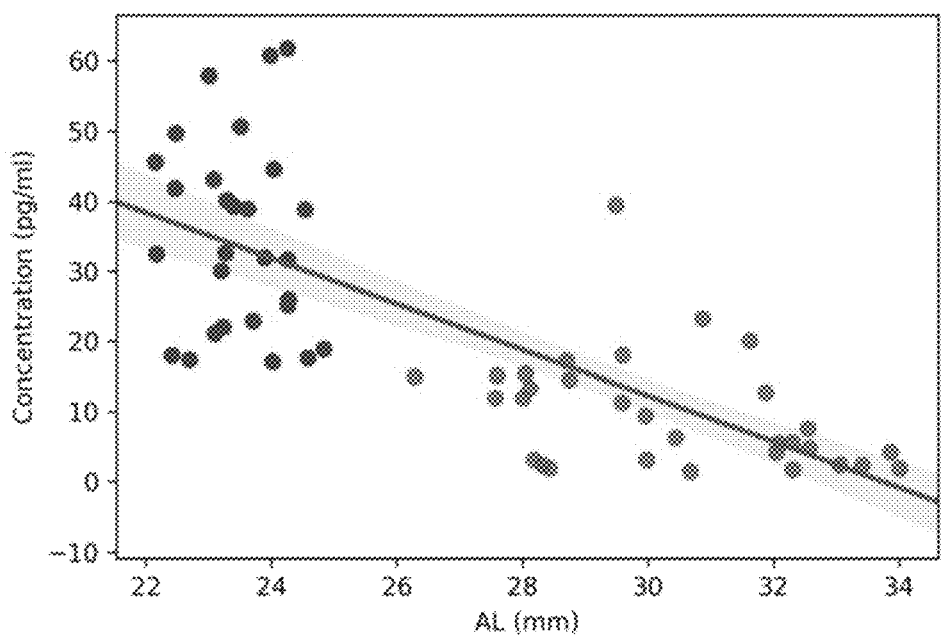

FIG. 17. Schematic of a Deep Neural Network. A total of 1,005 patient microperimeter results were exported and collected, resulting in 177 points covering all the images. Also age (year) and axial length (mm) information were incorporated into the model. A two layer hierarchical neural network was built and validated with 5 neurons in each layer to predict patient post-surgery visual acuity. Patients with high confident diagnosis, defining patients with post-op BCVA(log MAR) less than or equal to 0.5 as negative instances (patients with high confident as having good vision), and patients with post-op BCVA(log MAR) more than 0.5 as positive instances (patients with high confident as having poor vision).

FIG. 18A-D. Plots Showing Performance of the Deep Learning Model. (A) First principal component (PC0) of macular sensitivity images tracks patient post-operation BCVA(log MAR) visual acuity level. PC0 (y-axis) correlates with post-operation BCVA(log MAR) level (R=0.48, p<1e-16, f-test). (B) Using PC0 of threshold image to classify patients' post-op BCVA(log MAR) with high accuracy (ROC-AUC=0.851). (C) Tracking accuracy (y-axis) changes of neural net in both training (red, n=502) and testing cohort (blue, n=503) with respect to number of 10,000 training steps (x-axis). The final model yield an accuracy of 0.931. (D) Classification accuracy of model in validation cohort using the trained hierarchical neural network. The area under the ROC curve for prognosing post-op visual acuity was 0.918.

FIG. 19A-D. Scatterplots showing correlations between growth factor level in aqueous humor and axial length. (A) Growth differentiation factor-15 (GDF-15) level in aqueous humor was positively correlated with axial length (Spearman coefficient=0.503, P<0.001, Spearman correlation analysis). (B) Hepatocyte growth factor (HGF) level in aqueous humor was positively correlated with axial length (Spearman coefficient=0.567, P<0.001, Spearman correlation analysis). (C) Platelet derived growth factor (PDGF-AA) level in aqueous humor was positively correlated with axial length (Spearman coefficient=0.458, P<0.001, Spearman correlation analysis). (D) Vascular endothelial growth factor (VEGF) level in aqueous humor was negatively correlated with axial length (Spearman coefficient=−0.777, P<0.001, Spearman correlation analysis).

Figure 20A:
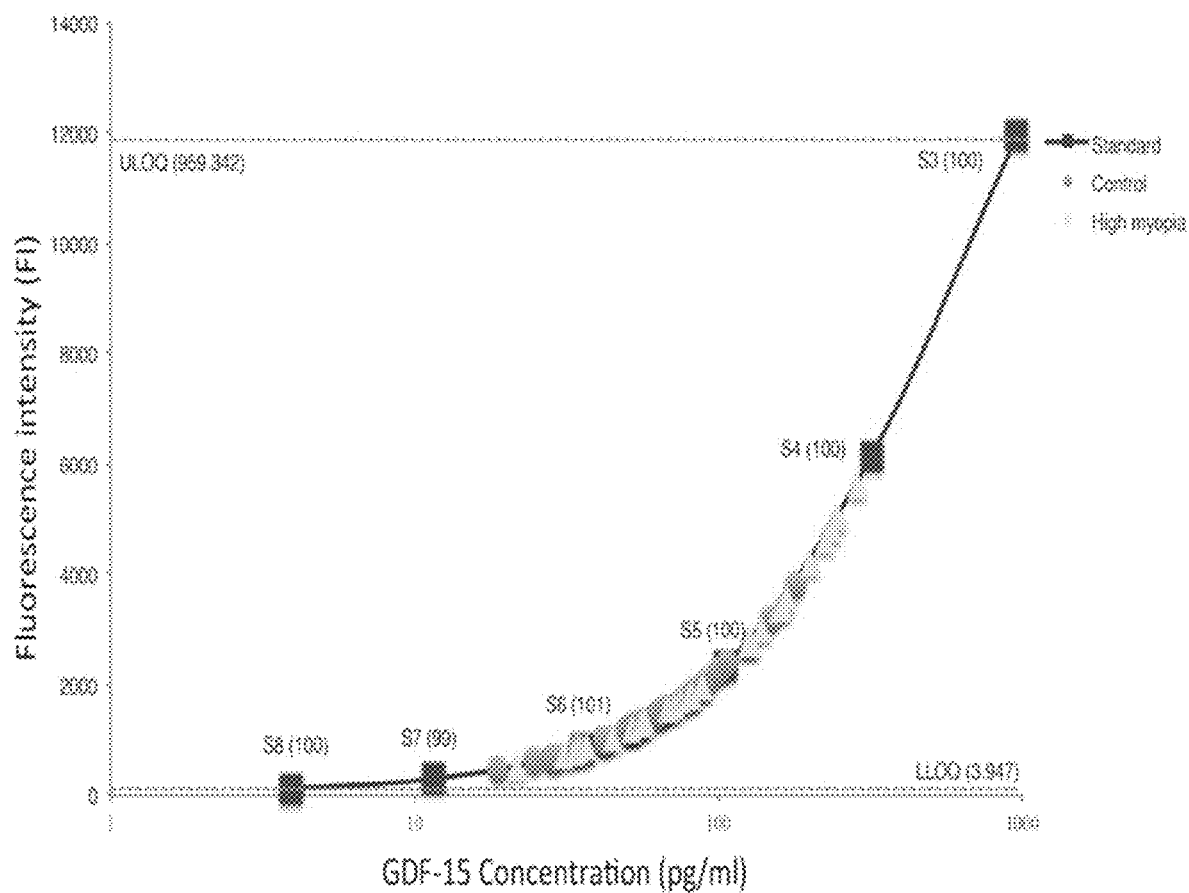
FIG. 20A-C shows the standard curves for detected cytokines in a Bio-Plex Pro™ multiplex bead-based immunoassay.
Figure 20B:
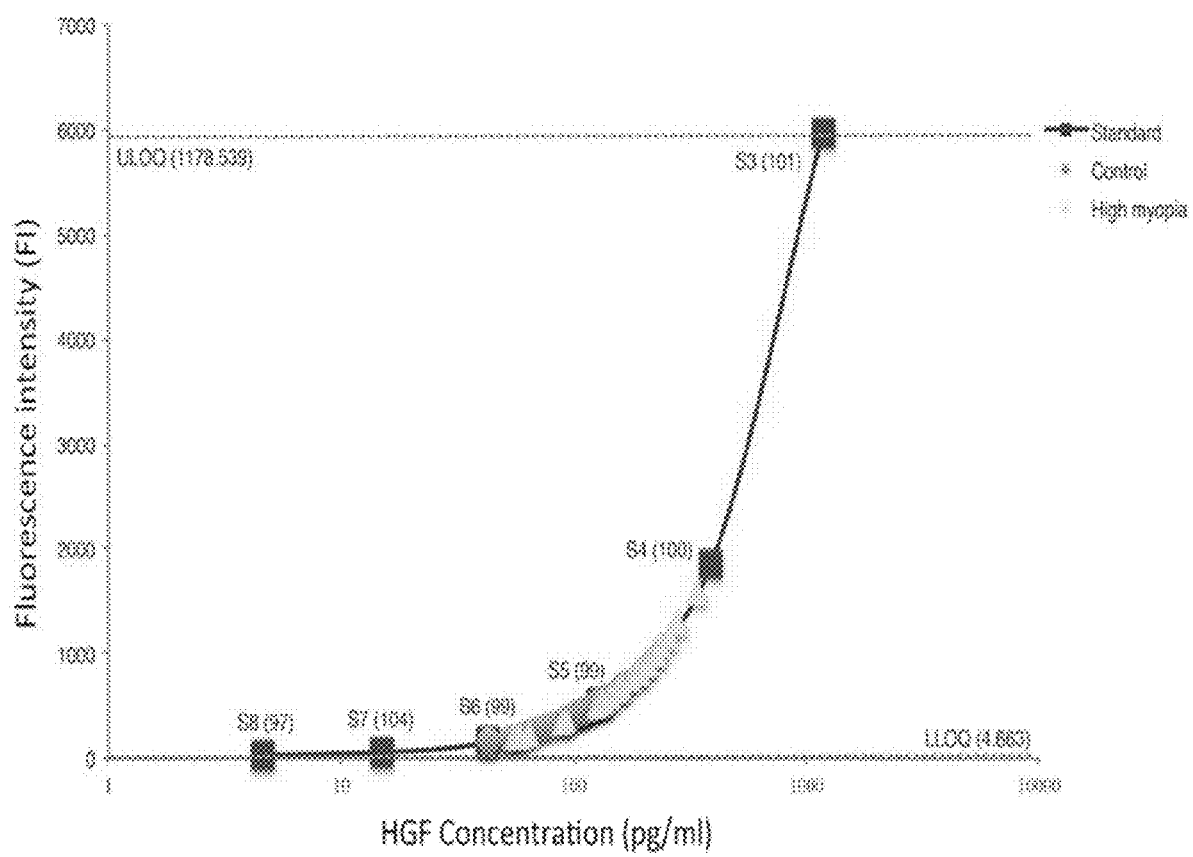
Figure 20C:
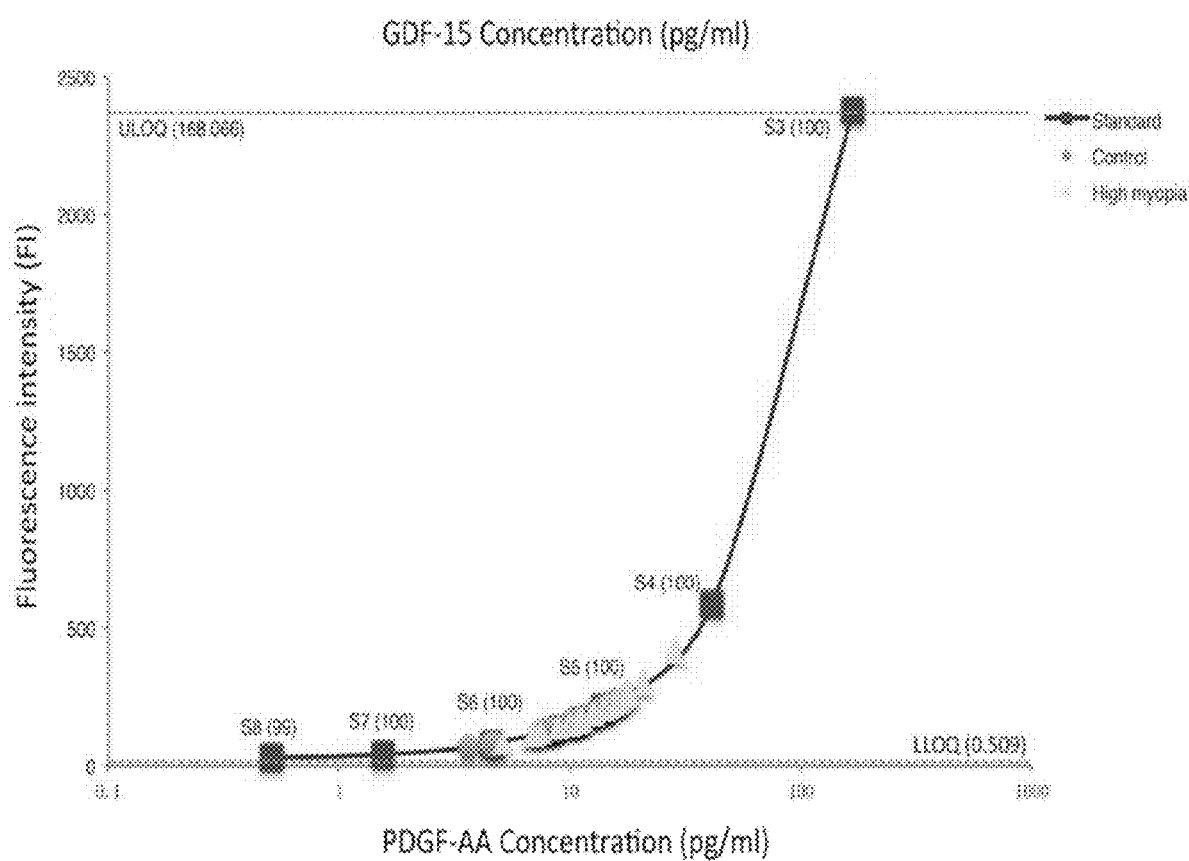

FIG. 20A-C. The standard curves for detected cytokines in Bio-Plex Pro™ multiplex bead-based immunoassay. (The X-axis scale is not linear and the figure is in semi-log scale). (A) GDF-15: growth differentiation factor-15; (B) HGF: hepatocyte growth factor; (C) PDGF-AA: platelet-derived growth factor; ULOQ: upper limit of quantification; LLOQ: lower limit of quantification.

Figure 21:
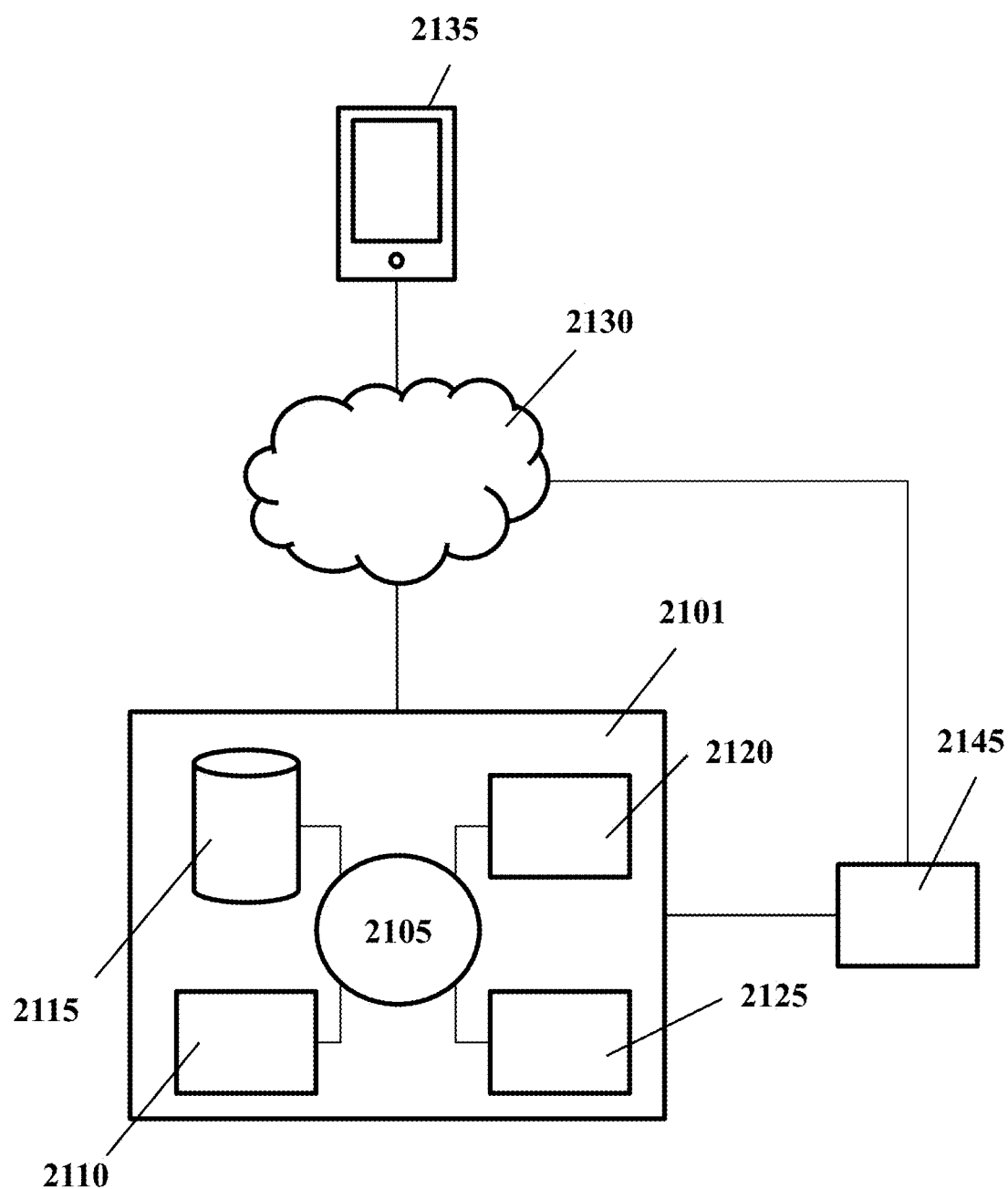
FIG. 21 schematically illustrates a computer control system or platform that is programmed or otherwise configured to implement methods provided herein.

FIG. 21 schematically illustrates a computer control system or platform that is programmed or otherwise configured to implement methods provided herein. In some embodiments, the system comprises a computer system 2101 that is programmed or otherwise configured to carry out executable instructions such as for carrying out image analysis. The computer system includes at least one CPU or processor 2105. The computer system includes at least one memory or memory location 2110 and/or at least one electronic storage unit 2115. In some embodiments, the computer system comprises a communication interface 2120 (e.g. network adaptor). In some embodiments, the computer system 2101 can be operatively coupled to a computer network ("network") 2130 with the aid of the communication interface 2120. In some embodiments, an end user device 2135 is used for uploading medical data such as ophthalmic images, general browsing of the database 2145, or performance of other tasks. In some embodiments, the database 2145 is one or more databases separate from the computer system 2101.

FIG. 22 shows a diagram of one embodiment of an electronic device such as a cell phone or smartphone 2202 attached to a portable device 2201 having an imaging component 2203 (e.g., ophthalmoscope) with one or more lenses 2204 that is configured for alignment with a camera lens 2205 of the electronic device 2202. The diagram shows the rear view of the phone (not facing the touchscreen) with the ophthalmoscope positioned over the rear facing camera. The dashed lines indicate the object is covered or obscured by another object.

Numbered Embodiments

The disclosure is further elucidated by reference to the numbered embodiments herein. 1. A method for providing a medical diagnosis, comprising: a) obtaining a medical image; b) performing a machine learning procedure on the medical image; and c) determining, by the machine learning procedure, whether or not the medical image is indicative of a medical disease or disorder, the determination having a sensitivity greater than 90% and a specificity greater than 90%. 2. The method of embodiment 1, wherein the machine learning procedure comprises a deep learning procedure. 3. The method of embodiment 1 or 2, wherein the machine learning procedure comprises training a convolutional neural network. 4. The method of any of embodiments 1-3, further comprising subjecting the medical image to an image occlusion procedure. 5. The method of any of embodiments 1-4, further comprising performing a transfer learning procedure. 6. The method of embodiment 5, wherein the transfer learning procedure comprises pre-training the machine learning procedure using non-medical images obtained from a large image dataset to obtain a pre-trained machine learning procedure. 7. The method of embodiment 6, wherein the transfer learning procedure further comprises training the pre-trained machine learning procedure using a set of medical images that is smaller than the large image dataset. 8. The method of any one of embodiments 1-7, further comprising making a medical treatment recommendation based on the determination. 9. The method of any one of embodiments 1-8, wherein the medical image is an ophthalmic image that conveys information about the presence or absence of an ophthalmic disease or disorder. 10. The method of embodiment 9, wherein the ophthalmic image is a retinal image. 11. The method of embodiment 9 or 10, wherein the ophthalmic image is an optical coherence tomography (OCT) image. 12. The method of embodiment 10 or 11, wherein the ophthalmic disease or disorder is selected from the group consisting of: age-related macular degeneration (AMD), diabetic macular edema (DME), and choroidal neovascularization (CNV). 13. A non-transitory computer-readable medium comprising machine-executable code that, upon execution by one or more computer processors, implements a method for providing a medical diagnosis, the method comprising: a) obtaining a medical image; b) performing a machine learning procedure on the medical image; and c) determining, by the machine learning procedure, whether or not the medical image is indicative of a medical disease or disorder, the determination having a sensitivity greater than 90% and a specificity greater than 90%. 14. The non-transitory computer-readable medium of embodiment 13, wherein the machine learning procedure comprises a deep learning procedure. 15. The non-transitory computer-readable medium of embodiment 13 or 14, wherein the machine learning procedure comprises training a convolutional neural network. 16. The non-transitory computer-readable medium of any of embodiments 13-15, wherein the method further comprises subjecting the medical image to an image occlusion procedure. 17. The non-transitory computer-readable medium of any of embodiments 13-16, wherein the method further comprises performing a transfer learning procedure. 18. The non-transitory computer-readable medium of embodiment 17, wherein the transfer learning procedure comprises pre-training the machine learning procedure using non-medical images obtained from a large image dataset to obtain a pre-trained machine learning procedure. 19. The non-transitory computer-readable medium of embodiment 18, wherein the transfer learning procedure further comprises training the pre-trained machine learning procedure using a set of medical images that is smaller than the large image dataset. 20. The non-transitory computer-readable medium of any one of embodiments 13-19, wherein the method further comprises making a medical treatment recommendation based on the determination. 21. The non-transitory computer-readable medium of any one of embodiments 13-20, wherein the medical image is an ophthalmic image that conveys information about the presence or absence of an ophthalmic disease or disorder. 22. The non-transitory computer-readable medium of embodiment 21, wherein the ophthalmic image is a retinal image. 23. The non-transitory computer-readable medium of embodiment 21 or 22, wherein the ophthalmic image is an optical coherence tomography (OCT) image. 24. The non-transitory computer-readable medium of embodiment 22 or 23, wherein the ophthalmic disease or disorder is selected from the group consisting of: age-related macular degeneration (AMD), diabetic macular edema (DME), and choroidal neovascularization (CNV). 25. A computer-implemented system comprising: a digital processing device comprising: at least one processor, an operating system configured to perform executable instructions, a memory, and a computer program including instructions executable by the digital processing device to create an application for providing a medical diagnosis, the application comprising: a) a software module for obtaining a medical image; b) a software module for performing a machine learning procedure on the medical image; and c) a software module for determining, by the machine learning procedure, whether or not the medical image is indicative of a medical disease or disorder, the determination having a sensitivity greater than 90% and a specificity greater than 90%. 26. The computer-implemented system of embodiment 25, wherein the machine learning procedure comprises a deep learning procedure. 27. The computer-implemented system of embodiment 25 or 26, wherein the machine learning procedure comprises training a convolutional neural network. 28. The computer-implemented system of any of embodiments 25-27, wherein the application further comprises a software module for subjecting the medical image to an image occlusion procedure. 29. The computer-implemented system of any of embodiments 25-28, wherein the application further comprises a software module for performing a transfer learning procedure. 30. The computer-implemented system of embodiment 29, wherein the transfer learning procedure comprises pre-training the machine learning procedure using non-medical images obtained from a large image dataset to obtain a pre-trained machine learning procedure. 31. The computer-implemented system of embodiment 30, wherein the transfer learning procedure further comprises training the pre-trained machine learning procedure using a set of medical images that is smaller than the large image dataset. 32. The computer-implemented system of any one of embodiments 25-31, wherein the application further comprises a software module for making a medical treatment recommendation based on the determination. 33. The computer-implemented system of any one of embodiments 25-32, wherein the medical image is an ophthalmic image that conveys information about the presence or absence of an ophthalmic disease or disorder. 34. The computer-implemented system of embodiment 33, wherein the ophthalmic image is a retinal image. 35. The computer-implemented system of embodiment 33 or 34, wherein the ophthalmic image is an optical coherence tomography (OCT) image. 36. The computer-implemented system of embodiment 34 or 35, wherein the ophthalmic disease or disorder is selected from the group consisting of: age-related macular degeneration (AMD), diabetic macular edema (DME), and choroidal neovascularization (CNV). 37. A method for providing a medical diagnosis, comprising: a) obtaining a medical image; b) analyzing the medical image with a machine learning procedure; and c) generating, by the machine learning procedure, a prediction of visual acuity based on the medical image, the prediction having a sensitivity greater than 90% and a specificity greater than 90%. 38. The method of embodiment 37, wherein the machine learning procedure comprises a deep learning procedure. 39. The method of embodiment 37 or 38, wherein the machine learning procedure comprises training a convolutional neural network. 40. The method of embodiment 39, wherein the convolutional neural network has no more than 5 neurons per layer. 41. The method of any of embodiments 37-40, wherein the machine learning procedure utilizes inputs comprising age, axial length, and macular sensitivity. 42. The method of any one of embodiments 37-41, further comprising making a medical treatment recommendation based on the determination. 43. The method of any one of embodiments 37-42, wherein the medical image is an ophthalmic image that conveys information about the presence or absence of an ophthalmic disease, disorder, or condition. 44. The method of embodiment 43, wherein the ophthalmic image is an optical coherence tomography (OCT) image. 45. The method of embodiment 43, wherein the ophthalmic image is a macular sensitivity threshold image. 46. The method of any of embodiments 43-45, wherein the ophthalmic disease, disorder, or condition is selected from the group consisting of: age-related macular degeneration (AMD), diabetic macular edema (DME), choroidal neovascularization (CNV), chorioretinal atrophy, foveoschisis, intra-operative vitreous loss, postoperative retinal tear or detachment, and posterior staphyloma. 47. A non-transitory computer-readable medium comprising machine-executable code that, upon execution by one or more computer processors, implements a method for providing a medical diagnosis, the method comprising: a) obtaining a medical image; b) analyzing the medical image with a machine learning procedure; and c) generating, by the machine learning procedure, a prediction of visual acuity based on the medical image, the prediction having a sensitivity greater than 90% and a specificity greater than 90%. 48. The non-transitory computer-readable medium of embodiment 47, wherein the machine learning procedure comprises a deep learning procedure. 49. The non-transitory computer-readable medium of embodiment 47 or 48, wherein the machine learning procedure comprises training a convolutional neural network. 50. The non-transitory computer-readable medium of embodiment 49, wherein the convolutional neural network has no more than 5 neurons per layer. 51. The non-transitory computer-readable medium of any of embodiments 47-50, wherein the machine learning procedure utilizes inputs comprising age, axial length, and macular sensitivity. 52. The non-transitory computer-readable medium of any one of embodiments 47-51, wherein the method further comprises making a medical treatment recommendation based on the prediction. 53. The non-transitory computer-readable medium of any one of embodiments 47-52, wherein the medical image is an ophthalmic image that conveys information about the presence or absence of an ophthalmic disease, disorder, or condition. 54. The non-transitory computer-readable medium of embodiment 53, wherein the ophthalmic image is a retinal image. 55. The non-transitory computer-readable medium of embodiment 53 or 54, wherein the ophthalmic image is an optical coherence tomography (OCT) image. 56. The non-transitory computer-readable medium of embodiment 53-55, wherein the ophthalmic image is a macular sensitivity threshold image. 57. The non-transitory computer-readable medium of embodiment 53-56, wherein the ophthalmic disease, disorder, or condition is selected from the group consisting of: age-related macular degeneration (AMD), diabetic macular edema (DME), choroidal neovascularization (CNV), chorioretinal atrophy, foveoschisis, intra-operative vitreous loss, postoperative retinal tear or detachment, and posterior staphyloma. 58. A computer-implemented system comprising: a digital processing device comprising: at least one processor, an operating system configured to perform executable instructions, a memory, and a computer program including instructions executable by the digital processing device to create an application for providing a medical diagnosis, the application comprising: a) a software module obtaining a medical image; b) a software module analyzing the medical image with a machine learning procedure; and c) a software module using a machine learning procedure to generate a prediction of visual acuity based on the medical image, the prediction having a sensitivity greater than 90% and a specificity greater than 90%. 59. The computer-implemented system of embodiment 58, wherein the machine learning procedure comprises a deep learning procedure. 60. The computer-implemented system of embodiment 58 or 59, wherein the machine learning procedure comprises training a convolutional neural network. 61. The computer-implemented system of embodiment 60, wherein the convolutional neural network has no more than 5 neurons per layer. 62. The computer-implemented system of any of embodiments 58-61, wherein the machine learning procedure utilizes inputs comprising age, axial length, and macular sensitivity. 63. The computer-implemented system of any one of embodiments 58-62, wherein the application further comprises a software module for making a medical treatment recommendation based on the determination. 64. The computer-implemented system of any one of embodiments 58-63, wherein the medical image is an ophthalmic image that conveys information about the presence or absence of an ophthalmic disease, disorder, or condition. 65. The computer-implemented system of embodiment 64, wherein the ophthalmic image is a retinal image. 66. The computer-implemented system of embodiment 64 or 65, wherein the ophthalmic image is an optical coherence tomography (OCT) image. 67. The computer-implemented system of embodiment 64-66, wherein the ophthalmic disease or disorder is selected from the group consisting of: age-related macular degeneration (AMD), diabetic macular edema (DME), choroidal neovascularization (CNV), chorioretinal atrophy, foveoschisis, intra-operative vitreous loss, postoperative retinal tear or detachment, and posterior staphyloma. 68. A computer-implemented method for providing a medical diagnosis, comprising: a) obtaining medical data for an individual; b) performing a machine learning procedure on the medical data; and c) generating, by the machine learning procedure, a prediction of visual acuity or a visual disorder or condition based on the medical data, the prediction having a sensitivity greater than 90% and a specificity greater than 90%. 69. The method of embodiment 68, wherein the medical data comprises inputs associated with myopia that are processed by the machine learning procedure to generate the prediction of visual acuity. 70. The method of embodiment 68 or 69, wherein the medical data comprises a medical image. 71. The method of embodiment 70, wherein the medical image is an image of a fundus overlaid with microperimetry results. 72. The method of any one of embodiments 68-71, wherein the medical data comprises at least one measure of myopia. 73. The method of any one of embodiments 68-72, wherein the medical data comprises age, axial length, macular sensitivity image, or any combination thereof. 74. The method of any one of embodiments 68-73, wherein the prediction comprises a predicted visual acuity for the individual after cataract surgery. 75. The method of any one of embodiments 68-74, wherein the prediction comprises a diagnostic of good or poor visual acuity for the individual following cataract surgery. 76. The method of any one of embodiments 68-75, wherein the machine learning procedure comprises a deep learning procedure. 77. The method of any one of embodiments 68-76, wherein the machine learning procedure comprises training a convolutional neural network. 78. The method of any one of embodiments 68-77, wherein the transfer learning procedure is trained using a dataset comprising medical images classified into categories of myopic maculopathy. 79. The method of any one of embodiments 68-78, further comprising making a medical treatment recommendation based on the prediction. 80. The method of any one of embodiments 70-71, wherein the medical image is an ophthalmic image that conveys information about the presence or absence of an ophthalmic disease or disorder. 81. The method of embodiment 80, wherein the ophthalmic image is a retinal image. 82. The method of embodiment 80 or 81, wherein the ophthalmic image is an optical coherence tomography (OCT) image. 83. The method of any one of embodiments 80-82, wherein the ophthalmic disease or disorder is selected from the group consisting of: age-related macular degeneration (AMD), diabetic macular edema (DME), and choroidal neovascularization (CNV). 84. The method of any of embodiments 68-83, wherein the prediction comprises a best corrected visual acuity (BCVA). 85. The method of embodiment 84, wherein the machine learning procedure comprises training a machine learning algorithm using outcome classified patient data comprising macular sensitivity, axial length, best corrected visual acuity (BCVA), bivariate contour ellipse area (BCEA), or any combination hereof 86. The method of embodiment 85, wherein the patient data is classified according to at least four categories of myopic maculopathy. 87. A non-transitory computer-readable medium comprising machine-executable code that, upon execution by one or more computer processors, implements a method for providing a medical diagnosis, the method comprising: a) obtaining medical data for an individual; b) performing a machine learning procedure on the medical data; and c) generating, by the machine learning procedure, a prediction of visual acuity or a medical disease or disorder, the prediction having a sensitivity greater than 90% and a specificity greater than 90%. 88. The non-transitory computer-readable medium of embodiment 87, wherein the medical data comprises inputs associated with myopia that are processed by the machine learning procedure to generate the prediction of visual acuity. 89. The non-transitory computer-readable medium of embodiment 87 or 88, wherein the medical data comprises a medical image. 90. The non-transitory computer-readable medium of embodiment 89, wherein the medical image is an image of a fundus overlaid with microperimetry results. 91. The non-transitory computer-readable medium of any one of embodiments 87-90, wherein the medical data comprises at least one measure of myopia. 92. The non-transitory computer-readable medium of any one of embodiments 87-91, wherein the medical data comprises age, axial length, macular sensitivity image, or any combination thereof. 93. The non-transitory computer-readable medium of any one of embodiments 87-92, wherein the prediction comprises a predicted visual acuity for the individual after cataract surgery. 94. The non-transitory computer-readable medium of any one of embodiments 87-93, wherein the prediction comprises a diagnostic of good or poor visual acuity for the individual following cataract surgery. 95. The non-transitory computer-readable medium of any one of embodiments 87-94, wherein the machine learning procedure comprises a deep learning procedure. 96. The non-transitory computer-readable medium of any one of embodiments 87-95, wherein the machine learning procedure comprises training a convolutional neural network. 97. The non-transitory computer-readable medium of any one of embodiments 87-96, wherein the transfer learning procedure is trained using a dataset comprising medical images classified into categories of myopic maculopathy. 98. The non-transitory computer-readable medium of any one of embodiments 87-97, further comprising making a medical treatment recommendation based on the prediction. 99. The non-transitory computer-readable medium of any one of embodiments 89-90, wherein the medical image is an ophthalmic image that conveys information about the presence or absence of an ophthalmic disease or disorder. 100. The non-transitory computer-readable medium of embodiment 99, wherein the ophthalmic image is a retinal image. 101. The non-transitory computer-readable medium of embodiment 99 or 100, wherein the ophthalmic image is an optical coherence tomography (OCT) image. 102. The non-transitory computer-readable medium of any one of embodiments 99-101, wherein the ophthalmic disease or disorder is selected from the group consisting of: age-related macular degeneration (AMD), diabetic macular edema (DME), and choroidal neovascularization (CNV). 103. The non-transitory computer-readable medium of any of embodiments 87-102, wherein the prediction comprises a best corrected visual acuity (BCVA). 104. The non-transitory computer-readable medium of embodiment 103, wherein the machine learning procedure comprises training a machine learning algorithm using outcome classified patient data comprising macular sensitivity, axial length, best corrected visual acuity (BCVA), bivariate contour ellipse area (BCEA), or any combination hereof. 105. The non-transitory computer-readable medium of embodiment 105, wherein the patient data is classified according to at least four categories of myopic maculopathy. 106. A computer-implemented system comprising: a digital processing device comprising: at least one processor, an operating system configured to perform executable instructions, a memory, and a computer program including instructions executable by the digital processing device to create an application for providing a medical diagnosis, the application comprising: a) a software module for obtaining medical data for an individual; b) a software module for performing a machine learning procedure on the medical data; and c) a software module for generating, by the machine learning procedure, a prediction of visual acuity or a medical disease or disorder, the prediction having a sensitivity greater than 90% and a specificity greater than 90%. 107. The computer-implemented system of embodiment 106, wherein the medical data comprises inputs associated with myopia that are processed by the machine learning procedure to generate the prediction of visual acuity. 108. The computer-implemented system of embodiment 106 or 107, wherein the medical data comprises a medical image. 109. The computer-implemented system of embodiment 108, wherein the medical image is an image of a fundus overlaid with microperimetry results. 110. The computer-implemented system of any one of embodiments 106-109, wherein the medical data comprises at least one measure of myopia. 111. The computer-implemented system of any one of embodiments 106-110, wherein the medical data comprises age, axial length, macular sensitivity image, or any combination thereof. 112. The computer-implemented system of any one of embodiments 106-111, wherein the prediction comprises a predicted visual acuity for the individual after cataract surgery. 113. The computer-implemented system of any one of embodiments 106-112, wherein the prediction comprises a diagnostic of good or poor visual acuity for the individual following cataract surgery. 114. The computer-implemented system of any one of embodiments 106-113, wherein the machine learning procedure comprises a deep learning procedure. 115. The computer-implemented system of any one of embodiments 106-114, wherein the machine learning procedure comprises training a convolutional neural network. 116. The computer-implemented system of any one of embodiments 106-115, wherein the transfer learning procedure is trained using a dataset comprising medical images classified into categories of myopic maculopathy. 117. The computer-implemented system of any one of embodiments 106-116, further comprising making a medical treatment recommendation based on the prediction. 118. The computer-implemented system of any one of embodiments 116 or 117, wherein the medical image is an ophthalmic image that conveys information about the presence or absence of an ophthalmic disease or disorder. 119. The computer-implemented system of embodiment 118, wherein the ophthalmic image is a retinal image. 120. The computer-implemented system of embodiment 118 or 119, wherein the ophthalmic image is an optical coherence tomography (OCT) image. 121. The computer-implemented system of any one of embodiments 118-120, wherein the ophthalmic disease or disorder is selected from the group consisting of: age-related macular degeneration (AMD), diabetic macular edema (DME), and choroidal neovascularization (CNV). 122. The computer-implemented system of any of embodiments 106-121, wherein the prediction comprises a best corrected visual acuity (BCVA). 123. The computer-implemented system of embodiment 122, wherein the machine learning procedure comprises training a machine learning algorithm using outcome classified patient data comprising macular sensitivity, axial length, best corrected visual acuity (BCVA), bivariate contour ellipse area (BCEA), or any combination hereof. 124. The computer-implemented system of embodiment 123, wherein the patient data is classified according to at least four categories of myopic maculopathy. 125. A computer-implemented system comprising: a) an electronic device comprising: a processor, a memory, a display, a camera, and an operating system configured to perform executable instructions; b) a portable device comprising an imaging component, said portable device configured to receive and position the electronic device to align the camera with the imaging component; and c) a computer program stored in the memory of the electronic device, the computer program including instructions executable by the user electronic device to create an application comprising: i) a software module controlling the camera to capture an ophthalmic image or video of a subject; and ii) a software module determining whether the ophthalmic image or video is indicative of a medical disease or disorder, the determination having a sensitivity greater than 90% and a specificity greater than 90%. 126. The system of embodiment 125, wherein determining whether the ophthalmic image or video is indicative of a medical disease or disorder comprises uploading the ophthalmic image or video to a cloud network to be analyzed by a trained classifier generated using a machine learning procedure. 127. The system of embodiment 125, wherein determining whether the ophthalmic image or video is indicative of a medical disease or disorder comprises analyzing the ophthalmic image or video with a classifier generated using a machine learning procedure. 128. The system of embodiments 126 or 127, wherein the machine learning procedure comprises a deep learning procedure. 129. The system of any of embodiments 126-128, wherein the machine learning procedure comprises training a convolutional neural network. 130. The system of any of embodiments 125-129, wherein the application further comprises a software module displaying the determination. 131. The system of any of embodiments 125-130, wherein the application further comprises a software module subjecting the ophthalmic image or video to an image occlusion procedure. 132. The system of embodiment 131, wherein the software module displaying the determination further displays areas of the ophthalmic image or video identified as significant to the determination by the image occlusion procedure. 133. The system of any of embodiments 126-132, wherein the machine learning procedure further comprises a transfer learning procedure. 134. The system of embodiment 133, wherein the transfer learning procedure comprises pre-training an untrained classifier using non-medical images obtained from a large image dataset to obtain a pre-trained classifier. 135. The system of embodiment 134, wherein the transfer learning procedure further comprises training the pre-trained classifier using a set of medical images that is smaller than the large image dataset to obtain the trained classifier. 136. The system of any one of embodiments 125-135, wherein the application further comprises a software module making a medical treatment recommendation based on the determination. 137. The system of any one of embodiments 125-136, wherein the ophthalmic image or video conveys information about a presence or absence of an ophthalmic disease or disorder. 138. The system of any one of embodiments 125-137, wherein the ophthalmic image is a retinal image. 139. The system of any one of embodiments 125-138, wherein the ophthalmic image is an optical coherence tomography (OCT) image. 140. The system of embodiment 137, wherein the ophthalmic disease or disorder is selected from the group consisting of: age-related macular degeneration (AMD), diabetic macular edema (DME), and choroidal neovascularization (CNV). 141. The system of any one of embodiments 125-140, wherein the imaging component is an ophthalmoscope enabling the camera to capture the ophthalmic image or video from an eye of a subject. 142. The system of embodiment 141, wherein the portable device comprises an adaptor configured to receive and position the electronic device. 143. The system of any of embodiments 125-142, further comprising a network server receiving the ophthalmic image or video uploaded by the electronic device, analyzing the ophthalmic image or video with a trained classifier to obtain the determination, and providing the determination to the electronic device. 144. The system of any of embodiments 125-143, wherein the application further comprises a software module stitching together screenshots of the ophthalmic video to generate a composite ophthalmic image. 145. A computer-implemented system comprising: a) a medical imaging device configured to capture an ophthalmic image of a subject; b) an electronic device operatively coupled to the medical imaging device, comprising: a processor, a memory, a display, and an operating system configured to perform executable instructions; c) a computer program stored in the memory of the electronic device, the computer program including instructions executable by the user electronic device to create an application comprising: iii) a software module controlling the medical imaging device to capture the ophthalmic image of the subject; and iv) a software module determining whether the ophthalmic image is indicative of a medical disease or disorder, the determination having a sensitivity greater than 90% and a specificity greater than 90%. 146. The system of embodiment 145, wherein determining whether the ophthalmic image is indicative of a medical disease or disorder comprises uploading the ophthalmic image to a cloud network to be analyzed by a trained classifier generated using a machine learning procedure. 147. The system of embodiment 145, wherein determining whether the ophthalmic image is indicative of a medical disease or disorder comprises analyzing the ophthalmic image with a classifier generated using a machine learning procedure. 148. The system of embodiments 146 or 147, wherein the machine learning procedure comprises a deep learning procedure. 149. The system of any of embodiments 146-148, wherein the machine learning procedure comprises training a convolutional neural network. 150. The system of any of embodiments 145-149, wherein the application further comprises a software module displaying the determination. 151. The system of any of embodiments 145-150, wherein the application further comprises a software module subjecting the ophthalmic image or video to an image occlusion procedure. 152. The system of embodiment 151, wherein the software module displaying the determination further displays areas of the ophthalmic image identified as significant to the determination by the image occlusion procedure. 153. The system of any of embodiments 146-152, wherein the machine learning procedure further comprises a transfer learning procedure. 154. The system of embodiment 153, wherein the transfer learning procedure comprises pre-training an untrained classifier using non-medical images obtained from a large image dataset to obtain a pre-trained classifier. 155. The system of embodiment 154, wherein the transfer learning procedure further comprises training the pre-trained classifier using a set of medical images that is smaller than the large image dataset to obtain the trained classifier. 156. The system of any one of embodiments 145-155, wherein the application further comprises a software module making a medical treatment recommendation based on the determination. 157. The system of any one of embodiments 145-156, wherein the ophthalmic image conveys information about a presence or absence of an ophthalmic disease or disorder. 158. The system of any one of embodiments 145-157, wherein the ophthalmic image is a retinal image. 159. The system of any one of embodiments 145-158, wherein the ophthalmic image is an optical coherence tomography (OCT) image. 160. The system of embodiment 157, wherein the ophthalmic disease or disorder is selected from the group consisting of: age-related macular degeneration (AMD), diabetic macular edema (DME), and choroidal neovascularization (CNV). 161. The system of any one of embodiments 145-160, wherein the medical imaging device is an optical coherence tomography (OCT) device. 162. The system of any of embodiments 145-161, further comprising a network server receiving the ophthalmic image uploaded by the electronic device, analyzing the ophthalmic image or video with a trained classifier to obtain the determination, and providing the determination to the electronic device. 163. The system of any of embodiments 145-162, wherein the system is configured as a self-service kiosk. 164. The system of embodiment 163, wherein the kiosk comprises a positioning component for positioning a head of a subject in front of the medical imaging device to capture the ophthalmic image. 165. The system of embodiment 164, wherein the positioning component is configured to reduce or minimize head tilt by the subject. 166. The system of embodiment 163, wherein the kiosk further comprises a microphone and a speaker, and is configured to provide teleconferencing with a remote healthcare provider to discuss the determination and optionally a treatment recommendation. 167. The system of embodiment 163, wherein the kiosk comprises an interface for receiving payment information. 168. The system of embodiment 167, wherein the interface comprises a card reader, a scanner, an RFID system, a cash acceptor, a touchscreen for entering payment information, or a combination thereof. 169. A computing system comprising at least one processor, a memory, and non-transitory computer readable storage media encoded with a program including instructions executable by the at least one processor to create a web application comprising: a) a software module receiving a medical image uploaded by an electronic device over a network; b) a software module analyzing the ophthalmic image with a trained classifier to determine whether the ophthalmic image is indicative of a medical disease or disorder, the determination having a sensitivity greater than 90% and a specificity greater than 90%; and c) a software module sending the determination to the electronic device. 170. The system of embodiment 169, wherein the trained classifier is generated through a machine learning procedure. 171. The system of embodiment 170, wherein the machine learning procedure comprises a deep learning procedure. 172. The system of embodiment 170 or 171, wherein the machine learning procedure comprises training a convolutional neural network. 173. The system of any of embodiments 169-172, wherein the application further comprises a software module subjecting the ophthalmic image to an image occlusion procedure. 174. The system of embodiment 173, wherein the application further comprises a software module sending the ophthalmic image to the electronic device, wherein the areas of the ophthalmic image identified as significant to the determination by the image occlusion procedure are visually accentuated. 175. The system of any of embodiments 170-174, wherein the machine learning procedure further comprises a transfer learning procedure. 176. The system of embodiment 175, wherein the transfer learning procedure comprises pre-training an untrained classifier using non-medical images obtained from a large image dataset to obtain a pre-trained classifier. 177. The system of embodiment 176, wherein the transfer learning procedure further comprises training the pre-trained classifier using a set of medical images that is smaller than the large image dataset to obtain the trained classifier. 178. The system of any one of embodiments 169-177, wherein the application further comprises a software module making a medical treatment recommendation based on the determination. 179. The system of any one of embodiments 169-178, wherein the ophthalmic image conveys information about a presence or absence of an ophthalmic disease or disorder. 180. The system of any one of embodiments 169-179, wherein the ophthalmic image is a retinal image. 181. The system of any one of embodiments 169-180, wherein the ophthalmic image is an optical coherence tomography (OCT) image. 182. The system of embodiment 179, wherein the ophthalmic disease or disorder is selected from the group consisting of: age-related macular degeneration (AMD), diabetic macular edema (DME), and choroidal neovascularization (CNV). 183. The system of any of embodiments 169-182, wherein the system is a server integrated into a cloud network.

EXAMPLES

Example 1

A total of 207,130 OCT images were initially obtained of which 108,312 images (37,206 with CNV, 11,349 with DME, 8617 with drusen, and 51,140 normal) from 4,686 patients were used to train the AI system. The trained model (e.g. trained machine learning algorithm or classifier) was then tested with 1,000 images (250 from each category—CNV, DME, drusen, and normal) from 633 patients.

After 100 epochs (iterations through the entire dataset), the training was stopped due to the absence of further improvement in both accuracy (FIG. 4A) and cross-entropy loss (FIG. 4B).

In a multi-class comparison between CNV, DME, drusen, and normal, an accuracy of 96.6% (FIG. 4), with a sensitivity of 97.8%, a specificity of 97.4%, and a weighted error of 6.6% were achieved. ROC curves were generated to evaluate the model's ability to distinguish "urgent referrals" (defined as CNV or DME) from normal and drusen exams. The area under the ROC curve was 99.9% (FIG. 4).

Another "limited model" was trained for classifying between the same four categories, but only using 1,000 images randomly selected from each class during training to compare transfer learning performance using limited data compared to results using a large dataset. Using the same testing images, the model achieved an accuracy of 93.4%, with a sensitivity of 96.6%, a specificity of 94.0%, and a weighted error of 12.7%. The ROC curves distinguishing "urgent referrals" had an area under the curve of 98.8%.

Figure 7A:
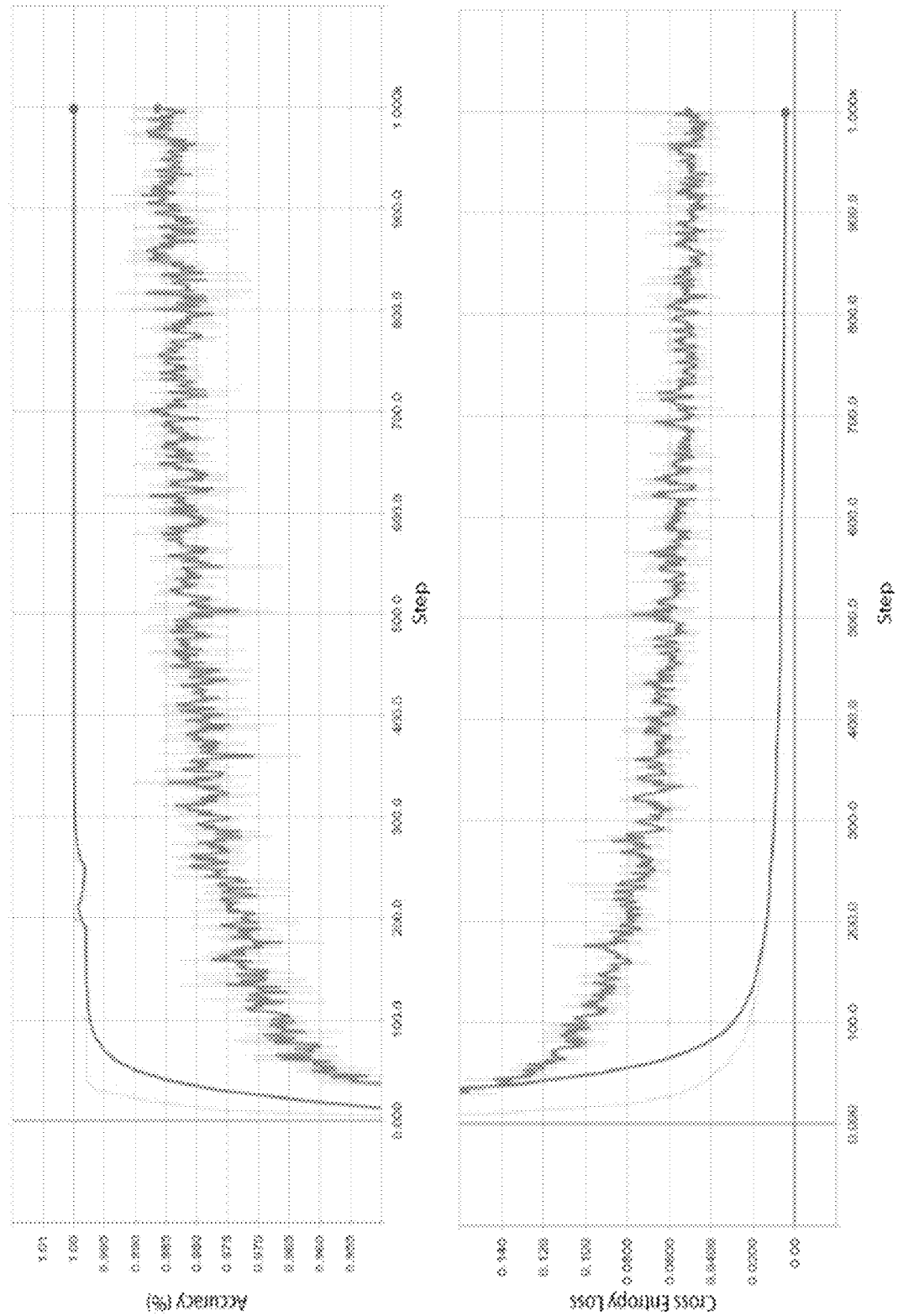
Figure 7B:
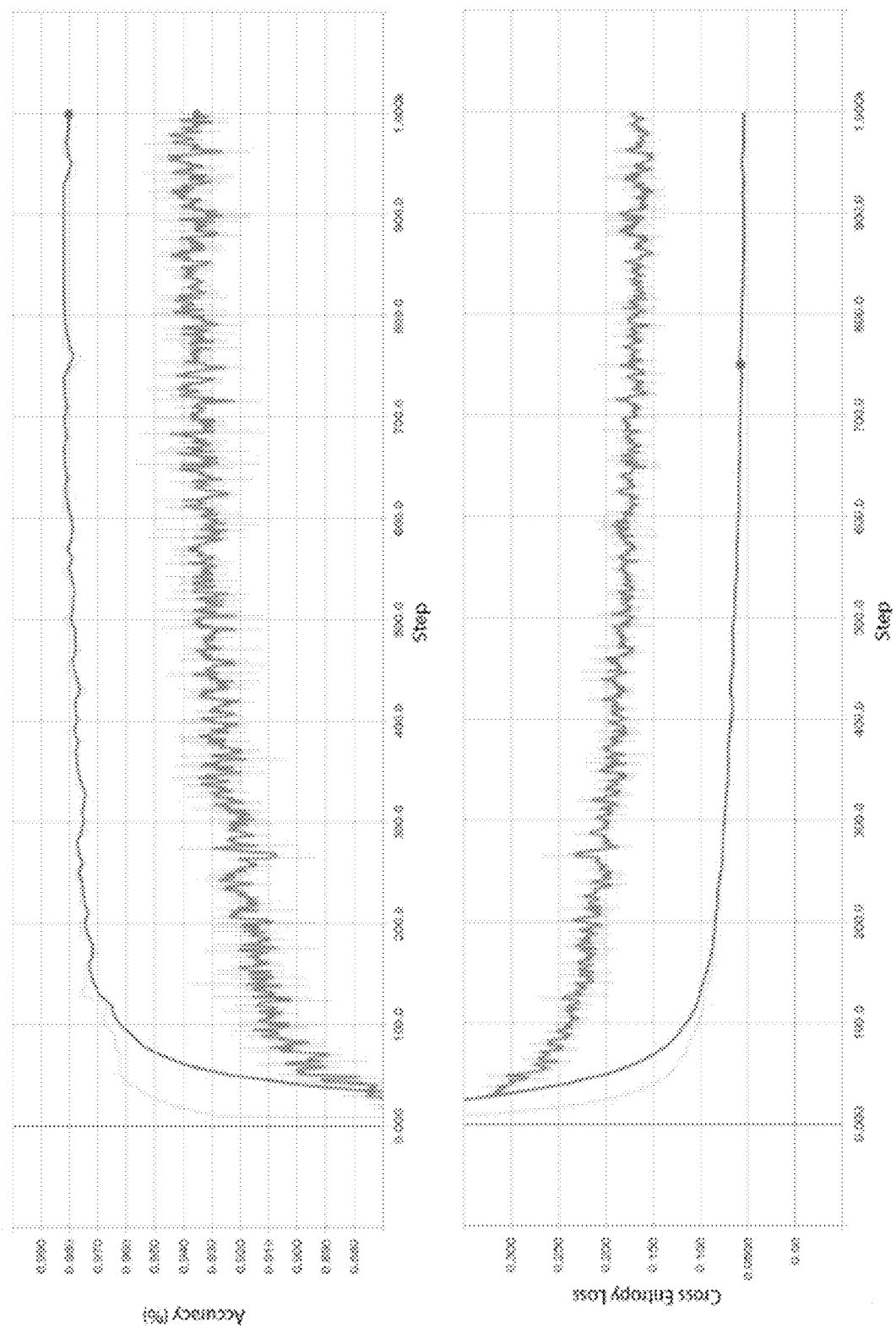

Binary classifiers were also implemented to compare CNV/DME/drusen from normal using the same datasets in order to determine a breakdown of the model's performance. As seen in FIGS. 7A and 7B, the classifier distinguishing CNV images from normal images achieved an accuracy of 100.0%, with a sensitivity of 100.0% and specificity of 100.0%. The area under the ROC curve was 100.0% (FIG. 8A). The classifier distinguishing DME images from normal images achieved an accuracy of 98.2%, with a sensitivity of 96.8% and specificity of 99.6%. The area under the ROC curve was 99.87% (FIG. 8B). The classifier distinguishing drusen images from normal images achieved an accuracy of 99.0%, with a sensitivity of 98.0% and specificity of 99.2%. The area under the ROC curve was 99.96% (FIG. 8C).

Occlusion testing was performed to identify the areas contributing most to the neural network's assignment of the predicted diagnosis. This testing successfully identified the region of interest that contributed the highest importance to the deep learning algorithm (FIG. 6). Furthermore, these regions were consistent with what human experts deemed to be clinically significant areas of pathology.

Training the chest X-ray images required grading to determine a ground-truth label for each image, followed by preprocessing involving cropping of images to only include the chest. The images were separated into a training set (460 viral and 460 bacterial) and a validation set (67 viral and 67 bacterial). The PyTorch framework with a GTX 970 GPU was used for training the final layer of a state-of-the-art ResNet-50 architecture pretrained on the ImageNet dataset. During training, the data was artificially augmented using a random cropping of 224×224 pixels and random horizontal flipping in order to strengthen the small dataset and allow the model to minimize overfitting. Using stochastic gradient descent (SGD) as the optimizer during training, an initial learning rate of 0.1 with an exponential decrease every 10 epochs was used. The training was executed over 50 epochs, or iterations through the entire dataset, and validation was performed after each epoch to measure current performance. The model weights with the best validation performance were saved as the best model with an accuracy of 66%. After removing the images previously marked incorrect and rerunning training, the model with the best accuracy reported 78.7% accuracy.

Example 2

An independent test set of 1000 images from 633 patients was used to compare the AI network's referral decisions (e.g. using the AI from Example 1) with the decisions made by human experts. Six experts with significant clinical experience in an academic ophthalmology center were instructed to make a referral decision on each test patient using only the patient's OCT images. Performance on the clinically most important decision of distinguishing patients needing "urgent referral" (those with CNV or DME) compared to normal patients is displayed as a ROC curve, and this performance was comparable between the AI system and the human experts (FIG. 4A).

Having established a standard expert performance evaluation system, the potential impact of patient referral decisions between the network and human experts was compared. The sensitivities and specificities of the experts were plotted on the ROC curve of the trained model, and the differences in diagnostic performance, measured by likelihood ratios, between the model and human experts were determined to be statistically similar within a 95% confidence interval (FIG. 9). The pure error rate does not accurately reflect the impact that a wrong referral decision might have on the outcome of an individual patient. To illustrate, a false positive result occurs when a patient is normal or just has drusen but is inaccurately referred, and this can cause undue distress or unnecessary investigation for the patient and place extra burdens on the healthcare system. However, a false negative result is far more serious, because in this instance a patient with CNV or DME is not appropriately referred, which could result in irreversible visual loss. To account for these issues, weighted error scoring was incorporated during model evaluation and expert testing (FIG. 10A), By assigning these penalty points to each decision made by the model and the experts, the average error of each could be computed.

The best CNN model yielded a score of 6.6% under this weighted error system. In order to establish a reference standard, this score was compared to the scores of 6 human experts quizzed on the validation dataset. The weighted error of the experts ranged from 0.5% to 10.5%, with a mean weighted average of 4.8%. As seen in FIG. 10B, the best model outperforms some human experts based on this weighted scale, and on the ROC curve.

Methods

Datasets

Optical coherence tomography (OCT) images were selected from retrospective cohorts of adult patients from Shiley Eye Institute of University of California San Diego, Calif. Retinal Research Foundation, and the Shanghai First People's Hospital between Jul. 1, 2013 and Mar. 1, 2017, who had OCT imaging (Spetralis OCT, Heiderberg Engineering, Germany) as part of their routine clinical care. The local electronic medical record databases were searched for diagnoses of CNV, DME, drusen and normal to initially assign images. OCT raw data was exported and reprocessed by exporting single B-scans and the 3 most central cuts of volume scans into standard image formats through a Matlab script provided by Heidelberg engineers. Institutional Review Board (IRB)/Ethics Committee approval was obtained. The work was conducted in a manner compliant with the United States Health Insurance Portability and Accountability Act (HIPAA) and was adherent to the tenets of the Declaration of Helsinki. There were no inclusion criteria based on age, gender, or race.

A total of 170,637 OCT scans were enrolled in this study. To create a test set representative of the real-world clinical application, 633 additional patients (mean age 63.1; 443 male, 551 female) during the retrospective study period were selected and only their referral OCT examination was selected for inclusion in the test set; the number included was based on a sample size requirement of 583 patients to detect sensitivity and specificity at 0.05 marginal error and 99% confidence.

Clinical Features

OCT examinations were interpreted to form a diagnosis, and referral decisions were made thereafter ("urgent referral" for diagnoses of CNV or DME, "routine referral" for drusen, and "observation only" for normal) in a retina clinic setting. The dataset represents the most common medical retina patients presenting and receiving treatment at all participating clinics.

Image Labelling

Before training, each image went through a tiered grading system consisting of multiple layers of trained graders of increasing expertise for verification and correction of image labels. Each image imported into the database started with a label matching the most recent diagnosis of the patient. The first tier of graders consisted of undergraduate and medical students who had taken and passed an OCT interpretation course review. OCT images containing severe artifacts or significant image resolution reductions were excluded from the study. Scans where no diagnostic label could be attached (as described below) were also excluded. The presence or absence of choroidal neovascularization, macular edema, drusen, and other pathologies visible on the OCT scan were recorded. The second tier of graders included two ophthalmologists who independently graded each image that had passed the first tier. Finally, a third tier of independent retinal specialists verified the true labels for each image. To account for human error in grading, a validation subset of 993 scans was graded separately by two ophthalmologist graders with disagreement in clinical labels arbitrated by a senior retinal specialist.

Transfer Learning Methods

A residual DNN called ResNet (He et al, 2016) and a multilayer feedforward DNN inception (Szegedy et al, 2015) were adapted for transfer learning. The pretrained Inception-v3 architecture is implemented in Tensorflow, and the three pretrained ResNet variants (ResNet-50, -101, -152) are implemented in PyTorch. While the ResNet variants have shown significantly less error in the ImageNet dataset, the Inception model yielded slightly higher accuracy in OCT classification.

With both models, retraining consisted of initializing the convolutional layers with the pretrained weights and retraining the final, softmax layer to recognize the classes from scratch. In this study, the convolutional layers were frozen and used as fixed feature extractors. The convolutional "bottlenecks" are the values of each training and testing images after it has passed through the frozen layers of the model and since the convolutional weights are not updated, these values are initially calculated and stored in order to reduce redundant processes and speed up training. Attempts at "fine-tuning" the convolutional layers by training the pretrained weights to the medical images using backpropagation tended to decrease performance by overfitting.

The Inception model was trained on an Ubuntu 16.04 computer with 2 Intel Xeon CPUs, using a NVIDIA GTX 1080 8 Gb GPU for training and testing, with 256 Gb available in RAM memory. Training of layers done by stochastic gradient descent in batches of 1,000 images per step using an Adam Optimizer with a learning rate of 0.001. Training on all categories was run for 10,000 steps, or 100 epochs, since training will have converged by then for all classes. Validation was performed after every step and the best performing model was kept for analysis.

The ResNet variants were trained using an Ubuntu 16.04 computer with an Intel i5-4690k CPU, using a NVIDIA GTX 970 4 Gb GPU for training and testing, with 4 Gb available in RAM memory. Training used stochastic gradient descent in batches of 8 images with an initial learning rate of 0.1 that is exponentially reduced by a factor of 0.1 every 7 epochs. Training on classes was run for 100 epochs. Validation was performed after every epoch and the best performing model was kept for analysis.

Expert Comparisons

In order to evaluate the model in the context of clinical experts, a validation set of 1000 images (633 patients) was used to compare the network referral decisions with the decisions made by human experts. Weighted error scoring was used to reflect the fact that a false negative result (failing to refer) is more detrimental than a false positive result (making a referral when it was not warranted). Using these weighted penalty points, error rates were computed for the model and for each of the human experts.

Occlusion Test

An occlusion test was performed on 491 images to identify the areas contributing the most to the neural network's assignment of the predicted diagnosis. A blank 20×20 pixel box was systematically moved across every possible position in the image and the probabilities of the disease were recorded. The highest drop in the probability represents the region of interest that contributed the highest importance to the deep learning algorithm (FIG. 6). This testing successfully identified the region of interest in 94.7% of images that contributed the highest importance to the deep-learning algorithm (FIG. 6). These regions identified by occlusion testing were also verified by human experts to be the most clinically significant areas of pathology.

Demonstrative Website and Tool

Our publicly available trained model at https://www.medfirstview.com allows interested parties to test the classification performance of the model. The Python tool implements a Tkinter user interface that allows a user to upload an OCT image, loads the trained model, and streams the image through the neural network to make a classification. The website uses the same method without the Tkinter user interface.

Quantification and Statistical Analysis

The 170,367 images collected was reduced to the total number of OCT images used for training (N=108,312) from 4,686 patients. Another subset of 633 patients not in the training set was collected based on a sample size requirement of 583 patients to detect sensitivity and specificity at 0.05 marginal error and 99% confidence. The test images (n=1000) were used to evaluate model and human expert performance. Receiver operating characteristics (ROC) curves plot the true positive rate versus the false positive rate. ROC curves were generated using classification probabilities of urgent referral versus otherwise and the true labels of each test image and the ROC function of the Python scikit-learn library. The area under the ROC curve (AU-ROC) is equal to the probability that the classifier will rank a randomly chosen "urgent referral" instance higher than a randomly chosen normal or drusen instance. Accuracy was measured by dividing the number of correctly labeled images by the total number of test images. Sensitivity (true positive rate) and specificity (true negative rate) were determined by dividing the total number of urgent referrals correctly labeled as such and the total number of non-urgent labels correctly labeled, respectively, by the total number of test images.

Data and Software Availability

All deep learning methods were implemented using either TensorFlow (https://www.tensorflow.org) or PyTorch (https://www.pytorch.org). ImageNet public database of images can be found at https://www.image-net.org. OCT data was translated into high resolution TIFF images using a proprietary Heidelberg script to extract B-scans and the 3 most foveal cuts of volume scans. All other scripts and analysis for this project were created by the researchers of this project written in Python and Bash.

Application to Non-Ophthalmic Diseases

Although described with respect to ophthalmic diseases, it is also contemplated herein that the method, system, and/or computer-readable medium in the present disclosure can be used in diagnosis of non-ophthalmic diseases or conditions.

Example 3

Summary

Despite the overall effectiveness of cataract surgery in improving vision, a significant number of patients still have decreased vision after cataract extraction. Understanding the underlying etiologies of persistent post-operative vision impairment is of great importance. In China, myopia is the number one cause of visual impairment, with nearly half of population being affected. Despite its prevalence, its impact on the visual outcomes after cataract surgery remains unclear. In this study, a prospective trial was conducted on the effects of high myopia on visual outcomes after cataract surgery in 1,005 patients with high myopia patients (axial length≥26 mm). Multi-variable analysis was conducted to identify factors influencing visual outcomes. Macular sensitivity images were then used to train a deep learning model for predicting post-operative visual acuity. This model demonstrated an accuracy of over 90% in the validation set, suggesting the high utility of artificial intelligence (AI) in myopic maculopathy prognosis. In addition, an increased level of pro-growth factors was detected in highly myopic eyes, such as GDF-15, HGF, PDGF-AA, and VEGF, which may be a possible mechanism of the elongation of the posterior segment of the eye in pathologic myopia.

Cataract surgery is the most commonly performed ophthalmic procedure worldwide, with more than 20 million surgeries done each year. In 1999, the Chinese government and the Lions Club International Foundation launched a nationwide Blindness Prevention and Treatment Project called SightFirst China Action, to support cataract surgeries and eye care infrastructures in China. Out of 22,032 patients in the study cohort, 7,116 had high myopia at the time of surgery between October 2015 and July 2017.

Post-operative visual acuity was noted to be worse in patients with high myopia, a leading cause of visual impairment and blindness in East Asia. Complications such as high myopia-related retinal and optic disc damages can be irreversible and cause significant ocular morbidity. Myopic maculopathies such as choroidal neovascularization, chorioretinal atrophy, and foveoschisis are associated with excessive eye elongation and degeneration of the chorioretinal tissue. Therefore, myopic maculopathy incurs a higher risk of visual impairment among eyes with high myopia. Furthermore, highly myopic eyes are at greater risk of intraoperative vitreous loss, postoperative retinal tear or detachment, and less precise intraocular lens calculations due to posterior staphyloma and myopic maculopathy, all of which have the potential to lead to decreased visual acuity after cataract surgery.

Several existing classification systems have been proposed for classifying myopic maculopathy. In 2015, Matsui et al. integrated the concepts from these various classification schemes and proposed a five-category International Photographic Classification and Grading System For Myopic Maculopathy. However, this system remains a morphological classification and does not include any measurement reflecting macular function.

This study enrolled 22,023 patients, including 7,116 patients with high myopia. Fixation stability and macular sensitivity, two complementary metrics, were examined to better quantify macular function. In non-myopic eyes, good fixation stability can be attained due to uncompromised macular function. In contrast, in highly myopic eyes, an increasing severity of maculopathy leads to impaired fixation stability. In terms of evaluating macular function, macular mean sensitivity (MS) measured by microperimetry is considered a more precise method than visual acuity. Macular Integrity Assessment (MAIA) microperimetry (Centervue, Padova, Italy) enables precise real-time monitoring of fixational eye movements during perimetric examination and provides an accurate correlation between retinal sensitivity and pathological findings.

An artificial intelligence (AI) system was trained to classify pathological myopia using the macular function test results. AI has demonstrated immense potential to facilitate clinical decision making and disease management. Using deep learning algorithms, AI has the potential to review large datasets to gain experience and examine training examples from different aspects. After training, the system could, within seconds, revise enormous databases, calculate, and make decisions accordingly. The promising potential of AI enables a future where more accurate disease diagnosis and treatment within a shorter time frame could be possible. In this study, an accurate pathologic myopia prognosis model was built by developing a deep learning algorithm using macular function images and related clinical covariates.

Aside from the analysis of retinal images and macular function classification, the molecular mechanisms underlying myopic maculopathy were investigated using immunoassays. Although axial elongation is one of the most important causes of myopic maculopathy, particularly the focal elongation seen in posterior staphyloma, the underlying mechanism of global elongation of the myopic eye is largely unknown. Therefore, this study investigated growth factors for association with high myopia, representing possible future targets for the therapeutic interventions.

In summary, a comprehensive AI evaluation system was established to predict the effects of myopic maculopathy on visual outcomes after cataract surgery (FIG. 13) while also elucidating potential mechanisms for intervention.

Materials and Methods

Study Participants

The Shanghai High Myopia Study is an ongoing hospital-based prospective cohort study of highly myopic patients scheduled for cataract surgeries since October 2015 at the Eye, Ear, Nose, and Throat (EENT) Hospital of Fudan University. A prospective study was conducted on the impact of high myopia on visual outcomes after cataract surgery from October 2015 to July 2017, enrolling a total of 22,023 patients. All patients underwent detailed preoperative examinations and follow-ups for 1-2 months after the surgeries. There were 7,116 patients with high myopia, defined as axial length>26.00 mm. Among which 1,005 patients were enrolled due to not having some other intraocular pathology that caused poor vision (e.g. anterior segment diseases, trauma, etc.). Macular function studies were performed for all of the patients, and one eye of every patient was randomly selected for investigation. The Institutional Review Board of the EENT Hospital of Fudan University approved the study protocol. All participants were informed about the study objectives and signed informed consent. The study was registered at www.clinicaltrials.gov (Accession number: NCT03062085) and all procedures adhered to the tenets of the Declaration of Helsinki.

Preoperative and Postoperative Examinations

The preoperative examinations included assessments of visual acuity, refraction, fundoscopy, tonometry, corneal topography, B-scans, optical coherence tomography (OCT) macular scans (Zeiss Cirrus HD-OCT 5000, Carl Zeiss AG, Jena, Germany), and axial length measurement (IOLMaster 500; Version 7.7 Carl Zeiss AG, Jena, Germany). An ophthalmic follow-up examination was conducted 1-2 months after surgery, which included assessments of visual acuity, refraction, tonometry, retinal photography, fundoscopy, and OCT macular scans.

Ultra-widefield retinal images, using standard settings, were obtained postoperatively using non-mydriatic ultra-widefield scanning laser ophthalmoscopy (Optomap 200Tx; Optos plc. Dunfermline, Scotland, UK). Myopic maculopathy from fundus photographs were classified into five categories based on the International Photographic Classification And Grading System. To be specific: category 0, no myopic retinal degenerative lesions; category 1, tessellated fundus; category 2, diffuse chorioretinal atrophy; category 3, patchy chorioretinal atrophy; category 4, macular atrophy. Furthermore, among patients classified as category 3, one group of patients who had patchy atrophy more than 9 disc diameters and an island-like remaining foveal structure were specifically studied as a separate subset.

Fixation and Macular Sensitivity Evaluation

To avoid interference from a cloudy lens, ocular fixation was investigated during the postoperative follow-up with the MAIA microperimeter system. The eye tracker detects fixation losses as any misalignment between the central fixation stimulus and the directions of gaze. During examination, patients were instructed to stare at the fixation stimulus (a red circle with a diameter of 1°), while the eye tracker recorded the points of fixation. The microperimeter measured two fixation variables: the bivariate contour ellipse area (BCEA), which represents the area in degrees-squared ($deg^2$) of the ellipse containing the majority of the fixation positions registered during the microperimetry testing; and the fixation ellipse angle, which is the direction of the long-axis of the BCEA.

The MS measurements were obtained using 'Expert Exam', which utilizes a 4-2 staircase threshold strategy in a static exam procedure. The microperimetry used a standard predetermined grid, with 37 projection positions distributed in 3 concentric circles (diameters: 2°, 6°, and 10°) of 12 points and a central point. The sensitivity and average threshold in the different positions was evaluated by the instrument software.

Image Data Pre-Processing

A total of 1,005 patient microperimeter results were exported and collected. The x-y coordinate resolution of each image was reduced from floating point to integer level, which facilitated image comparison in the same coordinate space and resulted in 177 points covering all the images. This results in a vector threshold matrix encompassing patients by image.

Principal Component Analysis

The data was initially evaluated using an unsupervised approach. In order to achieve this goal, the first principal component (PC0) was fitted on all the macular sensitivity threshold images using the fit transform function from the Python machine learning library sklearn. The first PC was used as a classification score to separate the patients into two groups: 1) patients with worse visual outcome, defined as those with best corrected visual acuity (BCVA) of log MAR>0.7(20/100), and 2 patients with better visual acuity (BCVA(log MAR)≤0.7). The classification score ROC-AUC (Receiver Operating Characteristic-Area Under the Curve) was computed using the metrics.roc_auc_score function of the sklearn package.

Neural Network for Patient Prognosis

Our AI framework was built based on Python (version 3.6.4) and Tensorflow (version 1.6.0) libraries. To avoid overfitting, only 5 neurons were used in each layer. In the initial analysis, only patients whose diagnoses were highly certain were included. Patients with post-operative BCVA (log MAR)≤0.5 (20/63, patients with high likelihood of having good vision) were defined as negative instances, and patients with post-operative BCVA(log MAR)>0.7 (20/100, patients with high likelihood of having poor vision) were defined as positive instances. Among those instances, the data was split into training and testing cohorts in a 1:1 ratio. Age (year) and axial length (mm) information were also incorporated into the model. The learning rate used in training the neural network was 0.001, and it was trained for a total of 10,000 steps. The accuracy of model in each training step for both the training and testing cohorts was also recorded.

Aqueous Humor Acquisition

Aqueous humor was obtained from 36 eyes with high myopia (axial length≥26 mm) and 32 control eyes (axial length<24.5 mm) at the start of cataract surgeries soon after paracentesis was made as previously described.

Quantibody® Human Growth Factor Arrays

For the purpose of preliminary screening, Quantibody® Human Growth Factor Array (QAH-GF-1, RayBiotech, Norcross, Ga., USA), a slide-based multiplexed antibody array platform, was used to determine the concentration of 40 growth factors in aqueous humor simultaneously. In accordance with the protocol, the glass surface bound with cytokine specific antibodies was firstly equilibrated to room temperature and air-dried. Then 100 µl aqueous humor was applied to each well without dilution and incubated overnight at 4° C. Then samples from each well were decanted, leaving cytokines present in the samples captured by corresponding antibodies in the well. Biotinylated antibody cocktail was added afterwards for the detection of bound cytokines and Cy3 equivalent dye-streptavidin for visualization of signals, which were scanned by GenePix 4000B (Axon Instruments, Foster City, Calif., USA). Each antibody was arrayed in quadruplicate. GenePix Pro 6.0 (Axon Instruments, Foster City, Calif., USA) was utilized for data extraction and microarray analysis.

Bio-Plex Pro™ Multiplex Bead-Based Immunoassay

Concentrations of growth factors showing statistically significant intergroup differences in the screening stage were further verified by the multiplex bead-based immunoassay using human premixed multi-analyte kit (Bio-Rad, Hercules, Calif., USA) and Bio-Plex® MAGPIX system (Bio-Rad, Hercules, Calif., USA) according to the instruction manual. Growth factors below the quantification range were ruled out. Selected growth factors included growth differentiation factor (GDF)-15, hepatocyte growth factor (HGF), and platelet-derived growth factor (PDGF)-AA. Briefly, 50 µl magnetic beads with capture antibody were first added to the wells. After incubation at room temperature for an hour, a series of washes were processed to remove unbound protein. Multiplexed cocktails of biotinylated detection antibodies were then applied, creating sandwich complexes for the formation of final detection complexes with addition of streptavidin-phycoerythrin conjugate, the fluorescent indicator. Fluorescent signals were acquired by Bio-Plex® MAGPIX™ reader (Bio-Rad, Hercules, Calif., USA) and transferred to corresponding concentrations (pg/ml) by Bio-Plex Manager™ software (Bio-Rad, Hercules, Calif., USA).

Statistical Analysis

Interobserver agreement of fundus image classification by two observers was assessed using the kappa statistic. The weighted kappa statistic (κ) was calculated and considered satisfactory if κ≥0.6. Agreement on the optic disc orientation, optic disc tilt ratio, and degree of optic disc rotation between the two observers was assessed using the Bland-Altman method, which plotted each observer's mean against the difference. Continuous variables were presented as the mean±standard deviation. The $\chi 2$ test was used to compare categorical data. The Mann-Whitney U-test was used to compare the mean value of two groups without a normal distribution. One-way analysis of variance (ANOVA) was used to compare continuous variables between multiple groups. Relationships between continuous variables were assessed using Pearson's correlation analysis. Relationships between continuous and categorical variables were assessed using Spearman's correlation analysis. Multiple linear regression analysis, adjusted for age, sex, and operated eye, was performed to determine the effects of the following: axial length, BCEA, fixation angle, and myopic maculopathy grade, on MS. In all analyses, p-values<0.05 were considered statistically significant. Statistical analyses were performed using Python scipy package (version 1.0.0).
Results
Patients Information and Clinical Characteristics In a review of 22,032 eyes (including 7,116 highly myopic eyes) that underwent cataract surgeries in the center between October 2015 and July 2017, long axial length (≥26 mm) emerged as a risk factor for poor visual prognosis post-operatively (FIG. 13A). 1,005 highly myopic patients Macular function was quantified using foveal fixation stability and macular sensitivity. Axial length, macular mean sensitivity and fixation characteristics were significantly different among the four categories of myopic maculopathy (Table 2). Greater severity of maculopathy was associated with increasing mean axial length. In addition, with increasing grade of maculopathy, the macular sensitivity decreased and the BCEA increased, both indicating more severely impaired macular visual function (P<0.001).

TABLE 2

Axial length, macular function and fixation stability in the four categories of myopic maculopathy

|  | Category 1 | Category 2 | Category 3 | Category 4 | Anova-Test-statistics | P Value |
|---|---|---|---|---|---|---|
| AL | 28.67 ± 1.89 | 31.38 ± 2.00 | 31.19 ± 2.06 | 30.01 ± 2.40 | 45.46 | <0.001 |
| MS | 24.56 ± 3.17 | 20.78 ± 3.00 | 18.22 ± 4.94 | 8.61 ± 7.12 | 114.8 | <0.001 |
| BCEA (deg 2)† | 15.88 ± 19.12 | 22.54 ± 23.28 | 29.77 ± 32.57 | 55.85 ± 38.12 | 307.64 | <0.001 |

Data are presented as mean ± standard deviation.
AL = axial length;
MS = mean macular sensitivity;
BCEA = bivariate contour ellipse area;
PO-BCVA = post-operative best corrected visual acuity
†Statistically significant differences were found among the four categories in terms of AL, MS, BCEA.
(ANOVA: P < 0.0001)

met eligibility criteria (axial length≥26 mm, excluded a history of anterior segment ocular disease, trauma, or systemic conditions that affected visual performance) were enrolled. Table 1 presents the baseline patients characteristics for this study. The average age was 61.33±9.19 years, and the database included 544(54.1%) women and 461 (45.9%) men. The mean axial length was 29.47±2.27 mm (range, 25.76-36.42 mm). The mean post-op BCVA (log MAR) was 0.24±0.37(20/35). The average results of the macular sensitivity test was 22.51±5.14 db for macular sensitivity and 20.38±24.64 deg$^2$ for BCEA.

TABLE 1

Demographic characteristics of participants

| Parameter | Value (n = 1,005) |
|---|---|
| Age (Years) | 61.33 ± 9.19 |
| Sex (Male/Female) | 461/544 |
| Eye (Right/Left) | 506/499 |
| BCVA (logMAR) | 0.24 ± 0.37 |
| AL (mm) | 29.46 ± 2.27 |
| MS (dB) | 22.51 ± 5.14 |
| BCEA (deg$^2$) | 20.38 ± 24.64 |

Data are presented as mean ± standard deviation.
BCVA = best corrected visual acuity;
AL = Axial length;
BCEA = Bivariate contour ellipse area.

Relationship Among Post-Operative Visual Outcomes, Axial Length and Maculopathy Grading Post-operative visual outcomes were significantly poorer in eyes with relatively longer axial lengths in all patients (FIG. 14B, ANOVA test-statistics=9.54, P<0.0001). To analyze the factors that could affect visual outcomes, patient macular changes with fundus images were classified using a current international grading system on myopic maculopathy (FIG. 15A-E). There were 678 patients (67.46%) in grade 1,136 patients (13.53%) in grade 2, 154 patients (15.32%) in grade 3, and 37 patients (3.68%) in grade 4.

A representative case of the island-like macular atrophy pattern was shown in FIG. 16A. The dark area in the macular grid indicated the dysfunctional area of atrophy, and the fixation ellipse was located on the remaining macular tissue (FIG. 16B). Among the 14 patients with island-like macular atrophy pattern out of the 154 patients in category 3, postoperative visual outcomes were significantly poorer in this subgroup compared to the rest of the patients in category 3 (BCVA(log MAR) of 0.54 vs. 0.36, p<0.05, t-test, FIG. 16C).

Figure 16E:
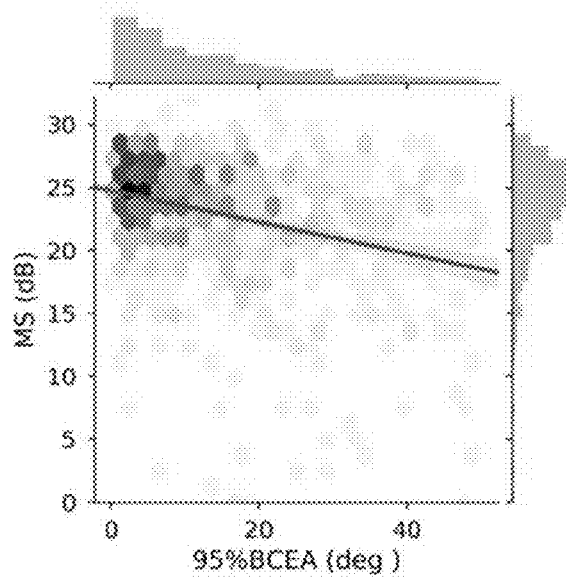
Figure 16F:
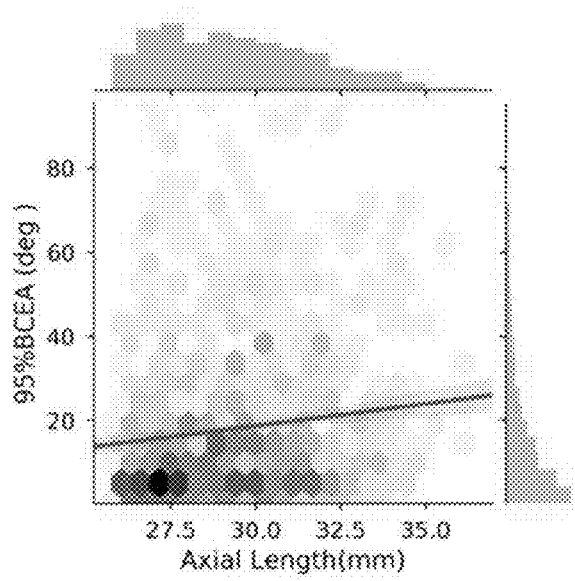

As expected, macular sensitivity was negatively correlated with axial length (Pearson's correlation: r=−0.34, P<0.001, FIG. 16D) and BCEA (Pearson's correlation: r=−0.32, P<0.001, FIG. 16E). BCEA was positively correlated with axial length (Pearson's correlation: r=0.13, P<0.001, FIG. 16F).

Using Deep Learning to Predict Visual Prognosis for High Myopia Patients

A two-layer hierarchical neural network was built and validated to predict patient visual acuity using post-surgery macular sensitivity threshold images (see Methods, FIG. 17). First, principal component analysis (PCA), an unsupervised approach, was applied to identify lower dimensional features in macular sensitivity images that correlate with visual acuity. It was hypothesized that variation in the images was driven by variation in visual acuities. Indeed, the patients' first principal component (PC0) score correlated with BCVA (FIG. 18A, R=0.48, p<1e-16, f-test) and could already make reasonably accurate prognostic predictions (FIG. 18B, ROC-AUC=0.851).

This suggests that changes in macular function images correlate with changes in patients' post-operative visual acuities.

Neural Network for Patient Prognosis

To build a prognostic model to predict patients' post-operative visual outcomes, a hierarchical neural network, e.g. deep learning, was applied on the macular sensitivity images, along with age and axial length, which also have information towards predicting post-operative BCVA (FIG. 14B, Table 3). The data was split into training and testing (see Methods) cohorts. The model was trained for 10,000 steps, with FIG. 18C showing the neural network converging after 5000 steps, as the accuracy in both training and testing cohorts stabilized with further training. The final model yielded an accuracy of 0.931 and ROC-AUC of 0.918 in the validation cohort (FIG. 18D), suggesting that the neural network can predict visual acuity in patients using macular sensitivity test results with high accuracy.

TABLE 3

Macular function and fixation stability in different age, gender and AL groups

| | pts no. (n = 1,005) | MS | P Value | BCEA | P Value |
|---|---|---|---|---|---|
| Age (yrs) | | | | | |
| ≤61 | 520 | 21.93 ± 5.34 | <0.001 | 23.19 ± 26.08 | <0.001 |
| >61 | 485 | 23.08 ± 4.91 | | 17.37 ± 22.64 | |
| AL (mm) | | | | | |
| <28.00 | 325 | 24.54 ± 3.76 | <0.001 | 17.58 ± 24.76 | <0.05 |
| 28.00~30.00 | 292 | 22.72 ± 5.59 | | 19.93 ± 22.21 | |
| >30.00 | 388 | 20.59 ± 5.18 | | 23.07 ± 26.02 | |
| Gender | | | | | |
| Male | 461 | 22.74 ± 5.22 | 0.12 | 19.91 ± 21.95 | 0.59 |
| Female | 544 | 22.27 ± 5.12 | | 20.78 ± 26.73 | |

AL = axial length;
MS = mean sensitivity;
BCEA = bivariate contour ellipse area
*Statistically significant differences were found among the three axial length groups in terms of MS. (ANOVA followed by Tukey test: 1 vs 2, P = 0.005; both 1 vs 3 and 2 vs 3: P < 0.001)
† Statistically significant differences were found among the three axial length groups in terms of BCEA. (ANOVA followed by Tukey test: 1 vs 2, P = 0.002; 1 vs 3, P < 0.001; 2 vs 3, P = 0.355)
No difference were found among different genders.

Molecular Mechanisms of Axial Length Elongation in High Myopia

It was postulated that certain growth factors may be involved in globe elongation, therefore increasing axial length. Therefore, the growth factors in aqueous fluid were surveyed. Among 40 growth factors evaluated, Growth Differentiation Factor-15 (GDF-15), Hepatocyte Growth Factor (HGF) and Platelet-derived Growth Factors AA (PDGF-AA) were found to be significantly elevated in the aqueous humor of highly myopic eyes with cataracts (HMC) compared with control eyes with age-related cataracts (ARC) (P=0.03; see Table 4). GDF-15 is related to inflammatory processes, while HGF and PDGF-AA are involved in cell growth and proliferation. The levels of GDF-15, HGF, and PDGF-AA were also significantly correlated with axial length (Spearman coefficient=0.503, 0.567, 0.458, all P<0.001; see FIG. 19). The standard curves for detected cytokines in this assay are provided online in FIG. 20.

TABLE 4

Growth factor concentrations in aqueous humor of high myopic eyes and controls in the validation phase

| Cytokines | Control eyes | High myopic eyes |
|---|---|---|
| GDF-15 | 65.34 ± 35.9 | 107.92 ± 71.7* |
| HGF | 101.84 ± 33.16 | 162.84 ± 68.33*** |

TABLE 4-continued

Growth factor concentrations in aqueous humor of high myopic eyes and controls in the validation phase

| Cytokines | Control eyes | High myopic eyes |
|---|---|---|
| PDGF-AA | 10.66 ± 5.67 | 13.51 ± 4.71** |
| VEGF | 34.94 ± 13.61 | 9.92 ± 8.33*** |

Values (in pg/ml) are presented as the mean ± standard deviation.
*P < 0.05,
**P < 0.01,
***P < 0.001, Mann-Whitney U test.
GDF-15: growth differentiation factor 15;
HGF: hepatocyte growth factor;
PDGF-AA: platelet-derived growth factor-AA;
VEGF: vascular endothelial growth factor.

Discussion

Myopic maculopathy can result in persistently decreased visual acuity after cataract surgery among eyes with high myopia. Elucidating which myopic patients may be at risk of poor visual outcomes after cataract surgery due to maculopathy can assist with appropriate preoperative counseling and expectations. In this study, an artificial intelligence framework was devised to accurately predict visual prognosis following cataract surgery for highly myopic patients.

First, clinical covariates were compared with visual acuity. A standardized myopic maculopathy classification system enabled reliable comparison of the prevalence and pattern of lesions between studies. the study indicated that with increased severity of grading of maculopathy, mean macular sensitivity decreased and the BCEA increased. Since both macular sensitivity and fixation stability in the form of BCEA have been recognized as sensitive indicators of macular function, the present data suggest that Matsui et al's photographic classification system, though not very precise, could differentiate the gradual impairment of macular function. However, with the system, morphologic changes no longer need to be characterized individually, such as lacquer cracks, Fuchs' spots, or chorioretinal atrophy, etc.

Image resolution was further investigated to improve the prognosis model. the results suggested that this subset had a significantly poorer visual outcome even among category 3 patients. The island-like macular atrophy in the small subgroup indicates a clinical need for close monitoring in order to preserve visual function, because the only remaining structure available for these patients to maintain their residual visual function is the small area of intact retina surrounded by atrophic areas visible on fundus photographs. Therefore, this structure should be carefully analyzed by cataract surgeons when considering the likely prognosis of cataract surgery, before making the decision to operate. Myopic macular changes are a result of mechanical stretching of the retina from axial elongation and in category 1 (tessellated fundus), the overlying retina becomes thinner and the deeper choroidal vessels are more obvious.

Moreover, state of the art machine learning methods, specifically deep learning, were applied to analyze the images and assess the visual acuity of highly myopic eyes after cataract surgery. The advantage of this comprehensive system is that more metrics are considered than macular morphology grade alone. The AI system combines the functional and morphological indices and enables multi-dimensional evaluation of myopic maculopathy. By utilizing macular sensitivity images, axial length and age, the model could predict a visual outcome of either good (BCVA(log MAR)<0.5) or poor (BCVA(log MAR)>0.5). In the future, with the addition of more patients and image types (for example: fundus image, Optical Coherence Tomography, Optical Coherence Tomography Angiograph, Fluorescein Angiography), the number of layers in the deep learning framework could be increased and can potentially further improve accuracy and resolution of the prognosis model.

Regarding the pathogenesis of myopic maculopathy, the underlying mechanism appears to be axial elongation of the whole eye. Thus, a pro-growth microenvironment within such eyes would be anticipated. A previous study proposed that there might be a special microenvironment within highly myopic eyes, with abnormally heightened monocyte chemotactic protein 1 and reduced interleukin-1 receptor antagonist, which was very likely to initiate an aggregation of inflammatory cells that later might bring excessive secretion of growth factors. In the current study, significantly higher levels of growth factors GDF-15, HGF and PDGF-AA were verified in aqueous humor of highly myopic eyes compared to controls. The levels of these growth factors tended to increase with increasing axial length of the eye. With the possibility of detecting more growth factors in both aqueous humor and vitreous in the future study, it may be possible to identify more small molecules or proteins that are related to the elongation of highly myopic eyes, which may further elucidate the detailed molecular mechanisms leading to the plus lesions seen in pathological myopia.

In conclusion, the study employed a new approach to evaluate cataract outcome. In particular, recognizing the island-like macular atrophy pattern within category 3 is important for visual function prognosis and expectation in this group of patients. A deep learning algorithm was then established to predict the visual outcomes after cataract surgeries on highly myopic patients. This machine learning framework comprised a comprehensive functional evaluation system of myopic maculopathy based on maculopathy grade, axial length, and fixation stability for highly myopic eyes. This system can accurately predict visual prognosis after cataract surgery, which would lead to improved ability to counsel patients and set expectations prior to surgery, leading to more informed clinical decision-making and potentially higher patient satisfaction. Finally, investigation of the pro-growth microenvironment within highly myopic eyes increases the understanding of the development of posterior staphylomas and the relationship with worsening myopic maculopathy.

Example 4—Software Integrated into Hardware

Diagnostic software implementing deep learning convolutional neural networks for analyzing retinal scans to screen for diabetic retinopathy are installed onto systems integrating imaging equipment and computing devices at a medical clinic. The computing devices are operatively coupled to the imaging equipment including stereoscopic color fundus photography. During a patient visit, the imaging equipment is used to capture an ophthalmic image of both retinas. The image is stored locally on the computing device operatively coupled to the imaging equipment. The software application installed on the computing device then analyzes the image using a trained convolutional neural network to classify the image as being positive or negative for diabetic retinopathy. The application uploads the image to a remote server over the network for remote classification or prediction and downloads the result. When communication with the remote server is unavailable, the software application is configured to perform the analysis using the locally stored convolutional neural network.

Example 5—Portable Diagnostic System

Diagnostic software implementing deep learning convolutional neural networks for analyzing retinal scans to screen for diabetic retinopathy are installed onto a user's smartphone as a mobile application. The mobile application enables the smartphone to upload retinal scans for remote diagnosis of diabetic retinopathy. The mobile application also allows the smartphone to integrate imaging equipment to capture the retinal image using the smartphone's own camera. An apparatus comprising an ophthalmoscope is detachably coupled to the smartphone such that the ophthalmoscope is positioned over the smartphone camera enabling the camera to capture the desired retinal scan. The retinal scan image is stored locally on the smartphone. The mobile application installed on the phone then analyzes the image using a trained convolutional neural network to classify the image as being positive or negative for diabetic retinopathy. The analysis includes uploading the image to a remote server over the network for remote classification or prediction and downloading the result. When communication with the remote server is unavailable, the mobile application is configured to perform the analysis using the locally stored convolutional neural network. Accordingly, this portable diagnostic system leverages the smartphone's electronics and camera in combination with the apparatus and ophthalmoscope to efficiently capture retinal scans and obtain diagnostic predictions.

Example 6—Diagnostic Hardware

A diagnostic device comprising a specialized camera and a digital processing device is utilized to capture an ophthalmic image of a retina and generate a diagnostic prediction of diabetic retinopathy. The device includes a specialized camera designed to capture retinal scans, which are stored on a memory of the digital processing device and subsequently analyzed by the device. The software application installed on the digital processing device analyzes the image using a trained convolutional neural network to classify the image as being positive or negative for diabetic retinopathy. The analysis includes uploading the image to a remote server over the network for remote classification or prediction and downloading the result. When communication with the remote server is unavailable, the software application is configured to perform the analysis using the locally stored convolutional neural network.

We claim:
1. A computer-implemented method for detecting an ophthalmic disease, disorder, or condition, the method comprising:
    generating a machine learning classifier that classifies medical data, including image data, into one of a plurality of classifications, wherein the machine learning classifier is generated by
    training a convolutional neural network using non-domain images that are not labeled with any of the plurality of classifications, and
    retraining upper layers of the convolutional neural network using domain images that are ophthalmic images labeled with one or more of the plurality of classifica- tions, while retaining lower layers of the convolutional neural network that were trained using the non-domain images;

obtaining an ophthalmic image of an individual;

evaluating the ophthalmic image using the machine learning classifier to generate a determination of the ophthalmic disease, disorder, or condition, the determination having a sensitivity of at least 90% and a specificity of at least 90% when tested against an independent data set of at least 200 samples; and providing the determination to the individual or a third party.

2. The method of claim 1, wherein the ophthalmic image of the individual comprises a retinal image.

3. The method of claim 2, wherein the retinal image is an optical coherence tomography (OCT) image.

4. The method of claim 2, wherein obtaining the retinal image comprises capturing the retinal image of the individual with an electronic device comprising a camera and a portable device comprising an imaging component, wherein the portable device and the electronic device are positioned to align the imaging component with the camera.

5. The method of claim 1, wherein evaluating the ophthalmic image comprises uploading the ophthalmic image to a cloud network for remote analysis of the ophthalmic image using the machine learning classifier.

6. The method of claim 1, wherein the ophthalmic disease, disorder, or condition is a retinal disease or condition.

7. The method of claim 6, wherein the retinal disease or condition is age-related macular degeneration (AMD), diabetic macular edema (DME), choroidal neovascularization (CNV), or diabetic retinopathy.

8. The method of claim 1, further comprising providing a recommendation for treatment or further testing to the individual or the third party.

9. A computer-implemented system comprising:

a server comprising at least one processor configured to generate a machine learning classifier that classifies medical data, including image data, into one of a plurality of classifications, wherein the machine learning classifier is generated by
training a convolutional neural network using non-domain images that are not labeled with any of the plurality of classifications, and
retraining upper layers of the convolutional neural network using domain images that are ophthalmic images labeled with one or more of the plurality of classifications, while retaining lower layers of the convolutional neural network that were trained using the non-domain images;

an electronic device comprising at least one processor, a memory, a camera, and an operating system;

a portable device comprising an imaging component, said portable device configured to receive and position the electronic device to align the camera with the imaging component; and a computer program stored in the memory of the electronic device, the computer program including instructions configured to, when executed by the at least one processor of the electronic device,
control the camera to capture an ophthalmic image of an individual,
evaluate the ophthalmic image using the machine learning classifier to generate a determination of an ophthalmic disease, disorder, or condition, the determination having a sensitivity of at least 90% and a specificity of at least 90% when tested against an independent data set of at least 200 samples, and
provide the determination to the individual or a third party.

10. The system of claim 9, wherein the ophthalmic image of the individual comprises a retinal image.

11. The system of claim 10, wherein the retinal image is an optical coherence tomography (OCT) image.

12. The system of claim 10, wherein the imaging component is an ophthalmoscope enabling the camera to capture the retinal image from an eye of the individual.

13. The system of claim 9, wherein evaluating the ophthalmic image comprises uploading the ophthalmic image to the server for remote analysis of the ophthalmic image using the machine learning classifier.

14. The system of claim 9, wherein the ophthalmic disease, disorder, or condition is a retinal disease or condition.

15. The system of claim 14, wherein the retinal disease or condition is age-related macular degeneration (AMD), diabetic macular edema (DME), choroidal neovascularization (CNV), or diabetic retinopathy.

16. The system of claim 9, wherein the computer program is further configured to provide a recommendation for treatment or further testing to the individual or the third party.

17. A computer-implemented system comprising:

a server comprising at least one processor configured to generate a machine learning classifier that classifies medical data, including image data, into one of a plurality of classifications, wherein the machine learning classifier is generated by
training a convolutional neural network using non-domain images that are not labeled with any of the plurality of classifications, and
retraining upper layers of the convolutional neural network using domain images that are ophthalmic images labeled with one or more of the plurality of classifications, while retaining lower layers of the convolutional neural network that were trained using the non-domain images;

a medical imaging device configured to capture an ophthalmic image of an individual;

an electronic device operatively coupled to the medical imaging device, said electronic device comprising at least one processor, a memory, and an operating system; and a computer program stored in the memory of the electronic device, the computer program including instructions configured to, when executed by the at least one processor of the electronic device,
control the medical imaging device to capture the ophthalmic image of the individual,
evaluate the ophthalmic image using the machine learning classifier to generate a determination of an ophthalmic disease, disorder, or condition, the determination having a sensitivity of at least 90% and a specificity of at least 90% when tested against an independent data set of at least 200 samples, and
provide the determination to the individual or a third party.

18. The system of claim 17, wherein the ophthalmic image of the individual comprises a retinal image.

19. The system of claim 18, wherein the retinal image is an optical coherence tomography (OCT) image.

20. The system of claim 18, wherein the medical imaging device is an optical coherence tomography (OCT) scanner.

21. The system of claim 17, wherein evaluating the ophthalmic image comprises uploading the ophthalmic image to the server for remote analysis of the ophthalmic image using the machine learning classifier.

22. The system of claim 17, wherein the ophthalmic disease, disorder, or condition is a retinal disease or condition.

23. The system of claim 22, wherein the retinal disease or condition is age-related macular degeneration (AMD), diabetic macular edema (DME), choroidal neovascularization (CNV), or diabetic retinopathy.

24. The system of claim 17, wherein the computer program is further configured to provide a recommendation for treatment or further testing to the individual or the third party.

\* \* \* \* \*